United States Patent
De Silva et al.

(10) Patent No.: US 11,548,930 B2
(45) Date of Patent: Jan. 10, 2023

(54) INTRATUMORAL VACCINATION

(71) Applicant: Heat Biologics, Inc., Durham, NC (US)

(72) Inventors: Suresh De Silva, Durham, NC (US); Taylor Schreiber, Durham, NC (US)

(73) Assignee: Heat Biologics, Inc., Durham, NC (US)

(\*) Notice: Subject to any disclaimer, the term of this patent is extended or adjusted under 35 U.S.C. 154(b) by 445 days.

(21) Appl. No.: 16/497,672

(22) PCT Filed: Apr. 3, 2018

(86) PCT No.: PCT/US2018/025791
§ 371 (c)(1),
(2) Date: Sep. 25, 2019

(87) PCT Pub. No.: WO2018/187260
PCT Pub. Date: Oct. 11, 2018

(65) Prior Publication Data
US 2020/0031901 A1    Jan. 30, 2020

Related U.S. Application Data

(60) Provisional application No. 62/599,458, filed on Dec. 15, 2017, provisional application No. 62/481,219, filed on Apr. 4, 2017.

(51) Int. Cl.
| | | |
|---|---|---|
| C07K 14/705 | (2006.01) | |
| A61P 35/00 | (2006.01) | |
| A61K 39/00 | (2006.01) | |
| A61K 9/00 | (2006.01) | |
| A61K 39/39 | (2006.01) | |
| A61K 41/00 | (2020.01) | |

(52) U.S. Cl.
CPC ...... *C07K 14/70575* (2013.01); *A61K 9/0019* (2013.01); *A61K 39/001176* (2018.08); *A61K 39/39* (2013.01); *A61K 41/0047* (2013.01); *A61P 35/00* (2018.01); *A61K 2039/572* (2013.01); *A61K 2039/585* (2013.01); *A61K 2039/70* (2013.01)

(58) Field of Classification Search
CPC .. A61K 2300/00; A61K 39/0011; A61K 9/39; C07K 14/4702; C07K 2317/75; C07K 2319/30
See application file for complete search history.

(56) References Cited

U.S. PATENT DOCUMENTS

| | | |
|---|---|---|
| 4,690,915 A | 9/1987 | Rosenberg |
| 5,188,964 A | 2/1993 | McGuire et al. |
| 5,217,891 A | 6/1993 | Brake et al. |
| 5,232,833 A | 8/1993 | Sanders et al. |
| 5,348,945 A | 9/1994 | Berberian et al. |
| 5,719,044 A | 2/1998 | Shoseyov et al. |
| 5,747,332 A | 5/1998 | Wallen et al. |
| 5,750,119 A | 5/1998 | Srivastava |
| 5,830,464 A | 11/1998 | Srivastava |
| 5,837,251 A | 11/1998 | Srivastava |
| 5,948,646 A | 9/1999 | Srivastava |
| 5,961,979 A | 10/1999 | Srivastava |
| 5,985,270 A | 11/1999 | Srivastava |
| 5,997,873 A | 12/1999 | Srivastava |
| 6,007,821 A | 12/1999 | Srivastava et al. |
| 6,017,540 A | 1/2000 | Srivastava et al. |
| 6,017,544 A | 1/2000 | Srivastava |
| 6,030,618 A | 2/2000 | Srivastava |
| 6,048,530 A | 4/2000 | Srivastava |
| 6,130,087 A | 10/2000 | Srivastava et al. |
| 6,136,315 A | 10/2000 | Srivastava |
| 6,156,302 A | 12/2000 | Srivastava |
| 6,162,436 A | 12/2000 | Srivastava |
| 6,168,793 B1 | 1/2001 | Srivastava |
| 6,322,790 B1 | 11/2001 | Srivastava |
| 6,328,957 B1 | 12/2001 | Colston et al. |
| 6,331,299 B1 | 12/2001 | Rothman et al. |
| 6,383,493 B1 | 5/2002 | Srivastava et al. |
| 6,383,494 B1 | 5/2002 | Srivastava et al. |
| 6,387,374 B1 | 5/2002 | Srivastava et al. |
| 6,399,070 B1 | 6/2002 | Srivastava et al. |
| 6,403,095 B1 | 6/2002 | Srivastava et al. |
| 6,406,700 B1 | 6/2002 | Srivastava |
| 6,410,026 B1 | 6/2002 | Srivastava |
| 6,410,027 B1 | 6/2002 | Srivastava |

(Continued)

FOREIGN PATENT DOCUMENTS

| | | |
|---|---|---|
| CA | 2158655 A1 | 9/1994 |
| DE | 19602985 A1 | 7/1997 |

(Continued)

OTHER PUBLICATIONS

Fromm et al. Gp96-Ig/Costimulator (OX40L, ICOSL, or 4-1BBL) combination vaccine improves T-cell priming and enhances immunity, memory, and tumor elimination. Cancer Immunol. Res. 4, 766-778, 2016. (Year: 2016).*

Singh et al. Induction of potent systemic anti-melanoma immunity through intratumoral CD40 activation and checkpoint blockade. J. Immunother. Cancer, 3, suppl. 2, Abstract No. P313, 2015. (Year: 2015).*

Dai et al. Cell surface expression of heat shock protein gp96 enhances cross-presentation of cellular antigens and the generation of tumor-specific T cell memory. Cancer Immunity, 3, p. 1, 2003. (Year: 2003).*

(Continued)

*Primary Examiner* — Elly-Gerald Stoica
(74) *Attorney, Agent, or Firm* — Morgan, Lewis & Bockius LLP

(57) ABSTRACT

The present disclosure relates to, inter alia, a method for treating a tumor by intratumorally delivering an effective amount of a composition comprising an expression vector that comprises a first nucleotide sequence encoding a secretable vaccine protein, and a second nucleotide sequence encoding a T cell costimulatory fusion protein.

12 Claims, 9 Drawing Sheets
Specification includes a Sequence Listing.

(56) References Cited

U.S. PATENT DOCUMENTS

| | | |
|---|---|---|
| 6,410,028 B1 | 6/2002 | Srivastava |
| 6,436,404 B1 | 8/2002 | Srivastava et al. |
| 6,447,780 B1 | 9/2002 | Srivastava et al. |
| 6,447,781 B1 | 9/2002 | Srivastava |
| 6,451,316 B1 | 9/2002 | Srivastava |
| 6,455,048 B1 | 9/2002 | Srivastava et al. |
| 6,455,503 B1 | 9/2002 | Srivastava |
| 6,461,615 B1 | 10/2002 | Srivastava |
| 6,468,540 B1 | 10/2002 | Srivastava |
| 6,475,490 B1 | 11/2002 | Srivastava et al. |
| 6,605,464 B1 | 8/2003 | Rothman et al. |
| 6,610,659 B1 | 8/2003 | Pramod |
| 6,641,812 B2 | 11/2003 | Rothman et al. |
| 6,656,679 B2 | 12/2003 | Rothman et al. |
| 6,663,868 B1 | 12/2003 | Rothman et al. |
| 6,673,348 B2 | 1/2004 | Rothman et al. |
| 6,719,974 B1 | 4/2004 | Rothman et al. |
| 6,761,892 B1 | 7/2004 | Rothman et al. |
| 6,797,480 B1 | 9/2004 | Srivastava |
| 6,984,389 B2 | 1/2006 | Li |
| 7,132,109 B1 | 11/2006 | Srivastava |
| 8,475,785 B2 | 7/2013 | Podack et al. |
| 8,685,384 B2 | 4/2014 | Podack et al. |
| 8,968,720 B2 | 3/2015 | Podack et al. |
| 9,238,064 B2 | 1/2016 | Podack et al. |
| 2003/0170756 A1 | 9/2003 | Berd |
| 2005/0019752 A1 | 1/2005 | Franchini et al. |
| 2005/0221395 A1 | 10/2005 | Zabrecky et al. |
| 2007/0141666 A1 | 6/2007 | Dupraz et al. |
| 2008/0019972 A1 | 1/2008 | Andrieu |
| 2008/0089901 A1 | 4/2008 | Hanke et al. |
| 2008/0311137 A1* | 12/2008 | La Monica ...... C07K 14/70503 424/184.1 |
| 2009/0162404 A1 | 6/2009 | Podack |
| 2010/0136032 A1 | 6/2010 | Weinberg et al. |
| 2010/0247562 A1 | 9/2010 | Gong et al. |
| 2011/0059041 A1 | 3/2011 | Truneh et al. |
| 2011/0086057 A1 | 4/2011 | Soto-Jean et al. |
| 2011/0123552 A1 | 5/2011 | Bakker et al. |
| 2011/0171211 A1 | 7/2011 | Podack et al. |
| 2011/0250229 A1 | 10/2011 | Podack et al. |
| 2012/0034242 A1 | 2/2012 | Jooss et al. |
| 2012/0093825 A1 | 4/2012 | Renauld et al. |
| 2012/0100173 A1 | 4/2012 | Leclair et al. |
| 2012/0258046 A1 | 10/2012 | Mutzke |
| 2013/0045202 A1 | 2/2013 | Irving et al. |
| 2013/0052160 A1 | 2/2013 | Zitvogel et al. |
| 2013/0121960 A1 | 5/2013 | Sadelain et al. |
| 2013/0195800 A1 | 8/2013 | Roeth et al. |
| 2013/0209511 A1 | 8/2013 | Mebatsion et al. |
| 2014/0037682 A1 | 2/2014 | Podack et al. |
| 2014/0056939 A1* | 2/2014 | Thielemans ......... A61K 38/177 424/204.1 |
| 2014/0107391 A1 | 4/2014 | Srivastava et al. |
| 2014/0134650 A1 | 5/2014 | Hawtin et al. |
| 2014/0286991 A1 | 9/2014 | Podack et al. |
| 2014/0335050 A1 | 11/2014 | Haggerty et al. |
| 2014/0335086 A1 | 11/2014 | Podack et al. |
| 2015/0191525 A1 | 7/2015 | Epstein et al. |
| 2015/0368350 A1 | 12/2015 | Tykocinksi et al. |
| 2016/0024176 A1 | 1/2016 | Damschroder et al. |
| 2016/0058852 A1 | 3/2016 | Ter Meulen et al. |
| 2016/0250322 A1 | 9/2016 | Schreiber et al. |
| 2016/0256527 A1 | 9/2016 | Gurney |
| 2016/0289645 A1 | 10/2016 | Tufaro et al. |
| 2016/0324952 A1* | 11/2016 | Bian ....................... A61P 43/00 |
| 2017/0182156 A1 | 6/2017 | Khleif |

FOREIGN PATENT DOCUMENTS

| | | |
|---|---|---|
| GB | 2251186 A | 7/1992 |
| WO | WO 89/12455 A1 | 12/1989 |
| WO | WO 90/02564 A1 | 3/1990 |
| WO | WO 91/02077 A1 | 2/1991 |
| WO | WO 91/15572 A1 | 10/1991 |
| WO | WO 92/01717 A1 | 2/1992 |
| WO | WO 92/08484 A1 | 5/1992 |
| WO | WO 92/08488 A1 | 5/1992 |
| WO | WO 93/14118 A1 | 7/1993 |
| WO | WO 93/17712 A1 | 9/1993 |
| WO | WO 93/18146 A2 | 9/1993 |
| WO | WO 93/18147 A1 | 9/1993 |
| WO | WO 93/21529 A1 | 10/1993 |
| WO | WO 94/03208 A1 | 2/1994 |
| WO | WO 94/03599 A1 | 2/1994 |
| WO | WO 94/04676 A1 | 3/1994 |
| WO | WO 94/11513 A1 | 5/1994 |
| WO | WO 95/04824 A1 | 2/1995 |
| WO | WO 95/06725 A1 | 3/1995 |
| WO | WO 95/24923 A2 | 9/1995 |
| WO | WO 96/01611 A1 | 1/1996 |
| WO | WO 96/02143 A1 | 2/1996 |
| WO | WO 96/10411 A1 | 4/1996 |
| WO | WO 96/10419 A2 | 4/1996 |
| WO | WO 96/31613 A1 | 10/1996 |
| WO | WO 97/06685 A1 | 2/1997 |
| WO | WO 97/06821 A1 | 2/1997 |
| WO | WO 97/06828 A1 | 2/1997 |
| WO | WO 97/10000 A1 | 3/1997 |
| WO | WO 97/10001 A1 | 3/1997 |
| WO | WO 97/10002 A1 | 3/1997 |
| WO | WO 97/26910 A2 | 7/1997 |
| WO | WO 97/35619 A1 | 10/1997 |
| WO | WO 98/23735 A1 | 6/1998 |
| WO | WO 99/42121 A1 | 8/1999 |
| WO | WO 03/005964 A2 | 1/2003 |
| WO | WO 04/032865 A2 | 4/2004 |
| WO | WO 05/030136 A2 | 4/2005 |
| WO | WO 05/058950 A2 | 6/2005 |
| WO | WO 05/092373 A1 | 10/2005 |
| WO | WO 2009/114085 A2 | 9/2009 |
| WO | WO 2009/114110 A1 | 9/2009 |
| WO | WO 2009/117116 A2 | 9/2009 |
| WO | WO 2010/060026 A1 | 5/2010 |
| WO | WO 2011/146828 A2 | 11/2011 |
| WO | WO 2012/116142 A2 | 8/2012 |
| WO | WO 2012/166617 A2 | 12/2012 |
| WO | WO 2014/140884 A2 | 9/2014 |
| WO | WO 2014/140904 A2 | 9/2014 |
| WO | WO 2015/131176 A1 | 9/2015 |

OTHER PUBLICATIONS

Anderson, et al., "Lag-3, Tim-3, and TIGIT: Co-inhibitory Receptors with Specialized Functions in Immune Regulation," Immunity, May 17, 2016, vol. 44, pp. 989-1004.

Bloch, et al., "Heat-shock protein peptide complex-96 vaccination for recurrent glioblastoma: a phase II, single-arm trial," Neuro-Oncology, 2013,16(2), pp. 274-279.

Callahan, et al., "Targeting T Cell Co-receptors for Cancer Therapy," Immunity, May 17, 2016, vol. 44, pp. 1069-1078.

Curran, et al., "Editorial: Advances in Combination Tumor Immunotherapy," Frontiers in Oncology, Sep. 2015, vol. 5, No. 198, pp. 1-2.

Curti, et al., "OX40 Is a Potent Immune-Stimulating Target in Late-Stage Cancer Patients," Cancer Res, 2013, 73(24), pp. 7189-7198.

De Visser, et al., "Paradoxical Roles of the Immune System during Cancer Development," Nature, Jan. 2006, vol. 6, pp. 24-37.

Guo, et al., "PD-1 Blockade and OX40 Triggering Synergistically Protects against Tumor Growth in a Murine Model of Ovarian Cancer," Plos One, Feb. 2014, vol. 9, No. 2, pp. 1-10.

International Search Report and Written Opinion PCT/US2016/016682, dated Jun. 2, 2016, 8 pages.

Kanagavelu, et al., "Soluble multi-trimeric TNF superfamily ligand adjuvants enhance immune responses to a HIV-1 Gag DNA vaccine," Vaccine, Jan. 2012, 30(4), 32 pages.

Khalil, et al., "The Future of Cancer Treatment: Immunomodulation, Cars and Combination Immunotherapy," Nature Reviews Clinical Oncology, 2016, pp. 1-18.

(56) References Cited

OTHER PUBLICATIONS

Ledford, "The Perfect Blend," Nature, Apr. 2016, vol. 532, pp. 162-164.
Linch, et al., "OX40 Agonists and Combination Immunotherapy: Putting the Pedal to the Metal," Frontiers in Oncology, Feb. 2015, vol. 5, No. 34, pp. 1-14.
Liu, et al., "Enhancement of Cancer Radiation Therapy by Use of Adenovirus-Mediated Secretable Glucose-Regulated Protein 94/gp96 Expression," Cancer Res 2005, Oct. 2005, 65(20) pp. 9126-9131.
Mahoney, et al., "Combination Cancer Immunotherapy and New Immunomodulatory Targets," Nature Reviews Drug Discovery, Aug. 2015, vol. 14, pp. 561-584.
Mellman, et al., "Cancer immunotherapy comes of age," Nature, Dec. 2011, vol. 480, pp. 480-489.
Moran, et al., "The TNFRs OX40, 4-1 BB, and CD40 as targets for cancer immunotherapy," Current Opinion in Immunology, 2013, 25, pp. 230-237.
Oizumi, et al., "Molecular and Cellular Requirements for Enhanced Antigen Cross-Presentation to CD8 Cytotoxic T Lymphocytes," The Journal of Immunology, 2007, vol. 179, pp. 2310-2317.
Oizumi, et al., "Surmounting Tumor-induced Immune Suppression by Frequent Vaccination or Immunization in the Absence of B Cells," J Immunother, May 2008, vol. 31, No. 4, pp. 394-401.
Pardoll, "The Blockade of Immune Checkpoints in Cancer Immunotherapy," Nature Reviews Cancer, 2012, vol. 12, pp. 252-264.
Raez, et al., "CD8 T Cell Response in A Phase I Study of Therapeutic Vaccination of Advanced NSCLC with Allogeneic Tumor Cells Secreting Endoplasmic Reticulum-Chaperone Gp96-Ig-Peptide Complexes," Advances in Lung Cancer, 2013, vol. 2, No. 1, pp. 9-18.
Schildberg, et al., "Coinhibitory Pathways in the B7-CD28 Ligand-Receptor Family," Immunity, May 17, 2016, vol. 44, pp. 955-972.
Schreiber, et al., "Tumor-Induced Suppression of CTL Expansion and Subjugation by gp96-Ig Vaccination," Cancer Res, Mar. 2009, vol. 69 No. 5, pp. 2026-2033.
Schreiber, et al., "Tumor Immunogenicity and Responsiveness to Cancer Vaccine Therapy: The State of the Art", Seminars in Immunology, 2010, vol. 22, pp. 105-112.
Schreiber, et al., "T Cell Costimulation by TNFRSF4 and TNFRSF25 in the Context of Vaccination," J. Immunol., Oct. 2012, 189(7): pp. 3311-3318.
Strbo, et al., "Cell-secreted Gp96-Ig-Peptide Complexes Induce Lamina Propria and Intraepithelial CD8 + Cytotoxic T Lymphocytes in the Intestinal Mucosa", Nature, Mar. 2010, vol. 3, No. 2, pp. 182-192.
Tosti, et al., "HSPPC-96 vaccine in metastatic melanoma patients: from the state of the art to a possible future," Expert Rev. Vaccines, 2009, 8(11), pp. 1513-1526.
Ward-Kavanagh, et al., "The TNF Receptor Superfamily in Co-stimulating and Co-inhibitory Responses," Immunity, May 17, 2016, vol. 44, pp. 1005-1019.
Yamazaki, et al., "Cutting Edge: Tumor Secreted Heat Shock-Fusion Protein Elicits CD8 Cells for Rejection," J Immunol, 1999, vol. 163, pp. 5178-5182.
International Search Report and Written Opinion PCT Appl. No. PCT/US18/25791, dated Jul. 27, 2018, 9 pages.

* cited by examiner

FIG. 1

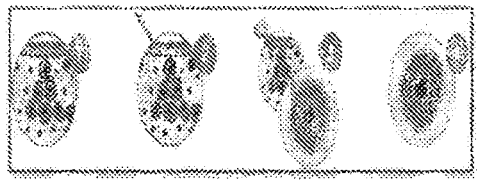

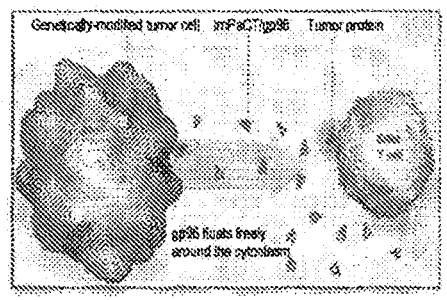

Step 1 – tumor cells are identified
Step 2 – DNA-based molecules are injected in the tumor
Step 3 – Electrical pulses are delivered via electrodes, which increases the permeability of the cell membrane
Step 4 – DNA-based molecules enter the cell nucleus and express the immune-modulatory molecules

* Gp96.Ig serves as a molecular chaperone and adjuvant that presents tumor-associated neoantigens to APCs to trigger an anti-tumor CTL response
* Fc-OX40L secreted from the tumor cell serves to enhance co-stimulations of CTLs

| Voltage (V/cm) | No. of pulses | Duration of pulse |
|---|---|---|
| 350 | 8 | 10ms |
| 1500 | 6 | 0.1ms |

INTRATUMORAL VACCINATION

RELATED APPLICATIONS

This application is a U.S. National Stage Entry of International Patent Application No. PCT/US18/25791, filed on Apr. 3, 2018, which claims priority to and the benefit of U.S. Provisional Patent Application No. 62/481,219, filed on Apr. 4, 2017, and U.S. Patent Provisional Patent Application No. 62/599,458, filed on Dec. 15, 2017, the contents of each of which are incorporated herein by reference in their entireties.

INCORPORATION BY REFERENCE OF MATERIAL SUBMITTED ELECTRONICALLY

The contents of the text file name "HTB-024PC_SequenceListing_ST25", which was created on Mar. 21, 2018 and is 70 KB in size, are hereby incorporated herein by reference in their entirety.

FIELD

This document relates, inter alia, to materials and methods for using vaccination and T-cell co-stimulation to treat a clinical condition in a subject.

BACKGROUND

Most cancer immunotherapies (IT) have a higher likelihood of succeeding if the targeted tumor has a preexisting state of inflammation elicited by the combined presentation of shared- and neo-antigens from tumor cells. Thus, novel combination treatment modalities are needed to convert non-immunogenic, 'cold' tumors into inflamed 'hot' tumors.

Gp96-Ig/Fc-OX40L is a re-engineered molecular chaperone, designed to export and deliver MHC I-associated antigens to APCs in context of the immune costimulator, OX40L. Allogeneic cancer vaccine cell lines designed to co-secrete Gp96-Ig and Fc-OX40L, generate antigen-specific CD4+/CD8+ anti-tumor responses in both highly immunogenic (CT26) and less immunogenic (B16) mouse tumors (Fromm et al., *Cancer Immunol Res,* 2016). Such a strategy allows for Gp96-Ig-mediated chaperoning of antigens from the allogeneic vaccine cell line (shared antigens), which could benefit further from increased presentation of tumor-derived peptides (neo-antigens) that are only accessible if Gp96-Ig/Fc-OX40L is expressed from within the tumor.

SUMMARY

Accordingly, in some aspects, the present invention relates to a method for treating a tumor in a subject in need thereof, comprising intratumorally delivering an effective amount of a composition comprising an expression vector that comprises a nucleotide sequence encoding a secretable vaccine protein (e.g., without limitation gp96-Ig).

In some aspects, the present invention relates to a method for treating a tumor in a subject in need thereof, comprising intratumorally delivering an effective amount of a composite comprising a first nucleotide sequence encoding a secretable vaccine protein (e.g., without limitation gp96-Ig), and a second nucleotide sequence encoding a T cell costimulatory fusion protein (e.g., without limitation OX40L-Ig, or a portion thereof binds to OX40), optionally on a single expression vector in various embodiments, the intratumoral delivery is in vivo by injection.

In aspects, the present invention relates to a method for treating a tumor in a subject in need thereof, comprising administering to a subject in need thereof a combination therapy of (1) intratumorally delivery of an effective amount of a composition comprising an expression vector that comprises a nucleotide sequence encoding a secretable vaccine protein (e.g., without limitation gp96-Ig), and (2) an effective amount of a biological cell comprising an expression vector that comprises a nucleotide sequence encoding a secretable vaccine protein (e.g., without limitation gp96-Ig).

In other aspects, the present invention relates to a method for treating a tumor in a subject in need thereof, comprising administering to a subject in need thereof a combination therapy of (1) intratumorally delivery of an effective amount of a composition comprising a first nucleotide sequence encoding a secretable vaccine protein (e.g., without limitation gp96-Ig), and a second nucleotide sequence encoding a T cell costimulatory fusion protein (e.g., without limitation OX40L-Ig, or a portion thereof that binds to OX40) and (2) an effective amount of a biological cell comprising an expression vector that comprises a first nucleotide sequence encoding a secretable vaccine protein (e.g., without limitation gp96-Ig), and a second nucleotide sequence encoding a T cell costimulatory fusion protein (e.g., without limitation OX40L-Ig, or a portion thereof that binds to OX40), wherein the T cell costimulatory fusion protein enhances activation of antigen-specific T cells when administered to the subject.

In other aspects, the present invention relates to a method for treating a tumor in a subject in need thereof, comprising administering to a subject in need thereof a combination therapy of (1) intratumorally delivery of an effective amount of a composition comprising at expression vector that composes a first nucleotide sequence encoding a secretable vaccine protein (e.g., without limitation gp96-Ig), and a second nucleotide sequence encoding a T cell costimulatory fusion protein (e.g., without limitation OX40-Ig, or a portion thereof that binds to OX40) and (2) an effective amount of a biological cell comprising an expression vector that comprises a first nucleotide sequence encoding a secretable vaccine protein (e.g., without limitation gp96-Ig), and a second nucleotide sequence encoding a T cell costimulatory fusion protein (e.g., without limitation OX40-Ig, or a portion thereof that binds to OX40), wherein the T cell costimulatory fusion protein enhances activation of antigen-specific T cells when administered to the subject.

Accordingly, in various aspects, direct intratumoral administration (i.e., in vivo, e.g., by injection into a tumor—e.g., in a primary or secondary tumor (e.g., metastatic lesion)) of an expression vector encoding a secretable vaccine protein (e.g., without limitation gp96-Ig) is paired with administration of a biological cell that has been manipulated (e.g., ex vivo) to comprise an expression vector encoding a secretable vaccine protein (e.g., without limitation gp96-Ig).

In various aspects, direct intratumoral administration (i.e., in vivo, e.g., by injection into a tumor—e.g., in a primary or secondary tumor (e.g., metastatic lesion)) of an expression vector encoding a secretable vaccine protein (e.g., without limitation gp96-Ig), and a second nucleotide sequence encoding a T cell costimulatory fusion protein is paired with administration of a biological cell that has been manipulated (e.g., ex vivo) to comprise an expression vector encoding a secretable vaccine protein (e.g., without limitation gp96-Ig), and a second nucleotide sequence encoding a T cell costimulatory fusion protein. In various embodiments, the T cell costimulatory fusion protein used in the intratumoral administration is the same as the T cell costimulatory fusion protein of the biological cell. In various embodiments, the T cell costimulatory fusion protein used in the intratumoral administration is different than the T cell costimulatory fusion protein of the biological cell.

In various embodiments, the present methods elicit a potent immune response in less-immunogenic tumors, optional a tumor with reduced inflammation ("cold tumor") relative to a responsive, inflamed tumor ("hot tumor").

In various embodiments, the present methods enhance CD4+/CD8+ T cell cross-priming to tumor neo-antigens.

BRIEF DESCRIPTION OF THE DRAWINGS

FIG. 1 shows a schematic of the present studies.

FIG. 2A shows the electroporation parameters. FIG. 2B is a bar graph that shows GP96-Ig mRNA levels in the tumor. The left bar (No EP), the middle bar (300 V/cm) and right bar (1500 V/cm) conditions. FIG. 2C is a bar graph that shows tumor lysate associated OX40L protein was quantified by qPCR and ELISA, respectively. The left bar (No EP), the middle bar (300 V/cm) and right bar (1500 V/cm) conditions.

FIG. 3A shows the experimental design. FIG. 3B shows treated tumor size post electroporation, at day 0, lines denote tumor size of 200 mm$^2$ for EP only, at day 10 lines denote tumor size of 300 mm$^2$ for EP only and at days 30 to 40 lines denote tumor size of 200 mm$^2$ for GP96-Ig/Fc-OX40L+EP. FIG. 3C shows untreated tumor size days' post electroporation, at day 0 lines denote tumor size of 200 mm$^2$ for EP only. FIG. 3D shows Ova-antigen specific CD8+ T cell expansion. FIG. 3E shows Ova-antigen specific memory precursor CD8 cells (EP only on left, Gp96-Ig/Fc-OX40L+EP on right). FIG. 3F shows an overall survival plot days' post primary tumor inoculation, day 32 shows percent survival for EP only and day 40 shows percent survival for GP96-Ig/Fc-OX40L+EP (for reference, at day 30, the top curve is Gp96-Ig/Fc-OX40L+EP and the bottom curve is EP only.

FIG. 4A shows the experimental design. FIG. 4B shows treated tumor area on day 18 post tumor inoculation. FIG. 4C shows untreated tumor area on day 13 post tumor inoculation. FIG. 4D shows overall survival in untreated, Vaccine control, Gp96-Ig/Fc-OX40L EP only, Gp96-Ig/Fc-OX40L+Vaccine only and EP+Vaccine Combo. FIG. 4E shows total CD8 T cells in tumor, (♦) No treatment, (●) Vaccine control, (∇) EP, (⊕) Vaccine, and (φ) EP+Vaccine Combo. FIG. 4F shows tetramer positive CD8 T cells in tumor, (♦) No treatment, (●) Vaccine control, (∇) EP, (⊕) Vaccine, and (φ) EP+Vaccine Combo.

DETAILED DESCRIPTION

Figures 2A, 2B:
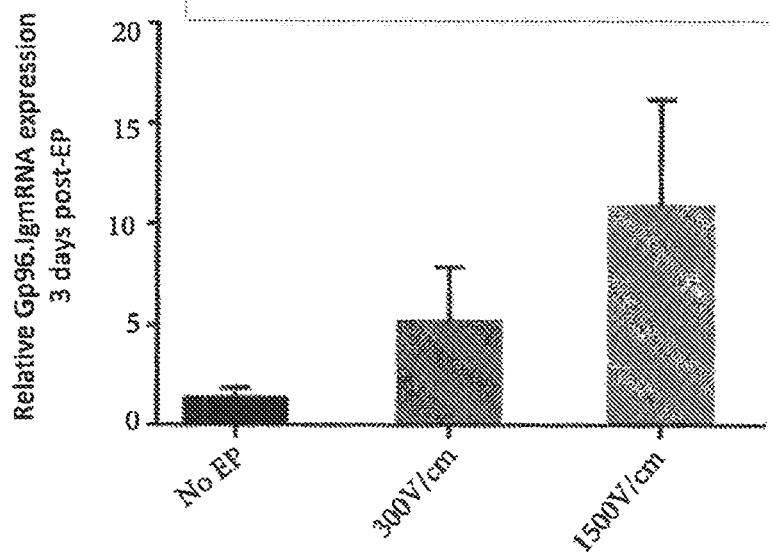
FIG. 2A-C shows optimization of electroporation (EP) conditions for Gp96-Ig/Fc-OX40L DNA delivery into B16.F10-ova melanoma tumors.

Accordingly, in some aspects, the present invention relates to a method for treating a tumor in a subject in need thereof, comprising intratumorally delivering an effective amount of a composition comprising an expression vector that comprises a nucleotide sequence encoding a secretable vaccine protein (e.g., without limitation gp96-Ig).

In some aspects, the present invention relates to a method for treating a tumor in a subject in need thereof, comprising intratumorally delivering an effective amount of a composition comprising an expression vector that comprises a first nucleotide sequence encoding a secretable vaccine protein (e.g., without limitation gp96-Ig), and a second nucleotide sequence encoding a T cell costimulatory fusion protein (e.g., without limitation OX40L-Ig, or a portion thereof that binds to OX40). In various embodiments, the intratumoral delivery is in vivo by injection.

In other aspects, the present invention relates to a method for treating a tumor in a subject in need thereof, comprising administering to a subject in need thereof a combination therapy of (1) intratumorally delivery of an effective amount of a composition comprising an expression vector that comprises a nucleotide sequence encoding a secretable vaccine protein (e.g., without limitation gp96-Ig), and (2) an effective amount of a biological cell comprising an expression vector that comprises a nucleotide sequence encoding a secretable vaccine protein (e.g., without limitation gp96-Ig).

In other aspects, the present invention relates to a method for treating a tumor in a subject in need thereof, comprising administering to a subject in need thereof a combination therapy of (1) intratumorally delivery of an effective amount of a composition comprising an expression vector that comprises a first nucleotide sequence encoding a secretable vaccine protein (e.g., without limitation gp96-Ig), and a second nucleotide sequence encoding a T cell costimulatory fusion protein (e.g., without limitation OX40L-Ig, or a portion thereof that binds to OX40) and (2) an effective amount of a biological cell comprising an expression vector that comprises a first nucleotide sequence encoding a secretable vaccine protein (e.g., without limitation gp96-Ig), and a second nucleotide sequence encoding a T cell costimulatory fusion protein (e.g., without limitation OX40L-Ig, or a portion thereof that binds to OX40), wherein the T cell costimulatory fusion protein enhances activation of antigen-specific T cells when administered to the subject.

In various embodiments, the present methods elicit a potent immune response in less-immunogenic tumors, optional a tumor with reduced inflammation ("cold tumor") relative to a responsive, inflamed tumor ("hot tumor").

In various embodiments, the present methods enhance CD4+/CD8+ T cell cross-priming to tumor neo-antigens.

Vaccine Proteins

Vaccine proteins can induce immune responses that find use in the present invention. In various embodiments, the present invention provides expression vectors comprising a nucleotide sequence that encode a secretable vaccine protein. In various embodiments, the present invention provides expression vectors comprising a first nucleotide sequence that encode a secretable vaccine protein and a second nucleotide sequence that encode a T cell costimulatory fusion protein. Compositions comprising the expression vectors of the present invention are also provided. In various embodiments, such compositions are utilized in methods of treating subjects to stimulate immune responses in the subject including enhancing the activation of antigen-specific T cells in the subject. The present compositions find use in the treatment of various diseases including cancer.

The heat shock protein (hsp) gp96, localized in the endoplasmic reticulum (ER), serves as a chaperone for peptides on their way to MHC class I and II molecules. Gp96 obtained from tumor cells and used as a vaccine can induce specific tumor immunity, presumably through the transport of tumor-specific peptides to antigen-presenting cells (APCs) (*J Immunol* 1999, 163(10):5178-5182). For example, gp96-associated peptides are cross-presented to CD8 cells by dendritic cells (DCs).

A vaccination system was developed for antitumor therapy by transfecting a gp96-Ig G1-Fc fusion protein into tumor cells, resulting in secretion of gp96-Ig in complex with chaperoned tumor peptides (see, *J Immunother* 2008, 31 (4):394-401, and references cited therein). Parenteral administration of gp96-Ig secreting tumor cells triggers robust, antigen-specific CD8 cytotoxic T lymphocyte (CTL) expansion, confined with activation of the innate immune system. Tumor-secreted gp96 causes the recruitment of DCs and natural killer (NK) cells to the site of gp96 secretion, and mediates DC activation. Further, the endocylic uptake of gp96 and its chaperoned peptides triggers peptide cross presentation via major MHC class I, as well as strong, cognate CD8 activation independent of CD4 cells.

The vectors provided herein contain a nucleotide sequence that encodes a gp96-Ig fusion protein. The coding region of human gp96 is 2,412 bases in length (SEQ ID NO:1), and encodes an 803 amino acid protein (SEQ ID NO:2) that includes a 21 amino acid signal peptide at the amino terminus, a potential transmembrane region rich in hydrophobic residues, and an ER retention peptide sequence at the carboxyl terminus (GENBANK® Accession No. X15187; see, Maki et al., *Proc Natl Acad Sci USA* 1990, 87:5658-5562). The DNA and protein sequences of human gp96 follow:

```
                                              (SEQ ID NO: 1)
atgagggccctgtgggtgctgggcctctgctgcgtcctgctgaccttcgg gtcggtcagagctgacgatgaagttgatgtggatggtacagtagaagagg atctgggtaaaagtagagaaggatcaaggacggatgatgaagtagtacag agagaggaagaagctattcagttggatggattaaatgcatcacaaataag agaacttagagagaagtcggaaaagtttgccttccaagccgaagttaaca gaatgatgaaacttatcatcaattcattgtataaaaataaagagattttc ctgagagaactgatttcaaatgcttctgatcctttagataagataaggct aatatcactgactgatgaaaatgctctttctggaaatgaggaactaacag tcaaaattaagtgtgataaggagaagaacctgctgcatgtcacagacacc ggtgtaggaatgaccagagaagagttggttaaaaaccttggtaccatagc caaatctgggacaagcgagtttttaaacaaaatgactgaagcacaggaag atggccagtcaacttctgaattgattggccagtttggtgtcggtttctat tccgccttccttgtagcagataaggttattgtcacttcaaaacacaacaa cgatacccagcacatctgggagtctgactccaatgaattttctgtaattg ctgacccaagaggaaacactctaggacggggaacgacaattacccttgtc ttaaaagaagaagcatctgattaccttgaattggatacaattaaaaatct cgtcaaaaaatattcacagttcataaactttcctatttatgtatggagca gcaagactgaaactgttgaggagcccatggaggaagaagaagcagccaaa gaagagaaagaagaatctgatgatgaagctgcagtagaggaagaagaaga agaaaagaaaaccaaagactaaaaaagttgaaaaaactgtctggactgg gaacttatgaatgatatcaaaccaatggcagagaccatcaaaagaagt
```

```
                                             -continued
agaagaagatgaatacaaagctttctacaaatcattttcaaaggaaagtg atgacccatggcttatattcactttactgctgaaggggaagttaccttc aaatcaattttatttgtacccacatctgctccacgtggtctgtttgacga atatggatctaaaaagagcgattacattaagctctatgtgcgccgtgtat tcatcacagacgacttccatgatatgatgcctaaatacctcaattttgtc aagggtgtggtggactcagatgatctcccccttgaatgtttcccgcgagac tcttcagcaacataaactgcttaaggtgattaggaagaagcttgttcgta aaacgctggacatgatcaagaagattgctgatgataaatacaatgatact ttttggaaagaatttggtaccaacatcaagcttggtgtgattgaagacca ctcgaatcgaacacgtcttgctaaacttcttaggttccagtcttctcatc atccaactgacattactagcctagaccagtatgtggaaagaatgaaggaa aaacaagacaaaatctacttcatggctgggtccagcagaaaagaggctga atcttctccatttgttgagcgacttctgaaaaagggctatgaagttattt acctcacagaacctgtggatgaatactgtattcaggcccttcccgaattt gatgggaagaggttccagaatgttgccaaggaaggagtgaagttcgatga aagtgagaaaactaaggagagtcgtgaagcagttgagaaagaatttgagc ctctgctgaattggatgaaagataaagccctaaggacaagattgaaaag gctgtggtgtctcagcgcctgacagaatctccgtgtgctttggtggccag ccagtacggatggtctggcaacatggagagaatcatgaaagcacaagcgt accaaacgggcaaggacatctctacaaattactatgcgagtcagaagaaa acatttgaaattaatcccagacacccgctgatcagagacatgcttcgacg aattaaggaagatgaagatgataaaacagttttggatcttgctgtggttt tgtttgaaacagcaacgcttcggtcagggtatcttttaccagacactaaa gcatatggagatagaatagaaagaatgcttcgcctcagtttgaacattga ccctgatgcaaaggtggaagaagagcccgaagaagaacctgaagagacag cagaagacacaacagaagacacagagcaagacgaagatgaagaaatggat gtgggaacagatgaagaagaagaaacagcaaaggaatctacagctgaaaa agatgaattgtaa
```

```
                                              (SEQ ID NO: 2)
MRALWVLGLCCVLLTFGSVRADDEVDVDGTVEEDLGKSREGSRTDDEVVQ

REEEAIQLDGLNASQIRELREKSEKFAFQAEVNRMMKLIINSLYKNKEIF

LRELISNASDALDKIRLISLTDENALSGNEELTVKIKCDKEKNLLHVTDT

GVGMTREELVKNLGTIAKSGTSEFLNKMTEAQEDGQSTSELIGQFGVGFY

SAFLVADKVIVTSKHNNDTQHIWESDSNEFSVIADPRGNTLGRGTTITLV

LKEEASDYLELDTIKNLVKKYSQFINFPIYVWSSKTETVEEPMEEEEAAK

EEKEESDDEAAVEEEEEEKKPKTKKVEKTVWDWELMNDIKPIWQRPSVKE

VEEDEYKAFYKSFSKESDDPMAYIHFTAEGEVTFKSILFVPTSAPRGLFD

EYGSKKSDYIKLYVRRVFITDDFHDMMPKYLNFVKGVVDSDDLPLNVSRE

TLQQHKLLKVIRKKLVRKTLDMIKKIADDKYNDTFWKEFGTNIKLGVIED

HSNRTRLAKLLRFQSSHHPTDITSLDQYVERMKEKQDKIYFMAGSSRKEA

ESSPFVERLLKKGYEVIYLTEPVDEYCIQALPEFDGKRFQNVAKEGVKFD
```

-continued

```
ESEKTKESREAVEKEFEPLLNWMKDKALKDKIEKAVVSQRLTESPCALVA

SQYGWSGNMERIMKAQAYQTGKDISTNYYASQKKTFEINPRHPLIRDMLR

RIKEDEDDKTVLDLAVVLFETATLRSGYLLPDTKAYGDRIERMLRLSLNI

DPDAKVEEEPEEEPEETAEDTTEDTEQDEDEEMDVGTDEEEETAKESTAE

KDEL.
```

A nucleic acid encoding a gp96-Ig fusion sequence can be produced using the methods described in U.S. Pat. No. 8,685,384, which is incorporated herein by reference in its entirety. In some embodiments, the gp96 portion of a gp96-Ig fusion protein can contain all or a portion of a wild type gp96 sequence (e.g., the human sequence set forth in SEQ ID NO:2). For example, a secretable gp96-Ig fusion protein can include the first 799 amino acids of SEQ ID NO:2, such that it lacks the C-terminal KDEL (SEQ ID NO:3) sequence. Alternatively, the gp96 portion of the fusion protein can have an amino acid sequence that contains one or more substitutions, deletions, or additions as compared to the first 799 amino acids of the wild type gp96 sequence, such that it has at least 90% (e.g., at least 90%, at least 91%, at least 92%, at least 93%, at least 94%, at least 95%, at least 96%, at least 97%, at least 98%, or at least 99%) sequence identity to the wild type polypeptide.

As used throughout this disclosure, the percent sequence identity between a particular nucleic acid or amino acid sequence and a sequence referenced by a particular sequence identification number is determined as follows. First, a nucleic acid or amino acid sequence is compared to the sequence set forth in a particular sequence identification number using the BLAST 2 Sequences (Bl2seq) program from the stand-alone version of BLASTZ containing BLASTN version 2.0.14 and BLASTP version 2.0.14. This stand-alone version of BLASTZ can be obtained online at fr.com/blast or at ncbi.nlm.nih.gov. Instructions explaining how to use the Bl2seq program can be found in the readme file accompanying BLASTZ. Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to -1; -r is set to 2; and all other options are left at their default setting. For example, the following command can be used to generate an output file containing a comparison between two sequences: C:\Bl2seq -i c:\seq1.txt -j c:\seq2.txt -p blastn -o c:\output.txt -q -1 -r 2. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq -i c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence (e.g., SEQ ID NO:1), or by an articulated length (e.g., 100 consecutive nucleotides or amino acid residues from a sequence set forth in an identified sequence), followed by multiplying the resulting value by 100. For example, a nucleic acid sequence that has 2,200 matches when aligned with the sequence set forth in SEQ ID NO:1 is 91.2 percent identical to the sequence set forth in SEQ ID NO:1 (i.e., 2,000÷2,412×100=91.2). It is noted that the percent sequence identity value is rounded to the nearest tenth. For example, 75.11, 75.12, 75.13, and 75.14 is rounded down, to 75.1, while 75.15, 75.16, 75.17, 75.18, and 75.19 is rounded up to 75.2. It also is noted that the length value will always be an integer.

Thus, in some embodiments, the gp96 portion of nucleic acid encoding a gp96-Ig fusion polypeptide can encode an amino acid sequence that differs from the wild type gp36 polypeptide at one or more amino acid positions, such that it contains one or more conservative substitutions, non-conservative substitutions, splice variants, isoforms, homologues from other species, and polymorphisms.

As defined herein, a "conservative substitution" denotes the replacement of an amino acid residue by another, biologically similar, residue. Typically, biological similarity, as referred to above, reflects substitutions on the wild type sequence with conserved amino acids. For example, conservative amino acid substitutions would be expected to have little or no effect on biological activity, particularly if they represent less than 10% of the total number of residues in the polypeptide or protein. Conservative substitutions may be made, for instance, on the basis of similarity in polarity, charge, size, solubility, hydrophobicity, hydrophilicity, and/or the amphipathic nature of the amino acid residues involved. The 20 naturally occurring, amino acids can be grouped into the following six standard amino acid groups: (1) hydrophobic: Met, Ala, Val, Leu, Ile; (2) neutral hydrophilic: Cys, Ser, Thr; Asn, Gln; (3) acidic: Asp, Glu; (4) basic: His, Lys, Arg; (5) residues that influence chain orientation: Gly, Pro; and (6) aromatic: Trp, Tyr, Phe. Accordingly, conservative substitutions may be effected by exchanging an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt α-helices. Additional examples of conserved amino acid substitutions, include, without limitation, the substitution of one hydrophobic residue for another, such as isoleucine, valine, leucine, or methionine, or the substitution of one polar residue for another, such as the substitution of arginine for lysine, glutamic for aspartic acid, or glutamine for asparagine, and the like. The term "conservative substitution" also includes the use of a substituted amino acid residue in place of an un-substituted parent amino acid residue, provided that antibodies raised to the substituted polypeptide also immunoreact with the un-substituted polypeptide.

As used herein, "non-conservative substitutions" are defined as exchanges of an amine acid by another amino acid listed in a different group of the six standard amino acid groups (1) to (6) shown above.

In various embodiments, the substitutions may also include non-classical amino acids (e.g., selenocysteine, pyrrolysine, N-formylmethionine, β-alanine, GABA and δ-Aminolevulinic acid, 4-aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, hydroxyproline, hydroxyproline, sarcosme, citrulline, homocitrulline, cysteic acid, t-butylglycine, t-butylalanine, phenylglycine, cyclohexylalanine, β-alanine, fluoro-amino acids, designer amino acids such as β methyl amino acids, C α-methyl amino acids, N α-methyl amino acids, and amino acid analogs in general).

Mutations may also be made to the nucleotide sequences of the present fusion proteins by reference to the genetic code, including taking into account codon degeneracy.

The Ig portion ("tag") of a gp96-Ig fusion protein can contain, for example, a non-variable portion of an immunoglobulin molecule (e.g., an IgG1, IgG2, IgG3, IgG4, IgM, IgA, or IgE molecule). Typically, such portions contain at least functional CH2 and CH3 domains of the constant region of an immunoglobulin heavy chain. Fusions also can be made using the carboxyl terminus of the Fc portion of a constant domain, or a region immediately amino-terminal to the CH1 of the heavy or light chain. The Ig tag can be from a mammalian (e.g., human, mouse, monkey, or rat) immunoglobulin, but human immunoglobulin can be particularly useful when the gp96-Ig fusion is intended for in vivo use for humans.

DNAs encoding immunoglobulin light or heavy chain constant regions are known or readily available from cDNA libraries. See, for example, Adams et al., *Biochemistry* 1980, 19:2711-2719; Gough et al., *Biochemistry* 1980 19:2702-2710; Dolby et al., *Proc Natl Acad Sci USA* 1980, 77:6027-6031; Rice et al., *Proc Natl Acad Sci USA* 1982, 79:7862-7865; Falkner et al., *Nature* 1982, 298:286-288; and Morrison et al., *Ann Rev Immunol* 1984, 2:239-256. Since many immunological reagents and labeling systems are available for the detection of immunoglobulins, gp96-Ig fusion proteins can readily be detected and quantified by a variety of immunological techniques known in the art, such as enzyme-linked immunosorbent assay (ELISA), immuno-precipitation, and fluorescence activated cell sorting (FACS). Similarly, if the peptide tag is an epitope with readily available antibodies, such reagents can be used with the techniques mentioned above to detect, quantitate, and isolate gp96-Ig fusions.

In various embodiments, the gp96-Ig fusion protein and/or the costimulatory molecule fusions, comprises a linker. In various embodiments, the linker may be derived from naturally-occurring multi-domain proteins or are empirical linkers as described, for example, in Chichili et al., (2013), Protein Sci. 22(2):153-167, Chen et al., (2013), Adv Drug Deliv Rev. 65(10):1357-1369, the entire contents of which are hereby incorporated by reference. In some embodiments, the linker may be designed using linker designing databases and computer programs such as those described in Chen et al., (2013), Adv Drug Deliv Rev. 65(10): 1357-1369 and Crasto et. al., (2000), Protein Eng. 13(5):309-312, the entire contents of which are hereby incorporated by reference.

In some embodiments, the linker is a synthetic linker such as PEG.

In other embodiments, the linker is a polypeptide. In some embodiments, the linker is less than about 100 amino acids long. For example, the linker may be less than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long. In some embodiments, the linker is flexible. In another embodiment, the linker is rigid. In various embodiments, the linker is substantially comprised of glycine and serine residues (e.g., about 30%, or about 40%, or about 50%, or about 60%, or about 70%, or about 80%, or about 90%, or about 95%, or about 97% glycines and serines).

In various embodiments, the linker is a hinge region of an antibody (e.g., of IgG, IgA, IgD, and IgE, inclusive of subclasses (e.g. IgG1, IgG2, IgG3, and IgG4, and IgA1 and IgA2)). The hinge region, found in IgG, IgA, IgD, and IgE class antibodies, acts as a flexible spacer, allowing the Fab portion to move freely in space. In contrast to the constant regions, the hinge domains are structurally diverse, varying in both sequence and length among immunoglobulin classes and subclasses. For example, the length and flexibility of the hinge region varies among the IgG subclasses. The hinge region of IgG1 encompasses amino acids 216-231 and, because it is freely flexible, the Fab fragments can rotate about their axes of symmetry and move within a sphere centered at the first of two inter-heavy chain disulfide bridges. IgG2 has a shorter hinge than IgG1, with 12 amino acid residues and four disulfide bridges. The hinge region of IgG2 lacks a glycine residue, is relatively short, and contains a rigid poly-proline double helix, stabilized by extra inter-heavy chain disulfide bridges. These properties restrict the flexibility of the IgG2 molecule. IgG3 differs from the other subclasses by its unique extended hinge region (about four times as long as the IgG1 hinge), containing 62 amino acids (including 21 prolines and 11 cysteines), forming an inflexible poly-proline double helix. In IgG3, the Fab fragments are relatively far away from the Fc fragment, giving the molecule a greater flexibility. The elongated hinge in IgG3 is also responsible for its higher molecular weight compared to the other subclasses. The hinge region of IgG4 is shorter than that of IgG1 and its flexibility is intermediate between that of IgG1 and IgG2. The flexibility of the hinge regions reportedly decreases in the order IgG3>IgG1>IgG4>IgG2.

Additional illustrative linkers include, but are not limited to, linkers having the sequence LE, GGGGS (SEQ ID NO:26), (GGGGS)$_n$ (n=1-4) (SEQ ID NO: 27), (Gly)$_8$ (SEQ ID NO:28), (Gly)$_6$ (SEQ ID NO:29), (EAAAK)$_n$ (n=1-3) (SEQ ID NO: 30). A(EAAAK)$_n$A (n=2-5) (SEQ ID NO: 31), AEAAAKEAAAKA (SEQ ID NO: 32), A(EAAAK)$_4$ALEA (EAAAK)$_4$A (SEQ ID NO: 33), PAPAP (SEQ ID NO: 34), KESGSVSSEQLAQFRSLD (SEQ ID NO: 35), EGKSSGSGSESKST (SEQ ID NO: 36), GSAGSAAGSGEF (SEQ ID NO: 37), and (XP)$_n$, with X designating any amino acid, e.g., Ala, Lys, or Glu.

In various embodiments, the linker may be functional. For example, without limitation, the linker may function to improve the folding and/or stability, improve the expression, improve the pharmacokinetics, and/or improve the bioactivity of the present compositions. In another example, the linker may function to target the compositions to a particular cell type or location.

In some embodiments, a gp96 peptide can be fused to the hinge, CH2 and CH3 domains of murine IgG1 (Bowen et al., *J Immunol* 1996, 156:442-449). This region of the IgG1 molecule contains three cysteine residues that normally are involved in disulfide bonding with other cysteines in the Ig molecule. Since none of the cysteines are required for the peptide to function as a tag, one or more of these cysteine residues can be substituted by another amino acid residue, such as, for example, serine.

Various leader sequences known in the art also can be used for efficient secretion of gp96-Ig fusion proteins from bacterial and mammalian cells (see, von Heijne, *J Mol Biol* 1985, 184:99-105). Leader peptides can be selected based on the intended host cell, and may include bacterial, yeast, viral, animal, and mammalian sequences. For example, the herpes virus glycoprotein D leader peptide is suitable for use in a variety of mammalian cells. Another leader peptide for use in mammalian cells can be obtained from the V-J2-C region of the mouse immunoglobulin kappa chain (Bernard et al., *Proc Natl Acad Sci USA* 1981, 78:5812-5816). DNA sequences encoding peptide tags or leader peptides are known or readily available from libraries or commercial suppliers, and are suitable in the fusion proteins described herein.

Furthermore, in various embodiments, one may substitute the gp96 of the present disclosure with one or more vaccine proteins. For instance, various heat shock proteins are among the vaccine proteins. In various embodiments, the heat shock protein is one or more of a small hsp, hsp40, hsp60, hsp70, hsp90, and hsp110 family member, inclusive of fragments, variants, mutants, derivatives or combinations thereof (Hickey, et al., 1989, *Mol. Cell. Biol.* 9:2615-2626; Jindal, 1989, *Mol. Cell. Biol.* 9:2279-2283).

T-Cell Co-Stimulation

In addition to a gp96-Ig fusion protein, the expression vectors provided herein can encode one or more biological response modifiers. In various embodiments, the present expression vectors can encode one or more T cell costimulatory molecules.

In various embodiments, the present expression vectors allow for a robust, antigen-specific CD8 cytotoxic T lymphocyte (CTL) expansion. In various embodiments, the present expression vectors selectively enhance CD8 cytotoxic T lymphocyte (CTL) and do not substantially enhance T cell types that can be pro-tumor, and which include, but are not limited to, Tregs, CD4+ and/or CD8+ T cells expressing one or more checkpoint inhibitory receptors, Th2 cells and Th17 cells. Checkpoint inhibitory receptors refers to receptors (e.g., CTLA-4, B7-H3, B7-H4, TIM-3) expressed on immune cells that prevent or inhibit uncontrolled immune responses. For instance, the present expression vectors do not substantially enhance FOXP3+ regulatory T cells. In some embodiments, this selective CD8 T cell enhancement is in contrast to the non-specific T cell enhancement observed with a combination therapy of a gp-96 fusion and an antibody against a T cell costimulatory molecule.

For example, a vector can encode an agonist of OX40 (e.g., an OX40 ligand-Ig (OX40L-Ig) fusion, or a fragment thereof that binds OX40), an agonist of inducible T-cell costimulator (ICOS) (e.g., an ICOS ligand-Ig (ICOSL-Ig) fusion, or a fragment thereof that binds ICOS), an agonist of CD40 (e.g., a CD40L-Ig fusion protein, or fragment thereof), an agonist of CD27 (e.g., a CD70-Ig fusion protein or fragment thereof), or an agonist of 4-1BB (e.g., a 4-1BB ligand-Ig (4-1BBL-Ig) fusion, or a fragment thereof that binds 4-1BB). In some embodiments, a vector can encode an agonist of TNFRSF25 (e.g., a TL1A-Ig fusion, or a fragment thereof that binds TNFRSF25), or an agonist of glucocorticoid-induced tumor necrosis factor receptor (GITR) (e.g., a GITR ligand-Ig (GITRL-Ig) fusion, or a fragment thereof that binds GITR), or an agonist of CD40 (e.g., a CD40 ligand-Ig (CD40L-Ig) fusion, or a fragment thereof that binds CD40); or an agonist of CD27 (e.g., a CD27 ligand-Ig (e.g., CD70L-Ig) fusion, or a fragment thereof that binds CD40).

ICOS is an inducible T cell costimulatory receptor molecule that displays some homology to CD28 and CTLA-4, and interacts with B7-H2 expressed on the surface of antigen-presenting cells. ICOS has been implicated in the regulation of cell-mediated and humoral immune responses.

4-1BB is a type 2 transmembrane glycoprotein belonging to the TNF superfamily, and is expressed on activated T Lymphocytes.

OX40 (also referred to as CD134 or TNFRSF4) is a T cell costimulatory molecule that is engaged by OX40L, and frequently is induced in antigen presenting cells and other cell types. OX40 is known to enhance cytokine expression and survival of effector T cells.

GITR (TNFRSF18) is a T cell costimulatory molecule that is engaged by GITRL and is preferentially expressed in FoxP3+ regulatory T cells. GITR plays a significant role in the maintenance and function of Treg within the tumor microenvironment.

TNFRSF25 is a T cell costimulatory molecule that is preferentially expressed in CD4+ and CD8+ T cells following antigen stimulation. Signaling through TNFRSF25 is provided by TL1A, and functions to enhance T cell sensitivity to IL-2 receptor mediated proliferation in a cognate antigen dependent manner.

CD40 is a costimulatory protein found on various antigen presenting cells which plays a role in their activation. The binding of CD40L (CD154) on $T_H$ cells to CD40 activates antigen presenting cells and induces a variety of downstream effects.

CD27 a T cell costimulatory molecule belonging to the TNF superfamily which plays a role in the generation and long-term maintenance of T cell immunity. It binds to a ligand CD70 in various immunological processes.

Additional costimulatory molecules that may be utilized in the present invention include, but are not limited to, HVEM, CD28, CD30, CD30L, CD40, CD70, LIGHT (CD258), B7-1, and B7-2.

As for the gp96-Ig fusions, the Ig portion ("tag") of the T cell costimulatory fusion protein can contain, a non-variable portion of an immunoglobulin molecule (e.g., an IgG1, IgG2, IgG3, IgG4, IgM, IgA, or IgE molecule). As described above, such portions typically contain at least functional CH2 and CH3 domains of the constant region of an immunoglobulin heavy chain. In some embodiments, a T cell costimulatory peptide can be fused to the hinge, CH2 and CH3 domains of murine IgG1 (Bowen et al., *J Immunol* 1996, 156:442-449). The Ig tag can be from a mammalian (e.g., human, mouse, monkey, or rat) immunoglobulin, but human immunoglobulin can be particularly useful when the fusion protein is intended for in vivo use for humans. Again, DNAs encoding immunoglobulin light or heavy chain constant regions are known or readily available from cDNA libraries. Various leader sequences as described above also can be used for secretion of T cell costimulatory fusion proteins from bacterial and mammalian cells.

A representative nucleotide optimized sequence (SEQ ID NO:4) encoding the extracellular domain of human ICOSL fused to Ig, and the amino acid sequence of the encoded fusion (SEQ ID NO:5) are provided:

(SEQ ID NO: 4)
ATGAGACTGGGAAGCCCTGGCCTGCTGTTTCTGCTGTTCAGCAGCCTGAG

AGCCGACACCCAGGAAAAAGAAGTGCGGGCCATGGTGGGAAGCGACGTGG

AACTGAGCTGCGCCTGTCCTGAGGGCAGCAGATTCGACCTGAACGACGTG

TACGTGTACTGGCAGACCAGCGAGAGCAAGACCGTCGTGACCTACCACAT

CCCCCAGAACAGCTCCCTGGAAAACGTGGACAGCCGGTACAGAAAACCGG

GCCCTGATGTCTCCTGCCGGCATGCTGAGAGGCGACTTCAGCCTGCGGCT

GTTCAACGTGACCCCCCAGGACGAGCAGAAATTCCACTGCCTGGTGCTGA

GCCAGAGCCTGGGCTTCCAGGAAGTGCTGAGCGTGGAAGTGACCCTGCAC

GTGGCCGCCAATTTCAGCGTGCCAGTGGTGTCTGCCCCCCACAGCCCTTC

TCAGGATGAGCTGACCTTCACCTGTACCAGCATCAACGGCTACCCCAGAC

CCAATGTGTACTGGATCAACAAGACCGACAACAGCCTGCTGGACCAGGCC

CTGCAGAACGATACCGTGTTCCTGAACATGCGGGGCCTGTACGACGTGGT

GTCCGTGCTGAGAATCGCCAGAACCCCCAGCGTGAACATCGGCTGCTGCA

TCGAGAACGTGCTGCTGCAGCAGAACCTGACCGTGGGCAGCCAGACCGGC

AACGACATCGGCGAGAGAGACAAGATCACCGAGAACCCCGTGTCCACCGG

CGAGAAGAATGCCGCCACCTCTAAGTACGCCCTCCCTGCCCTTCTTGCC

CAGCCCCTGAATTTCTGGGCGGACCCTCCGTGTTTCTGTTCCCCCCAAAG

CCCAAGGACACCCTGATGATCAGCCGGACCCCCGAAGTGACCTGCGTGGT

GGTGGATGTGTCCCAGGAAGATCCCGAGGTGCAGTTCAATTGGTACGTGG

ACGGGGTGGAAGTGCACAACGCCAAGACCAAGCCCAGAGAGGAACAGTTC

AACAGCACCTACCGGGTGGTGTCTGTGCTGACCGTGCTGCACCAGGATTG

GCTGAGCGGCAAAGAGTACAAGTGCAAGGTGTCCAGCAAGGGCCTGCCCA

GCAGCATCGAAAAGACCATCAGCAACGCCACCGGCCAGCCCAGGGAACCC

CAGGTGTACACACTGCCCCCTAGCCAGGAAGAGATGACCAAGAACCAGGT

GTCCCTGACCTGTCTCGTGAAGGGCTTCTACCCCTCCGATATCGCCGTGG

AATGGGAGAGCAACGGCCAGCCAGAGAACAACTACAAGACCACCCCCCCA

GTGCTGGACAGCGACGGCTCATTCTTCCTGTACTCCCGGCTGACAGTGGA

CAAGAGCAGCTGGCAGGAAGGCAACGTGTTCAGCTGCAGCGTGATGCACG

AAGCCCTGCACAACCACTACACCCAGAAGTCCCTGTCTCTGTCCCTGGGC

AAATGA (SEQ ID NO: 5)
MRLGSPGLLFLLFSSLRADTQEKEVRAMVGSDVELSCACPEGSRFDLNDV

YVYWQTSESKTVVTYHIPQNSSLENVDSRYRNRALMSPAGMLRGDFSLRL

FNVTPQDEQKFHCLVLSQSLGFQEVLSVEVTLHVAANFSVPVVSAPHSPS

QDELTFTCTSINGYPRPNVYWINKTDNSLLDQALQNCTVFLNMRGLYDVV

SVLRIARTPSVNIGCCIENVLLQQNLTVGSQTGNDIGERDKITENPVSTG

EKNAATSKYGPPCPSCPAPEFLGGPSVFLFPPKPKDTLMISRTPEVTCVV

VDVSQEDPEVQFNWYVDGVEVHNAKTKPREEQFNSTYRVVSVLTVLHQDW

LSGKEYKCKVSSKGLPSSIEKTISNATGQPREPQVYTLPPSQEEMTKNQV

SLTCLVKGFYPSDIAVEWESNGQPENNYKTTPPVLDSDGSFFLYSRLTVD

KSSWQEGNVFSCSVMHEALHNHYTQKSLSLSLGK.

A representative nucleotide optimized sequence (SEQ ID NO:6) encoding the extracellular domain of human 4-1BBL fused to Ig, and the encoded amino acid sequence (SEQ ID NO:7) are provided:

(SEQ ID NO: 6)
ATGTCTAAGTACGGCCCTCCCTGCCCTAGCTGCCCTGCCCCTGAATTTCT

GGGCGGACCCAGCGTGTTCCTGTTCCCCCCAAAGCCCAAGGACACCCTGA

TGATCAGCCGGACCCCCGAAGTGACCTGCGTGGTGGTGGATGTGTCCCAG

GAAGATCCCGAGGTGCAGTTCAATTGGTACGTGGACGGCGTGGAAGTGCA

CAACGCCAAGACCAAGCCCAGAGAGGAACAGTTCAACAGCACCTACCGGG

TGGTGTCCGTGCTGACCGTGCTGCACCAGGATTGGCTGAGCGGCAAAGAG

TACAAGTGCAAGGTGTCCAGCAAGGGCCTGCCCAGCAGCATCGAGAAAAC

CATCAGCAACGCCACCGGCCAGCCCAGGGAACCCCAGGTGTACACACTGC

CCCCTAGCCAGGAAGAGATGACCAAGAACCAGGTGTCCCTGACCTGTCTC

GTGAAGGGCTTCTACCCCTCCGATATCGCCGTGGAATGGGAGAGCAACGG

CCAGCCTGAGAACAACTACAAGACCACCCCCCAGTGCTGGACAGCGACG

GCTCATTCTTCCTGTACAGCAGACTGACCGTGGAGAAGAGCAGCTGGCAG

GAAGGCAACGTGTTCAGCTGCAGCGTGATGCACGAGGCCCTGCACAACCA

CTACACCCAGAAGTCCCTGTCTCTGAGCCTGGGCAAGGCCTGTCCATGGG

CTGTGTCTGGCGCTAGAGCCTCTCCTGGATCTGCCGCCAGCCCCAGACTG

AGAGAGGGACCTGAGCTGAGCCCCGATGATCCTGCCGGACTGCTGGATCT

GAGACAGGGCATGTTCGCCCAGCTGGTGGCCCAGAACGTGCTGCTGATCG

ATGGCCCCTGAGCTGGTACAGCGATCCTGGACTGGCTGGCGTGTCACTG

ACAGGCGGCCTGAGCTACAAAGAGGACACCAAAGAACTGGTGGTGGCCAA

GGCCGGCGTGTACTACGTGTTCTTTCAGCTGGAACTGCGGAGAGTGGTGG

CCGGCGAAGGATCCGGCTCTGTGTCTCTGGCTCTGCATCTGCAGCCCCTG

AGATCTGCTGCTGGCGCTGCTGCTCTGGCCCTGACAGTGGACCTGCCTCC

TGCCTCTAGCGAGGCCAGAAACAGCGCATTCGGGTTTCAAGGCAGACTGC

TGCACCTGTCTGCCGGCCAGAGACTGGGAGTGCATCTGCACACAGAGGCC

AGAGCCAGGCACGCCTGGCAGCTGACTCAGGGCGCTACAGTGCTGGGCCT

GTTCAGAGTGACCCCCGAGATTCCAGCCGGCCTGCCTAGCCCCAGATCCG

AATGA (SEQ ID NO: 7)
MSKYGPPCPSCPAPEFLGGPSVFLFPPKPKDTLMISRTPEVTCVVVDVSQ

EDPEVQFNWYVDGVEVHANKTKPREEQFNSTYRVVSVLTVLHQDWLSGKE

YKCKVSSKGLPSSIEKTISNATGCPREPQVYTLPPSQEEMTKNQVSLTCL

VKGFYPSDIAVEWESNGQPENNYKTTPPVLDSDGSFFLYSRLTVDKSSWQ

EGNVFSCSVMHEALHNHYTQKSLSLSLGKACPWAVSGARASPGSAASPRL

REGPELSPDDPAGLLDLRQGMFAQLVAQNVLLIDGPLSWYSDPGLAGVSL

TGGLSYKEDTKELVVAKAGVYYVFFQLELRRVVAGEGSGSVSLALHLQPL

RSAAGAAALALTVDLPPASSEARNSAFGFQGRLLHLSAGQRLGVHLHTEA

RARHAWQLTQGATVLGLFRVTPEIPAGLPSPRSE.

A representative nucleotide optimized sequence (SEQ ID NO:8) encoding the extracellular domain of human TL1A fused to Ig, and the encoded amino acid sequence (SEQ ID NO:9) are provided:

(SEQ ID NO: 8)
ATGTCTAAGTACGGCCCTCCCTGCCCTAGCTGCCCTGCCCCTGAATTTCT
GGGCGGACCCAGCGTGTTCCTGTTCCCCCCAAAGCCCAAGGACACCCTGA
TGATCAGCCGGACCCCCGAAGTGACCTGCGTGGTGGTGGATGTGTCCCAG
GAAGATCCCGAGGTGCAGTTCAATTGGTACGTGGACGGCGTGGAAGTGCA
CAACGCGAAGACCAAGCCCAGAGAGGAACAGTTCAACAGCACCTACCGGG
TGGTGTCCGTGCTGACCGTGCTGCACCAGGATTGGCTGAGCGGCAAAGAG
TACAAGTGCAAGGTGTCCAGCAAGGGCCTGCCCAGCAGCATCGAGAAAAC
CATCAGCAACGCCACCGGCCAGCCCAGGGAACCCCAGGTGTACACACTGC
CCCCTAGCCAGGAAGAGATGACCAAGAACCAGGTGTCCCTGACCTGTCTC
GTGAAGGGCTTCTACCCCTCCGATATCGCCGTGGAATGGGAGAGCAACGG
CCAGCCTGAGAACAACTACAAGACCACCCCCCCAGTGCTGGACAGCGACG
GCTCATTCTTCCTGTACAGCAGACTGACCGTGGACAAGAGCAGCTGGCA
GGAAGGCAACGTGTTCAGCTGCAGCGTGATGCACGAGGCCCTGCACAACC
ACTACACCCAGAAGTCCCTGTCTCTGAGCCTGGGCAAGATCGAGGGCCGG
ATGGATAGAGCCCAGGGCGAAGCCTGCGTGCAGTTCCAGGCTCTGAAGGG
CCAGGAATTCGCCCCCAGCCACCAGCAGGTGTACGCCCCTCTGAGAGCCG
ACGGCGATAAGCCTAGAGCCCACCTGACAGTCGTGCGGCAGACCCCTACC
CAGCACTTCAAGAATCAGTTCCCCGCCCTGCACTGGGAGCACGAACTGGG
CCTGGCCTTCACCAAGAACAGAATGAACTACACCAACAAGTTTCTGCTGA
TCCCCGAGAGCGGCGACTACTTCATCTACAGCCAAGTGACCTTCCGGGGC
ATGACCAGCGAGTGCAGCGAGATCAGACAGGCCGGCAGACCTAACAAGCC
CGACAGCATCACCGTCGTGATCACCAAAGTGACCGACAGCTACCCCGAGC
CCACCCAGCTGCTGATGGGCACCAAGAGCGTGTGCGAAGTGGGCAGCAAC
TGGTTCCAGCCCATCTACCTGGGCGCCATGTTTAGTCTGCAAGAGGGCGA
CAAGCTGATGGTCAACGTGTCCGACATCAGCCTGGTGGATTACACCAAAG
AGGACAAGACCTTCTTCGGCGCCTTTCTGCTCTGA.

(SEQ ID NO: 9)
MSKYGPPCPSCPAPEFLGGPSVFLFPPKPKDTLMISRTPEVTCVVVDVSQ
EDPEVQFNWYVDGVEVHNAKTKPREEQFNSTYRVVSVLTVLHQDWLSGKE
YKCKVSSKGLPSSIEKTISNATGQPREPQVYTLPPSQEEMTKNQVSLTCL
VKGFYPSDIAVEWESNGQPENNYKTTPPVLDSDGSFFLYSRLTVDKSSWQ
EGNVFSCSVMHEALHNHYTQKSLSLSLGKIEGRMDRAQGEACVQFQALKG
QEFAPSHQQVYAPLRADGDKPRAHLTVVRQTPTQHFKNQFPALHWEHELG
LAFTKNRMNYTNKFLLIPESGDYFIYSQVTFRGMTSECSEIRQAGRPNKP
DSITVVITKVTDSYPEPTQLLMGTKSVCEVGSNWFQPIYLGAMFSLQEGD
KLMVNVSDSLVDYTKEDKTFFGAFLL,

A representative nucleotide optimized sequence (SEQ ID NO:10) encoding human OX40L-Ig, and the encoded amino acid sequence (SEQ ID NO:11) are provided:

(SEQ ID NO: 10)
ATGTCTAAGTACGGCCCTCCCTGCCCTAGCTGCCCTGCCCCTGAATTTCT
GGGCGGACCCAGCGTGTTCCTGTTCCCCCCAAAGCCCAAGGACACCCTGA
TGATCAGCCGGACCCCCGAAGTGACCTGCGTGGTGGTGGATGTGTCCCAG
GAAGATCCCGAGGTGCAGTTCAATTGGTACGTGGACGGCGTGGAAGTGCA
CAACGCCAAGACCAAGCCCAGAGAGGAACAGTTCAACAGCACCTACCGGG
TGGTGTCCGTGCTGACCGTGCTGCACCAGGATTGGCTGAGCGGCAAAGAG
TACAAGTGCAAGGTGTCCAGCAAGGGCCTGCCCAGCAGCATCGAGAAAAC
CATCAGCAACGCCACCGGCCAGCCCAGGGAACCCCAGGTGTACACACTGC
CCCCTAGCCAGGAGAGATGACCAAGAACCAGGTGTCCCTGACCTGTCTCG
TGAAGGGCTTCTACCCCTCCGATATCGCCGTGGAATGGGAGAGCAACGGC
CAGCCTGAGAACAACTACAAGACCACCCCCCCAGTGCTGGACAGCGACGG
CTCATTCTTCCTGTACAGCAGACTGACCGTGGACAAGAGCAGCTGGCAGG
AAGGCAACGTGTTCAGCTGCAGCGTGATGCACGAGGCCCTGCACAACCAC
TACACCCAGAAGTCCCTGTCTCTGAGCCTGGGCAAGATCGAGGGCCGGAT
GGATCAGGTGTCACACAGATACCCCGGATCCAGAGCATCAAAGTGCAGT
TTACCGAGTACAAGAAAGAGAAGGGCTTTATCCTGACCAGCCAGAAAGAG
GACGAGATCATGAAGGTGCAGAACAACAGCGTGATCATCAACTGCGACGG
GTTCTACCTGATCAGCCTGAAGGGCTACTTCAGTCAGGAAGTGAACATCA
GCCTGCACTACCAGAAGGACGAGGAACCCCTGTTCCAGCTGAAGAAAGTG
CGGAGCGTGAACAGCCTGATGGTGGCCTCTCTGACCTACAAGGACAAGGT
GTACCTGAACGTGACCACCGACAACACCAGCCTGGACGACTTCCACGTGA
ACGGCGGCGAGCTGATCCTGATTCACCAGAACCCCGGCGAGTTCTGCGTG
CTGTGA.

(SEQ ID NO: 11)
MSKYGPPCPSCPAPEFLGGPSVFLFPPKPKDTLMISRTPEVTCVVVDVSQ
EDPEVQFNWYVDGVEVHNAKTKPREEQFNSTYRVVSVLTVLHQDWLSGKE
YKCKVSSKGLPSSIEKTISNATGQPREPQVYTLPPSQEEMTKNQVSLTCL
VKGFYPSDIAVEWESNGQPENNYKTTPPVLDSDGSFFLYSRLTVDKSSWQ
EGNVFSCSVMHEALHNHYTQKSLSLSLGKIEGRMDQVSHRYPRIQSIKVQ
FTEYKKEKGFILTSQKEDEIMKVQNNSVIINCDGFYLISLKGYFSQEVNI
SLHYQKDEEPLFQLKKVRSVNSLMVASLTYKDKVYLNVTTDNTSLDDFHV
NGGELILIHQNPGEFCVL.

Representative nucleotide and amino acid sequences for human TL1A are set forth in SEQ ID NO:12 and SEQ ID NO:13, respectively:

(SEQ ID NO: 12)
TCCCAAGTAGCTGGGACTACAGGAGCCCACCACCACCCCCGGCTAATTTT
TTGTATTTTTAGTAGAGACGGGGTTTCACCGTGTTAGCCAAGATGGTCTT
GATCACCTGACCTCGTGATCCACCCGCCTTGGCCTCCCAAAGTGCTGGGA
TTACAGGCATGAGCCACCGCGCCCGGCCTCCATTCAAGTCTTTATTGAAT
ATCTGCTATGTTCTACACACTGTTCTAGGTGCTGGGGATGCAACAGGGGA

-continued

```
CAAAATAGGCAAAATCCCTGTCCTTTTGGGGTTGACATTCTAGTGACTCT
TCATGTAGTCTAGAAGAAGCTCAGTGAATAGTGTCTGTGGTTGTTACCAG
GGACACAATGACAGGAACATTCTTGGGTAGAGTGAGAGGCCTGGGGAGGG
AAGGGTCTCTAGGATGGAGCAGATGCTGGGCAGTCTTAGGGAGCCCCTCC
TGGCATGCACCCCCTCATCCCTCAGGCCACCCCCGTCCCTTGCAGGAGCA
CCCTGGGGAGCTGTCCAGAGCGCTGTGCCGCTGTCTGTGGCTGGAGGCAG
AGTAGGTGGTGTGCTGGGAATGCGAGTGGGAGAACTGGGATGGACCGAGG
GGAGGCGGGTGAGGAGGGGGCAACCACCCAACACCCACCAGCTGCTTTC
AGTGTTCTGGGTCCAGGTGCTCCTGGCTGGCCTTGTGGTCCCCCTCCTGC
TTGGGGCCACCCTGACCTACACATACCGCCACTGCTGGCCTCACAAGCCC
CTGGTTACTGCAGATGAAGCTGGGATGGAGGCTCTGACCCCACCACCGGC
CACCCATCTGTCACCCTTGGACAGCGCCCACACCCTTCTAGCACCTCCTG
ACAGCAGTGAGAAGATCTGCACCGTCCAGTTGGTGGGTAACAGCTGGACC
CCTGGCTACCCCGAGACCCAGGAGGCGCTCTGCCCGCAGGTGACATGGTC
CTGGGACCAGTTGCCCAGCAGAGCTCTTGGCCCCGCTGCTGCGCCCACAC
TCTCGCCAGAGTCCCCAGCCGGCTCGCCAGCCATGATGCTGCAGCCGGGC
CCGCAGCTCTACGACGTGATGGACGCGGTCCCAGCGCGGCGCTGGAAGGA
GTTCGTGCGCACGCTGGGGCTGCGCGAGGCAGAGATCGAAGCCGTGGAGG
TGGAGATCGGCCGCTTCCGAGACCAGCAGTACGAGATGCTCAAGCGCTGG
CGCCAGCAGCAGCCCGCGGGCCTCGGAGCCGTTTACGCGGCCCTGGAGCG
CATGGGGCTGGACGGCTGCGTGGAAGACTTGCGCAGCCGCCTGCAGCGCG
GCCCGTGACACGGCGCCCACTTGCCACCTAGGCGCTCTGGTGGCCCTTGC
AGAAGCCCTAAGTACGGTTACTTATGCGTGTAGACATTTTATGTCACTTA
TTAAGCCGCTGGCACGGCCCTGCGTAGCAGCACCAGCCGGCCCCACCCCT
GCTCGCCCCTATCGCTCCAGCCAAGGCGAAGAAGCACGAACGAATGTCGA
GAGGGGGTGAAGACATTTCTCAACTTCTCGGCCGGAGTTTGGCTGAGATC
GCGGTATTAAATCTGTGAAAGAAAACAAAACAAAACAA.
```

(SEQ ID NO: 13)
MEQRPRGCAAVAAALLLVLLGARAQGGTRSPRCDCAGDFHKKIGLFCCRG
CPAGHYLKAPCTEPCGNSTCLVCPQDTFLAWENHHNSECARCQACDEQAS
QVALENCSAVADTRCGCKPGWFVECQVSQCVSSSPFYCQPCLDCGALHRH
TRLLCSRRDTDCGTCLPGFYEHGDGCVSCPTPPPSLAGAPWGAVQSAVPL
SVAGGRVGVFWVQVLLAGLVVPLLLGATLTYTYRHCWPHKPLVTADEAGM
EALTPPPATHLSPLDSAHTLLAPPDSSEKICTVQLVGNSWTPGYPETQEA
LCPQVTWSWDQLPSRALGPAAAPTLSPESPAGSPAMMLQPGPQLYDVMDA
VPARRWKEFVRTLGLREAEIEAVEVEIGRFRDQQYEMLKRWRQQQPAGLG
AVYAALERMGLDGCVEDLRSRLQRGP.

Representative nucleotide and amino acid sequences for human HVEM are set forth in SEQ ID NO:38 (accession no. CR456909) and SEQ ID NO:39, respectively (accession no. CR456909):

(SEQ ID NO: 38)
```
ATGGAGCCTCCTGGAGACTGGGGGCCTCCTCCCTGGAGATCCACCCCCAA
AACCGACGTCTTGAGGCTGGTGCTGTATCTCACCTTCCTGGGAGCCCCCT
GCTACGCCCCAGCTCTGCCGTCCTGCAAGGAGGACGAGTACCCAGTGGGC
TCCGAGTGCTGCCCCAAGTGCAGTCCAGGTTATCGTGTGAAGGAGGCCTG
CGGGGAGCTGACGGGCACAGTGTGTGAACCCTGCCCTCCAGGCACCTACA
TTGCCCACCTCAATGGCCTAAGCAAGTGTCTGCAGTGCCAAATGTGTGAC
CCAGCCATGGGCCTGCGCGCGAGCCGGAACTGCTCCAGGACAGAGAACGC
CGTGTGTGGCTGCAGCCCAGGCCACTTCTGCATCGTCCAGGACGGGGACC
ACTGCGCCGCGTGCCGCGCTTACGCCACCTCCAGCCCGGGCCAGAGGGTG
CAGAAGGGAGGCACCGAGAGTCAGGACACCCTGTGTCAGAACTGCCCCCC
GGGGACCTTCTCTCCCAATGGGACCCTGGAGGAATGTCAGCACCAGACCA
AGTGCAGCTGGCTGGTGACGAAGGCCGGAGCTGGGACCAGCAGCTCCCAC
TGGGTATGGTGGTTTCTCTCAGGGAGCCTCGTCATCGTCATTGTTTGCTC
CACAGTTGGCCTAATCATATGTGTGAAAAGAAGAAAGCCAAGGGGTGATG
TAGTCAAGGTGATCGTCTCCGTCCAGCGGAAAAGACAGGAGGCAGAAGGT
GAGGCCACAGTCATTGAGGCCCTGCAGGCCCCTCCGGACGTCACCACGGT
GGCCGTGGAGGAGACAATACCCTATTCACGGGGAGGAGCCCAAACCATTA
A.
```

(SEQ ID NO: 39)
MEPPGDWGPPPWRSTPKTDVLRLVLYLTFLGAPCYAPALPSCKEDEYPVG
SECCPKCSPGYRVKEACGELTGTVCEPCPPGTYIAHLNGLSKCLQCQMCD
PAMGLRASRNCSRTENAVCGCSPGHFCIVQDGDHCAACRAYATSSPGQRV
QKGGTESQDTLCQNCPPGTFSPNGTLEECQHQTKCSWLVTKAGAGTSSSH
WVWWFLSGSLVIVIVCSTVGLIICVKRRKPRGDVVKVIVSVQRKRQEAEG
EATVIEALQAPPDVTTVAVEETIPSFTGRSPNH.

Representative nucleotide and amino acid sequences for human CD28 are set forth in SEQ ID NO:40 (accession no. NM_006139) and SEQ ID NO:41, respectively:

(SEQ ID NO: 40)
```
TAAAGTCATCAAAACAACGTTATATCCTGTGTGAAATGCTGCAGTCAGGA
TGCCTTGTGGTTTGAGTGCCTTGATCATGTGCCCTAAGGGGATGGTGGCG
GTGGTGGTGGCCGTGGATGACGGAGACTCTCAGGCCTTGGCAGGTGCGTC
TTTCAGTTCCCCTCACACTTCGGGTTCCTCGGGGAGGAGGGCTGGAACC
CTAGCCCATCGTCAGGACAAAGATGCTCAGGCTGCTCTTGGCTCTCAACT
TATTCCCTTCAATTCAAGTAACAGGAAACAAGATTTTGGTGAAGCAGTCG
CCCATGCTTGTAGCGTACGACAATGCGGTCAACCTTAGCTGCAAGTATTC
CTACAATCTCTTCTCAAGGGAGTTCCGGGCATCCCTTCACAAAGGACTGG
ATAGTGCTGTGGAAGTCTGTGTTGTATATGGGAATTACTCCCAGCAGCTT
```

-continued

CAGGTTTACTCAAAAACGGGGTTCAACTGTGATGGGAAATTGGGCAATGA
ATCAGTGACATTCTACCTCCAGAATTTGTATGTTAACCAAACAGATATTT
ACTTCTGCAAAATTGAAGTTATGTATCCTCCTCCTTACCTAGACAATGAG
AAGAGCAATGGAACCATTATCCATGTGAAAGGGAAACACCTTTGTCCAAG
TCCCCTATTTCCCGGACCTTCTAAGCCCTTTTGGGTGCTGGTGGTGGTTG
GTGGAGTCCTGGCTTGCTATAGCTTGCTAGTAACAGTGGCCTTTATTATT
TTCTGGGTGAGGAGTAAGAGGAGCAGGCTCCTGCACAGTGACTACATGAA
CATGACTCCCCGCCGCCCCGGGCCCACCCGCAAGCATTACCAGCCCTATG
CCCCACCACGCGACTTCGCAGCCTATCGCTCCTGACACGGACGCCTATCC
AGAAGCCAGCCGGCTGGCAGCCCCCATCTGCTCAATATCACTGCTCTGGA
TAGGAAATGACCGCCATCTCCAGCCGGCCACCTCAGGCCCCTGTTGGGCC
ACCAATGCCAATTTTTCTCGAGTGACTAGACCAAATATCAAGATCATTTT
GAGACTCTGAAATGAAGTAAAAGAGATTTCCTGTGACAGGCCAAGTCTTA
CAGTGCCATGGCCCACATTCCAACTTACCATGTACTTAGTGACTTGACTG
AGAAGTTAGGGTAGAAAACAAAAAGGGAGTGGATTCTGGGAGCCTCTTCC
CTTTCTCACTCACCTGCACATCTCAGTCAAGCAAAGTGTGGTATCCACAG
ACATTTTAGTTGCAGAAGAAAGGCTAGGAAATCATTCCTTTTGGTTAAAT
GGGTGTTTAATCTTTTGGTTAGTGGGTTAAACGGGGTAAGTTAGAGTAGG
GGGAGGGATAGGAAGACATATTTAAAAACCATTAAAACACTGTCTCCCAC
TCATGAAATGAGCCACGTAGTTCCTATTTAATGCTGTTTTCCTTTAGTTT
AGAAATACATAGACATTGTCTTTTATGAATTCTGATCATATTTAGTCATT
TTGACCAAATGAGGGATTTGGTCAAATGAGGGATTCCCTCAAAGCAATAT
CAGGTAAACCAAGTTGCTTTCCTCACTCCCTGTCATGAGACTTCAGTGTT
AATGTTCACAATATACTTTCGAAAGAATAAAATAGTTCTCCTACATGAAG
AAAGAATATGTCAGGAAATAAGGTCACTTTATGTCAAAATTATTTGAGTA
CTATGGGACCTGGCGCAGTGGCTCATGCTTGTAATCCCAGCACTTTGGGA
GGCCGAGGTGGGCAGATCACTTGAGATCAGGACCAGCCTGGTCAAGATGG
TGAAACTCCGTCTGTACTAAAAATACAAAATTTAGCTTGGCCTGGTGGCA
GGCACCTGTAATCCCAGCTGCCCAAGAGGCTGAGGCATGAGAATCGCTTG
AACCTGGCAGGCGGAGGTTGCAGTGAGCCGAGATAGTGCCACAGCTCTCC
AGCCTGGGCGACAGAGTGAGACTCCATCTCAAACAACAACAACAACAACA
ACAACAACAACAAACCACAAAATTATTTGAGTACTGTGAAGGATTATTTG
TCTAACAGTTCATTCCATCAGACCAGGTAGGAGCTTTCCTGTTTCATATG
TTTCAGGGTTGCACAGTTGGTCTCTTTAATGTCGGTGTGGAGATCCAAAG
TGGGTTGTGGAAAGAGCGTCCATAGGAGAAGTGAGAATACTGTGAAAAAG
GGATGTTAGCATTCATTAGAGTATGAGGATGAGTCCCAAGAAGGTTCTTT
GGAAGGAGGACGAATAGAATGGAGTAATGAAATTCTTGCCATGTGCTGAG
GAGATAGCCAGCATTAGGTGACAATCTTCCAGAAGTGGTCAGGCAGAAGG
TGCCCTGGTGAGAGCTCCTTTACAGGGACTTTATGTGGTTTAGGGCTCAG
GCTCCAAAACTCTGGGCTCAGCTGCTCCTGTACCTTGGAGGTCCATTCAC
ATGGGAAAGTATTTTGGAATGTGTCTTTTGAAGAGAGCATCAGAGTTCTT

-continued

AAGGGACTGGGTAAGGCCTGACCCTGAAATGACCATGGATATTTTCTAC
CTACAGTTTGAGTCAACTAGAATATGCCTGGGGACCTTGAAGAATGGCCC
TTCAGTGGCCCTCACCATTTGTTCATGCTTCAGTTAATTCAGGTGTTGAA
GGAGCTTAGGTTTTAGAGGCACGTAGACTTGGTTCAAGTCTCGTTAGTAG
TTGAATAGCCTCAGGCAAGTCACTGCCCACCTAAGATGATGGTTCTTCAA
CTATAAAATGGAGATAATGGTTACAAATGTCTCTTCCTATAGTATAATCT
CCATAAGGGCATGGCCCAAGTCTGTCTTTGACTCTGCCTATCCCTGACAT
TTAGTAGCATGCCCGACATACAATGTTAGCTATTGGTATTATTGCCATAT
AGATAAATTATGTATAAAAATTAAACTGGGCAATAGCCTAAGAAGGGGGG
AATATTGTAACACAAATTTAAACCCACTACGCAGGGATGAGGTGCTATAA
TATGAGGACCTTTTAACTTCCATCATTTTCCTGTTTCTTGAAATAGTTTA
TCTTGTAATGAAATATAAGGCACCTCCCACTTTTATGTATAGAAAGAGGT
CTTTTAATTTTTTTTAATGTGAGAAGGAAGGGAGGAGTAGGAATCTTGA
GATTCCAGATCGAAATACTGTACTTTGGTTGATTTTTAAGTGGGCTTCC
ATTCCATGGATTTAATCAGTCCCAAGAAGATCAAACTCAGCAGTACTTGG
GTGCTGAAGAACTGTTGGATTTACCCTGGCACGTGTGCCACTTGCCAGCT
TCTTGGGCACACAGAGTTCTTCAATCCAAGTTATCAGATTGTATTTGAAA
ATGACAGAGCTGGAGAGTTTTTTGAAATGGCAGTGGCAAATAAATAAATA
CTTTTTTTTAAATGGAAAGACTTGATCTATGGTAATAAATGATTTTGTTT
TCTGACTGGAAAAATAGGCCTACTAAAGATGAATCACACTTGAGATGTTT
CTTACTCACTCTGCACAGAAACAAAGAAGAAATGTTATACAGGGAAGTCC
GTTTTCACTATTAGTATGAACCAAGAAATGGTTCAAAAACAGTGGTAGGA
GCAATGCTTTCATAGTTTCAGATATGGTAGTTATGAAGAAAACAATGTCA
TTTGCTGCTATTATTGTAAGAGTCTTATAATTAATGGTACTCCTATAATT
TTTGATTGTGAGCTCACCTATTTGGGTTAAGCATGCCAATTTAAAGAGAC
CAAGTGTATGTACATTATGTTCTACATATTCAGTGATAAAATTACTAAAC
TACTATATGTCTGCTTTAAATTTGTACTTTAATATTGTCTTTTGGTATTA
AGAAAGATATGCTTTCAGAATAGATATGCTTCGCTTTGGCAAGGAATTTG
GATAGAACTTGCTATTTAAAGAGGTGTGGGTAAATCCTTGTATAAATC
TCCAGTTTAGCCTTTTTTGAAAAAGCTAGACTTTCAAATACTAATTTCAC
TTCAAGCAGGGTACGTTTCTGGTTTGTTTGCTTGACTTCAGTCACAATTT
CTTATCAGACCAATGGCTGACCTCTTTGAGATGTCAGGCTAGGCTTACCT
ATGTGTTCTGTGTCATGTGAATGCTGAGAAGTTTGACAGAGATCCAACTT
CAGCCTTGACCCCATCAGTCCCTCGGGTTAACTAACTGAGCCACCGGTCC
TCATGGCTATTTTAATGAGGGTATTGATGGTTAAATGCATGTCTGATCCC
TTATCCCAGCCATTTGCACTGCCAGCTGGGAACTATACCAGACCTGGATA
CTGATCCCAAAGTGTTAAATTCAACTACATGCTGGAGATTAGAGATGGTG
CCAATAAAGGACCCAGAACCAGGATCTTGATTGCTATAGACTTATTAATA
ATCCAGGTCAAAGAGAGTGACACACACTCTCTCAAGACCTGGGGTGAGGG
AGTCTGTGTTATCTGCAAGGCCATTTGAGGCTCAGAAAGTCTCTCTTTCC

-continued

```
TATAGATATATGCATACTTTCTGACATATAGGAATGTATCAGGAATACTC

AACCATCACAGGCATGTTCCTACCTCAGGGCCTTTACATGTCCTGTTTAC

TCTGTCTAGAATGTCCTTCTGTAGATGACCTGGCTTGCCTCGTCACCCTT

CAGGTCCTTGCTCAAGTGTCATCTTCTCCCCTAGTTAAACTACCCCACAC

CCTGTCTGCTTTCCTTGCTTATTTTTCTCCATAGCATTTTACCATCTCTT

ACATTAGACATTTTTCTTATTTATTTGTAGTTTATAAGCTTCATGAGGCA

AGTAACTTTGCTTTGTTTCTTGCTGTATCTCCAGTGCCCAGAGCAGTGCC

TGGTATATAATAAATATTTATTGACTGAGTGAAAAAAAAAAAAAAAAA.
```

(SEQ ID NO: 41)
```
MLRLLLALNLFPSIQVTGNKILVKQSPMLVAYDNAVNLSCKYSYNLFSRE

FRASLHKGLDSAVEVCVVYGNYSQQLQVYSKTGFNCDGKLGNESVTFYLQ

NLYVNQTDIYFCKIEVMYPPPYLDNEKSNGTIIHVKGKHLCPSPLFPGPS

KPFWVLVVVGGVLACYSLLVTVAFIIFWVRSKRSRLLHSDYMNMTPRRPG

PTRKHYQPYAPPRDFAAYRS.
```

Representative nucleotide and amino acid sequences for human CD30L are set forth in SEQ ID NO:42 (accession no. L09753) and SEQ ID NO:43, respectively:

(SEQ ID NO: 42)
```
CCAAGTCACATGATTCAGGATTCAGGGGGAGAATCCTTCTTGGAACAGAG

ATGGGCCCAGAACTGAATCAGATGAAGAGAGATAAGGTGTGATGTGGGGA

AGACTATATAAAGAATGGACCCAGGGCTGCAGCAAGCACTCAACGGAATG

GCCCCTCCTGGAGACACAGCCATGCATGTGCCGGCGGCTCCGTGGCCAG

CCACCTGGGGACCACGAGCCGCAGCTATTTCTATTTGACCACAGCCACTC

TGGCTCTGTGCCTTGTCTTCACGGTGGCCACTATTATGGTGTTGGTCGTT

CAGAGGACGGACTCCATTCCCAACTCACCTGACAACGTCCCCCTCAAAGG

AGGAAATTGCTCAGAAGACCTCTTATGTATCCTGAAAAGAGCTCCATTCA

AGAAGTCATGGGCCTACCTCCAAGTGGCAAAGCATCTAAACAAAACCAAG

TTGTCTTGGAACAAAGATGGCATTCTCCATGGAGTCAGATATCAGGATGG

GAATCTGGTGATCCAATTCCCTGGTTTGTACTTCATCATTTGCCAACTGC

AGTTTCTTGTACAATGCCCAAATAATTCTGTCGATCTGAAGTTGGAGCTT

CTCATCAACAAGCATATCAAAAAACAGGCCCTGGTGACAGTGTGTGAGTC

TGGAATGCAAACGAAACACGTATACCAGAATCTCTCTCAATTCTTGCTGG

ATTACCTGCAGGTCAACACCACCATATCAGTCAATGTGGATACATTCCAG

TACATAGATACAAGCACCTTTCCTCTTGAGAATGTGTTGTCCATCTTCTT

ATACAGTAATTCAGACTGAACAGTTTCTCTTGGCCTTCAGGAAGAAAGCG

CCTCTCTACCATACAGTATTTCATCCCTCCAAACACTTGGGCAAAAGAA

AACTTTAGACCAAGACAAACTACACAGGGTATTAAATAGTATACTTCTCC

TTCTGTCTCTTGGAAAGATACAGCTCCAGGGTTAAAAAGAGAGTTTTAG

TGAAGTATCTTTCAGATAGCAGGCAGGGAAGCAATGTAGTGTGGTGGGCA

GAGCCCCACACAGAATCAGAAGGGATGAATGGATGTCCCAGCCCAACCAC

TAATTCACTGTATGGTCTTGATCTATTTCTTCTGTTTTGAGAGCCTCCAG

TTAAAATGGGGCTTCAGTACCAGAGCAGCTAGCAACTCTGCCCTAATGGG

AAATGAAGGGGAGCTGGGTGTGAGTGTTTACACTGTGCCCTTCACGGGAT

ACTTCTTTTATCTGCAGATGGCCTAATGCTTAGTTGTCCAAGTCGCGATC

AAGGACTCTCTCACACAGGAAACTTCCCTATACTGGCAGATACACTTGTG

ACTGAACCATGCCCAGTTTATGCCTGTCTGACTGTCACTCTGGCACTAGG

AGGCTGATCTTGTACTCCATATGACCCCACCCCTAGGAACCCCCAGGGAA

AACCAGGCTCGGACAGCCCCCTGTTCCTGAGATGGAAAGCACAAATTTAA

TACACCACCACAATGGAAAACAAGTTCAAAGACTTTTACTTACAGATCCT

GGACAGAAAGGGCATAATGAGTCTGAAGGGCAGTCCTCCTTCTCCAGGTT

ACATGAGGCAGGAATAAGAAGTCAGACAGAGACAGCAAGACAGTTAACAA

CGTAGGTAAAGAAATAGGGTGTGGTCACTCTCAATCACTGGCAAATGCCT

GAATGGTCTGTCTGAAGGAAGCAACAGAGAAGTGGGGAATCCAGTCTGCT

AGGCAGGAAAGATGCCTCTAAGTTCTTGTCTCTGGCCAGAGGTGTGGTAT

AGAACCAGAAACCCATATCAAGGGTGACTAAGCCCGGCTTCCGGTATGAG

AAATTAAACTTGTATACAAAATGGTTGCCAAGGCAACATAAAATTATAAG

AATTC.
```

(SEQ ID NO: 43)
```
MDPGLQQALNGMAPPGDTAMHVPAGSVASHLGTTSRSYFYLTTATLALCL

VFTVATIMVLVVQRTDSIPNSPDNVPLKGGNCSEDLLCILKRAPFKKSWA

YLQVAKHLNKTKLSWNKDGILHGVRYQDGNLVICFPGLYFIICQLQFLVQ

CPNNSVDLKLELLINKHIKKQALVTVCESGMQTKHVYQNLSQFLLDYLQV

NTTISVNVDTFQYIDTSTFPLENVLSIFLYSNSD.
```

Representative nucleotide and amino acid sequences for human CD40 are set forth in SEQ ID NO:44 (accession no. NM_001250) and SEQ ID NO:45, respectively:

(SEQ ID NO: 44)
```
TTTCCTGGGCGGGGCCAAGGCTGGGGCAGGGGAGTCAGCAGAGGCCTCGC

TCGGGCGCCCAGTGGTCCTGCCGCCTGGTCTCACCTCGCTATGGTTCGTC

TGCCTCTGCAGTGCGTCCTCTGGGGCTGCTTGCTGACCGCTGTCCATCCA

GAACCACCCACTGCATGCAGAGAAAAACAGTACCTAATAAACAGTCAGTG

CTGTTCTTTGTGCCAGCCAGGACAGAAACTGGTGAGTGACTGCACAGAGT

TCACTGAAACGGAATGCCTTCCTTGCGGTGAAAGCGAATTCCTAGACACC

TGGAACAGAGAGACACACTGCCACCAGCACAAATACTGCGACCCCAACCT

AGGGCTTCGGGTCCAGCAGAAGGGCACCTCAGAAACAGACACCATCTGCA

CCTGTGAAGAAGGCTGGCACTGTACGAGTGAGGCCTGTGAGAGCTGTGTC

CTGCACCGCTCATGCTCGCCCGGCTTTGGGGTCAAGCAGATTGCTACAGG

GGTTTCTGATACCATCTGCGAGCCCTGCCCAGTCGGCTTCTTCTCCAATG

TGTCATCTGCTTTCGAAAAATGTCACCCTTGGACAAGCTGTGAGACCAAA

GACCTGGTTGTGCAACAGGCAGGCACAAACAAGACTGATGTTGTCTGTGG

TCCCCAGGATCGGCTGAGAGCCCTGGTGGTGATCCCCATCATCTTCGGGA

TCCTGTTTGCCATCCTCTTGGTGCTGGTCTTTATCAAAAAGGTGGCCAAG

AAGCCAACCAATAAGGCCCCCCACCCCAAGCAGGAACCCCAGGAGATCAA
```

TTTTCCCGACGATCTTCCTGGCTCCAACACTGCTGCTCCAGTGCAGGAGA
CTTTACATGGATGCCAACCGGTCACCCAGGAGGATGGCAAAGAGAGTCGC
ATCTCAGTGCAGGAGAGACAGTGAGGCTGCACCCACCCAGGAGTGTGGCC
ACGTGGGCAAACAGGCAGTTGGCCAGAGAGCCTGGTGCTGCTGCTGCTGT
GGCGTGAGGGTGAGGGGCTGGCACTGACTGGGCATAGCTCCCCGCTTCTG
CCTGCACCCCTGCAGTTTGAGACAGGAGACCTGGCACTGGATGCAGAAAC
AGTTCACCTTGAAGAACCTCTCACTTCACCCTGGAGCCCATCCAGTCTCC
CAACTTGTATTAAAGACAGAGGCAGAAGTTTGGTGGTGGTGGTGTTGGGG
TATGGTTTAGTAATATCCACCAGACCTTCCGATCCAGCAGTTTGGTGCCC
AGAGAGGCATCATGGTGGCTTCCCTGCGCCCAGGAAGCCATATACACAGA
TGCCCATTGCAGCATTGTTTGTGATAGTGAACAACTGGAAGCTGCTTAAC
TGTCCATCAGCAGGAGACTGGCTAAATAAAATTAGAATATATTTATACAA
CAGAATCTCAAAAACACTGTTGAGTAAGGAAAAAAAGGCATGCTGCTGAA
TGATGGGTATGGAACTTTTTAAAAAAGTACATGCTTTTATGTATGTATAT
TGCCTATGGATATATGTATAAATACAATATGCATCATATATTGATATAAC
AAGGGTTCTGGAAGGGTACACAGAAAACCCACAGCTCGAAGAGTGGTGAC
GTCTGGGGTGGGGAAGAAGGGTCTGGGGG (SEQ ID NO: 45)
MVRLPLQCVLWGCLLTAVHPEPPTACREKQYLINSQCCSLCQPGQKLVSC
DTEFTETECLPCGESEFLDTWNRETCHQKHYCDPNLGLRVQQKGTSETDT
ICTCEEGWHCTSEACESCVLHRSCSPGFGVKQIATGVSDTICEPCPVGFF
SNVSSAFEKCHPWTSCETKDLVVQQAGTNKTDVVCGPQDRLRALVVIPII
FGILFAILLVLVFIKKVAKKPTNKAPHPKQEPQEINFPDDLPGSNTAAPV
QETLHGCQPVTQEDGKESRISVQERQ.

Representative nucleotide and amino add sequences for human CD70 are set forth in SEQ ID NO:46 (accession no. NM_001252) and SEQ ID NO:47, respectively:

(SEQ ID NO: 46)
CCAGAGAGGGGCAGGCTGGTCCCCTGACAGGTTGAAGCAAGTAGACGCCC
AGGAGCCCGGGAGGGGGCTGCAGTTTCCTTCCTTCCTTCTCGGCAGCGC
TCCGCGCCCCCATCGCCCCTCCTGCGCTAGCGGAGGTGATCGCCGCGGCG
ATGCCGGAGGAGGGTTCGGGCTGCTCGGTGCGGCGCAGGCCCTATGGGTG
CGTCCTGCGGGCTGCTTTGGTCCCATTGGTCGCGGGCTTGGTGATCTGCC
TCGTGGTGTGCATCCAGCGCTTCGCACAGGCTCAGCAGCAGCTGCCGCTC
GAGTCACTTGGGTGGGACGTAGCTGAGCTGCAGCTGAATCACACAGGACC
TCAGCAGGACCCCAGGCTATACTGGCAGGGGGGCCCAGCACTGGGCGCT
CCTTCCTGCATGGACCAGAGCTGGACAAGGGGCAGCTACGTATCCATCGT
GATGGCATCTACATGGTACACATCCAGGTGACGCTGGCCATCTGCTCCTC
CACGACGGCCTCCAGGCACCACCCCACCACCCCTGGCCGTGGGAATCTGCT
CTCCCGCCTCCCGTAGCATCAGCCTGCTGCGTCTCAGCTTCCACCAAGGT
TGTACCATTGCCTCCCAGCGCCTGACGCCCCTGGCCCGAGGGGACACACT
CTGCACCAACCTCACTGGGACACTTTTGCCTTCCCGAAACACTGATGAGA
CCTTCTTTGGAGTGCAGTGGGTGCGCCCCTGACCACTGCTGCTGATTAGG
GTTTTTTAAATTTTATTTTATTTTATTTAAGTTCAAGAGAAAAAGTGTAC
ACACAGGGGCCACCCGGGGTTGGGGTGGGAGTGTGGTGGGGGGTAGTGGT
GGCAGGACAAGAGAAGGCATTGAGCTTTTTCTTTCATTTTCCTATTAAAA
AATACAAAAATCA.

(SEQ ID NO: 47)
MPEEGSGCSVRRRPYGCVLRAALVPLVAGLVICLVVCIQRFAQAQQQLPL
ESLGWDVAELQLNHTGPQQDPRLYWQGGPALGRSFLHGPELDKGQLRIHR
DGIYMVHIQVTLAICSSTTASRHHPTTLAVGICSPASRSISLLRLSFHQG
CTIASQRLTPLARGDTLCTNLTGTLLPSRNTDETFFGVQWVRP.

Representative nucleotide and amino acid sequences for human LIGHT are set forth in SEQ ID NO:48 (accession no. CR541854) and SEQ ID NO:49, respectively:

(SEQ ID NO: 48)
ATGGAGGAGAGTGTCGTACGGCCCTCAGTGTTTGTGGTGGATGGACAGAC
CGACATCCCATTCACGAGGCTGGGACGAAGCCACCGGAGACAGTCGTGCA
GTGTGGCCCGGGTGGGTCTGGGTCTCTTGCTGTTGCTGATGGGGGCCGGG
CTGGCCGTCCAAGGCTGGTTCCTCCTGCAGCTGCACTGGCGTCTAGGAGA
GATGGTCACCCGCCTGCCTGACGGACCTGCAGGCTCCTGGGAGCAGCTGA
TACAAGAGCGAAGGTCTCACGGAGGTCAACCCAGCAGCGCATCTCACAGG
GGCCAACTCCAGCTTGACCGGCAGCGGGGGCCGCTGTTATGGGAGACTC
AGCTGGGCCTGGCCTTCCTGAGGGCCCTCAGCTACCACGATGGGGCCCTT
GTGGTCACCAAAGCTGGCTACTACTACATCTACTCCAAGGTGCAGCTGGG
CGGTGTGGGCTGCCCGCTGGGCCTGGCCAGCACCATCACCCACGGCCTGT
ACAAGCGCACACCCCGCTACCCCGAGGAGCTGGAGCTGTTGGTCAGCCAG
CAGTCACCCTGCGGACGGGCCACCAGCAGCTCCCGGGTCTGGTGGGACAG
CAGCTTCCTGGGTGGTGTGGTACACCTGGAGGCTGGGGAGGAGGTGGTCG
TCCGTGTGCTGGATGAACGCCTGGTTCGACTGCGTGATGGTACCCGGTCT
TACTTCGGGGCTTTCATGGTGTGA.

(SEQ ID NO: 49)
MEESVVRPSVFVVDGQTDIPFTRLGRSHRRQSCSVARVGLGLLLLLMGAG
LAVQGWFLLQLHWRLGEMVTRLPDGPAGSWEQLIQERRSHEVNPAAHLTG
ANSSLTGSGGPLLWETQLGLAFLRGLSYHDGALVVTKAGYYYIYSKVQLG
GVGCPLGLASTITHGLYKRTPRYPEELELLVSQQSPCGRATSSSRVWWDS
SFLGGVVHLEAGEEVVVRVLDERLVRLRDGTRSYFGAFMV.

In various embodiments, the present invention provides for variants comprising any of the sequences described herein, for instance, a sequence having at least about 60%, or at least about 61%, or at least about 62%, or at least about 63%, or at least about 64%, or at least about 65%, or at least about 66%, or at least about 67%, or at least about 66%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99%) sequence identity with any of the sequences disclosed herein (for example, SEQ ID NOS: 1-13 and 38-49).

In various embodiments, the present invention provides for an amino acid sequence having one or more amino acid mutations relative any of the protein sequences described herein. In some embodiments, the one or more amino acid mutations may be independently selected from conservative or non-conservative substitutions, insertions, deletions, and truncations as described herein.

Checkpoint Blockade/Blockage of Tumor Immunosuppression

Some human tumors can be eliminated by a patient's immune system. For example, administration of a monoclonal antibody targeted to an immune "checkpoint" molecule can lead to complete response and tumor remission. A mode of action of such antibodies is through inhibition of an immune regulatory molecule that the tumors have co-opted as protection from an anti-tumor immune response. By inhibiting these "checkpoint" molecules (e.g., with an antagonistic antibody), a patient's CD8+ T cells may be allowed to proliferate and destroy tumor cells.

For example, administration of a monoclonal antibody targeted to by way of example, without limitation. CTLA-4 or PD-1 can lead to complete response and tumor remission. The mode of action of such antibodies is through inhibition of CTLA-4 or PD-1 that the tumors have co-opted as protection from an anti-tumor immune response. By inhibiting these "checkpoint" molecules (e.g., with an antagonistic antibody), a patient's CD8+ T cells may be allowed to proliferate and destroy tumor cells.

Thus, the vectors provided herein can be used in combination with one or more blocking antibodies targeted to an immune "checkpoint" molecule. For instance, in some embodiments, the vectors provided herein can be used in combination with one or more blocking antibodies targeted to a molecule such as CTLA-4 or PD-1. For example, the vectors provided herein may be used in combination with an agent that blocks, reduces and/or inhibits PD-1 and PD-L1 or PD-L2 and/or the binding of PD-1 with PD-L1 or PD-L2 (by way of non-limiting example, one or more of nivolumab (ONO-4538/BMS-936558, MDX1106, OPDIVO, BRISTOL MYERS SQUIBB), pembrolizumab (KEYTRUDA, Merck), pidilizumab (CT-011, CURE TECH), MK-3475 (MERCK), BMS 936559 (BRISTOL MYERS SQUIBB), MPDL328OA (ROCHE)). In an embodiment, the vectors provided herein may be used in combination with an agent that blocks, reduces and/or inhibits the activity of CTLA-4 and/or the binding of CTLA-4 with one or more receptors (e.g. CD80, CD86, AP2M1, SHP-2, and PPP2R5A). For instance, in some embodiments, the immune-modulating agent is an antibody such as, by way of non-limitation, ipilimumab (MDX-010, MDX-101, Yervoy, BMS) and/or tremelimumab (Pfizer). Blocking antibodies against these molecules can be obtained from, for example, Bristol Myers Squibb (New York, N.Y.), Merck (Kenilworth, N.J.), MedImmune (Gaithersburg, Md.), and Pfizer (New York, N.Y.).

Further, the vectors provided herein can be used in combination with one or more blocking antibodies targeted to an immune "checkpoint" molecule such as for example, BTLA, HVEM, TIM3, GAL9, LAG3, VISTA, KIR, 2B4, CD160 (also referred to as BY55), CGEN-15049, CHK 1 and CHK2 kinases, A2aR, CEACAM (e.g., CEACAM-1, CEACAM-3 and/or CEACAM-5), GITR, GITRL, galectin-9, CD244, CD160, TIGIT, SIRPα, ICOS, CD172a, and TMIGD2 and various B-7 family ligands (including, but are not limited to, B7-1, B7-2, B7-DC, B7-H1, B7-H2, B7-H3, B7-H4, B7-H5, B7-H6 and B7-H7).

Vectors and Host Cells

The present disclosure provides nucleic acid constructs that encode a vaccine protein fusion protein (e.g., a gp96-Ig fusion protein). Further, the present disclosure, provides nucleic acid constructs that encode a vaccine protein fusion protein (e.g., a gp96-Ig fusion protein), and a T cell costimulatory fusion protein that can be expressed in prokaryotic and eukaryotic cells. For example, the present disclosure provides expression vectors (e.g., DNA- or RNA-based vectors) containing nucleotide sequences that encode a vaccine protein fusion (e.g., a gp96-Ig fusion). For example, the present disclosure provides expression vectors (e.g., DNA- or RNA-based vectors) containing nucleotide sequences that encode a vaccine protein fusion (e.g., a gp96-Ig fusion), and a T cell costimulatory fusion protein (e.g., OX40L-Ig or a portion thereof that binds specifically to OX40, ICOSL-Ig or a portion thereof that binds specifically to ICOS, 4-1BBL-Ig, or a portion thereof that binds specifically to 4-1BBR, CD40L-Ig, or a portion thereof that binds specifically to CD40, CD70-Ig, or a portion thereof that binds specifically to CD27, TL1A-Ig or a portion thereof that binds specifically to TNFRSF25, or GITRL-Ig or a portion thereof that binds specifically to GITR). In addition, this document provides methods for making the vectors described herein, as well as methods for introducing the vectors into appropriate host cells for expression of the encoded polypeptides. In general, the methods provided herein include constructing nucleic acid sequences encoding a vaccine protein fusion protein (e.g., a gp96-Ig fusion protein) and a T cell costimulatory fusion protein, cloning the sequences encoding the fusion proteins into an expression vector. The expression vector can be introduced into host cells or incorporated into virus particles, either of which can be administered to a subject to, for example, treat cancer or infection. For example, gp96-Ig based vaccines can be generated to stimulate antigen specific immune responses against individual antigens expressed by simian immunodeficiency virus, human immunodeficiency virus, hepatitis C virus and malaria. Immune responses to these vaccines may be enhanced through co-expression of a T cell costimulatory fusion protein by the gp96-Ig vector.

cDNA or DNA sequences encoding a vaccine protein fusion (e.g., a gp96-Ig fusion) and a T cell costimulatory fusion protein can be obtained (and, if desired, modified) using conventional DNA cloning and mutagenesis methods, DNA amplification methods, and/or synthetic methods. In general, a sequence encoding a vaccine protein fusion protein (e.g., a gp96-Ig fusion protein) and/or a T cell costimulatory fusion protein can be inserted into a cloning vector for genetic modification and replication purposes prior to expression. Each coding sequence can be operably linked to a regulatory element, such as a promoter, for purposes of expressing the encoded protein in suitable host cells in vitro and in vivo.

Expression vectors can be introduced into host cells for producing secreted vaccine proteins (e.g., gp96-Ig) and T cell costimulatory fusion proteins. There are a variety of techniques available for introducing nucleic acids into viable cells. Techniques suitable for the transfer of nucleic acid into mammalian cells in vitro include the use of liposomes, electroporation, microinjection, cell fusion, polymer-based systems, DEAE-dextran, viral transduction, the calcium phosphate precipitation method, etc. For in vivo gene transfer, a number of techniques and reagents may also be used, including liposomes; natural polymer-based delivery vehicles, such as chitosan and gelatin; viral vectors are also suitable for in vivo transduction. In some situations it is desirable to provide a targeting agent, such as an antibody or ligand specific for a cell surface membrane protein. Where liposomes are employed, proteins which bind to a cell surface membrane protein associated with endocytosis may be used for targeting and/or to facilitate uptake, e.g., capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem. 262, 4429-4432 (1987); and Wagner et al., Proc. Natl. Acad. Sci. USA 87, 3410-3414 (1990).

Where appropriate, gene delivery agents such as, e.g., integration sequences can also be employed. Numerous integration sequences are known in the art (see, e.g., Nunes-Duby et al., Nucleic Acids Res. 26:391-406, 1998; Sadwoski, J. Bacteriol., 165:341-357, 1986; Bestor, Cell, 122 (3):322-325, 2005; Plasterk et al., TIG 15:326-332, 1999; Kootstra et al., Ann. Rev. Pharm. Toxicol., 43:413-439, 2003). These include recombinases and transposases. Examples include Cre (Sternberg and Hamilton, J. Mol. Biol., 150:467-486, 1981), lambda (Nash, Nature, 247, 543-545, 1974), Flp (Broach, et al., Cell, 29:227-234, 1982), R (Matsuzaki, et al., J. Bacteriology, 172:610-618, 1990). cpC31 (see, e.g., Groth et al., J. Mol. Bid. 335:667-678, 2004), sleeping beauty, transposases of the mariner family (Plasterk et al., supra), and components for integrating viruses such as AAV, retroviruses, and antiviruses having components that provide for virus integration such as the LTR sequences of retroviruses or lentivirus and the ITR sequences of AAV (Kootstra et al., Ann. Rev. Pharm. Toxicol., 43:413-439, 2003).

Cells may be cultured in vitro or genetically engineered, for example. Host cells can be obtained from normal or affected subjects, including healthy humans, cancer patients, and patients with an infectious disease, private laboratory deposits, public culture collections such as the American Type Culture Collection, or from commercial suppliers.

Cells that can be used for production and secretion of gp96-Ig fusion proteins and T cell costimulatory fusion proteins in vivo include, without limitation, epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, or granulocytes, various stem or progenitor cells, such as hematopoietic stem or progenitor cells (e.g., as obtained from bone marrow), umbilical cord blood, peripheral blood, fetal liver, etc., and tumor cells (e.g., human tumor cells). The choice of cell type depends on the type of tumor or infectious disease being treated or prevented, and can be determined by one of skill in the art.

Different host cells have characteristic and specific mechanisms for post-translational processing and modification of proteins. A host cell may be chosen which modifies and processes the expressed gene products in a specific fashion similar to the way the recipient processes its heat shock proteins (hsps). For the purpose of producing large amounts of gp96-Ig, it can be preferable that the type of host cell has been used for expression of heterologous genes, and is reasonably well characterized and developed for large-scale production processes. In some embodiments, the host cells are autologous to the patient to whom the present fusion or recombinant cells secreting the present fusion proteins are subsequently administered.

In some embodiments, an expression construct as provided herein can be introduced into an antigenic cell. As used herein, antigenic cells can include preoplastic cells that are infected with a cancer-causing infectious agent, such as a virus, but that are not yet neoplastic, or antigenic cells that have been exposed to a mutagen or cancer-causing agent, such as a DNA-damaging agent or radiation, for example. Other cells that can be used are preneoplastic cells that are in transition from a normal to a neoplastic form as characterized by morphology or physiological or biochemical function.

Typically, the cancer cells and preneoplastic cells used in the methods provided herein are of mammalian origin. Mammals contemplated include humans, companion animals (e.g., dogs and cats), livestock animals (e.g., sheep, cattle, goats, pigs and horses), laboratory animals (e.g., mice, rats and rabbits), and captive or free wild animals.

In some embodiments, cancer cells (e.g., human tumor cells) can be used in the methods described herein. The cancer cells provide antigenic peptides that become associated non-covalently with the expressed gp96-Ig fusion proteins. Cell lines derived from a preneoplastic lesion, cancer tissue, or cancer cells also can be used, provided that the cells of the cell line have at least one or more antigenic determinant in common with the antigens on the target cancer cells. Cancer tissues, cancer cells, cells infected with a cancer-causing agent, other preneoplastic cells, and cell lines of human origin can be used. Cancer cells excised from the patient to whom ultimately the fusion proteins ultimately are to be administered can be particularly useful, although allogeneic cells also can be used. In some embodiments, a cancer cell can be from an established tumor cell line such as, without limitation, an established non-small cell lung carcinoma (NSCLC), bladder cancer, melanoma, ovarian cancer, renal cell carcinoma, prostate carcinoma, sarcoma, breast carcinoma, squamous cell carcinoma, head and neck carcinoma, hepatocellular carcinoma, pancreatic carcinoma, or colon carcinoma cell line.

In various embodiments, the present fusion proteins allow for both the costimulation T cell and the presentation of various tumor cell antigens. For instance, in some embodiments, the present vaccine protein fusions (e.g., gp96 fusions) chaperone these various tumor antigens. In various embodiments, the tumor cells secrete a variety of antigens. Illustrative, but non-limiting, antigens that can be secreted are: MART-1/Melan-A, gp100, Dipeptidyl peptidase IV (DPPIV), adenosine deaminase-binding protein (ADAbp), cyclophilin b, Colorectal associated antigen (CRC)-0017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGEfamily of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin and γ-catenin, p120ctn, gp100 Pmel117, PRAME, NY-ESO-1, cdc27, adenomatous polyposis coli protein (APC), fodrin, Connexin 37, Ig-idiotype, p15, gp75, GM2 and GD2 gangliosides, viral products such as human papilloma virus proteins, Smad family of tumor antigens, Imp-1, NA, EBV-encoded nuclear antigen (EBNA)-1, brain glycogen phosphorylase, SSX-1, SSX-2 (HOM-MEL-40), SSX-1, SSX-4, SSX-5, SCP-1 CT-7, c-erbB-2, CD19, CD20, CD22, CD30, CD33, CD37, CD56, CD70, CD74, CD138, AGS 16, MUC1, GPNMB, Ep-CAM, PD-L1, PD-L2, PMSA, bladder cancer antigens such as ACTL8, ADAM22, ADAM23, ATAD2, ATAD2B, BIRC5, CASC5, CEP290, CEP55, CTAGE5, DCAF12, DDX5, FAM133A, IL13RA2, IMP3, KIAA0100, MAGEA11, MAGEA3, MAGEA6, MPHOSPH10, ODF2, ODF2L, OIP5, PBK, RQCD1, SPAG1, SPAG4, SPAG9, TMEFF1, TTK, and prostate cancer antigens such as PRAME, BIRC5, CEP55, ATAD2, ODF2, KIAA0100, SPAG9, GPATCH2, ATAD2B, CEP290, SPAG1, ODF2L, CTAGE5, DDX5, DCAF12, IMP3. In some embodiments, the antigens are human endogenous retroviral antigens. Illustrative antigens can also include antigens from human endogenous retroviruses which include, but are not limited to, epitopes derived from at least a portion of Gag, at least a portion of Tat, at least a portion of Rev, a least a portion of Nef, and at least a portion of gp160.

Further, in some embodiments, the present vaccine protein fusions (e.g., gp96 fusions) provide for an adjuvant effect that further allows the immune system of a patient, when used in the various methods described herein, to be activated against a disease of interest.

Both prokaryotic and eukaryotic vectors can be used for expression of the vaccine protein (e.g., gp96-Ig) and T cell costimulatory fusion proteins in the methods provided herein. Prokaryotic vectors include constructs based on *E. coli* sequences (see, e.g., Makrides, *Microbiol Rev* 1996, 60:512-538). Non-limiting examples of regulatory regions that can be used for expression in *E. coli* include lac, trp, lpp, phoA, recA, tac, T3, T7 and λP$_L$. Non-limiting examples of prokaryotic expression vectors may include the λgt vector series such as λgt11 (Huynh et al., in "DNA Cloning Techniques, Vol. I: A Practical Approach," 1984, (D. Glover, ed.), pp. 49-78, IRL Press, Oxford), and the pET vector series (Studier et al., *Methods Enzymol* 1990, 185:60-89). Prokaryotic host-vector systems cannot perform much of the post-translational processing of mammalian cells, however. Thus, eukaryotic host-vector systems may be particularly useful.

A variety of regulatory regions can be used for expression of the vaccine protein (e.g., gp96-Ig) and T cell costimulatory fusions in mammalian host cells. For example, the SV40 early and late promoters, the cytomegalovirus (CMV) immediate early promoter, and the Rous sarcoma virus long terminal repeat (RSV-LTR) promoter can be used. Inducible promoters that may be useful in mammalian cells include, without limitation, promoters associated with the metallothionein II gene, mouse mammary tumor virus glucocorticoid responsive long terminal repeats (MMTV-LTR), β-interferon gene, and the hsp70 gene (see, Williams et al., *Cancer Res* 1989, 49:2735-42; and Taylor et al., *Mol Cell Biol* 1990, 10:165-75). Heat shock promoters or stress promoters also may be advantageous for driving expression of the fusion proteins in recombinant host cells.

In an embodiment, the present invention contemplates the use of inducible promoters capable of effecting high level of expression transiently in response to a cue. Illustrative inducible expression control regions include those comprising an inducible promoter that is stimulated with a cue such as a small molecule chemical compound. Particular examples can be found, for example, in U.S. Pat. Nos. 5,989,910, 5,935,934, 6,015,709, and 6,004,941, each of which is incorporated herein by reference in its entirety.

Animal regulatory regions that exhibit tissue specificity and have been utilized in transgenic animals also can be used in tumor cells of a particular tissue type: the elastase I gene control region that is active in pancreatic acinar cells (Swift et al. *Cell* 1984, 38:639-646; Omitz et al., *Cold Spring Harbor Symp Quant Biol* 1986, 50:399-409; and MacDonald, *Hepatology* 1987, 7:425-515); the insulin gene control region that is active in pancreatic beta cells (Hanahan, *Nature* 1985, 315:115-122), the immunoglobulin gene control region that is active in lymphoid cells (Grosschedl et al., *Cell* 1984, 38:647-658; Adames et al., *Nature* 1985, 318: 533-538; and Alexander et al., *Mol Cell Biol* 1987, 7:1436-1444), the mouse mammary tumor virus control region that is active in testicular, breast, lymphoid and mast cells (Leder et al., *Cell* 1986, 45:485-495), the albumin gene control region that is active in liver (Pinkert et al., *Genes Devel,* 1987, 1:268-276), the alpha-fetoprotein gene control region that is active in liver (Krumlauf et al., *Mol Cell Biol* 1985, 5:1639-1648; and Hammer et al., *Science* 1987, 235:53-58); the alpha 1-antitrypsin gene control region that is active in liver (Kelsey et al., *Genes Devel* 1987, 1:161-171), the beta-globin gene control region that is active in myeloid cells (Mogram et al., *Nature* 1985, 315:338-340; and Kollias et al., *Cell* 1986, 46:89-94); the myelin basic protein gene control region that is active in oligodendrocyte cells in the brain (Readhead et al., *Cell* 1987, 48:703-712); the myosin light chain-2 gene control region that is active in skeletal muscle (Sani, *Nature* 1985, 314:283-286), and the gonadotropic releasing hormone gene control region that is active in the hypothalamus (Mason et al., *Science* 1986, 234:1372-1378).

An expression vector also can include transcription enhancer elements, such as those found in SV40 virus, Hepatitis B virus, cytomegalovirus, immunoglobulin genes, metallothionein, and β-actin (see, Bittner et al., *Meth Enzymol* 1987, 153:516-544; and Gorman, *Curr Op Biotechnol* 1990, 1:36-47). In addition, an expression vector can contain sequences that permit maintenance and replication of the vector in more than one type of host cell, or integration of the vector into the host chromosome. Such sequences include, without limitation, to replication origins, autonomously replicating sequences (ARS), centromere DNA, and telomere DNA.

In addition, an expression vector can contain one or more selectable or screenable marker genes for initially isolating, identifying, or tracking host cells that contain DNA encoding fusion proteins as described herein. For long term, high yield production of gp96-Ig and T cell costimulatory fusion proteins, stable expression in mammalian cells can be useful. A number of selection systems can be used for mammalian cells. For example, the Herpes simplex virus thymidine kinase (Wigler et al., *Cell* 1977, 11:223), hypoxanthine-guanine phosphoribosyltransferase (Szybalski and Szybalski, *Proc Natl Acad Sci USA* 1962, 48:2026), and adenine phosphoribosyltransferase (Lowy et al., *Cell* 1980, 22:817) genes can be employed in tk⁻, hgprt⁻, or aprt⁻ cells, respectively. In addition, antimetabolite resistance can be used as the basis of selection for dihydrofolate reductase (dhfr), which confers resistance to methotrexate (Wigler et al., *Proc Natl Acad Sci USA* 1980, 77:3567; O'Hare et al., *Proc Natl Acad Sci USA* 1981, 78:1527); gpt, which confers resistance to mycophenolic add (Mulligan and Berg, *Proc Natl Acad Sci USA* 1981, 78:2072); neomycin phosphotransferase (neo), which confers resistance to the aminoglycoside G-418 (Colberre-Garapin et al., *J Mol Biol* 1981, 150:1); and hygromycin phosphotransferase (hyg), which confers resistance to hygromycin (Santerre et al., *Gene* 1984, 30:147). Other selectable markers such as histidinol and Zeocin™ also can be used.

Useful mammalian host cells include, without limitation, cells derived from humans, monkeys, and rodents (see, for example, Kriegler in "Gene Transfer and Expression: A Laboratory Manual," 1990, New York, Freeman & Co.). These include monkey kidney cell lines transformed by SV40 (e.g., COS-7, ATCC CRL 1651); human embryonic kidney lines (e.g., 293, 293-EBNA, or 293 cells subcloned for growth in suspension culture, Graham et al., *J Gen Virol* 1977, 36:59); baby hamster kidney cells (e.g., BHK, ATCC CCL 10); Chinese hamster ovary-cells-DHFR (e.g., CHO, Urlaub and Chasin, *Proc Natl Acad Sci USA* 1980, 77:4216); mouse sertoli cells (Mather, *Biol Reprod* 1980, 23:243-251); mouse fibroblast cells (e.g., NIH-3T3), monkey kidney cells (e.g., CV1 ATCC CCL 70); African green monkey kidney cells, (e.g., VERO-76, ATCC CRL-1587); human cervical carcinoma cells (e.g., HELA, ATCC CCL 2); canine kidney cells (e.g., MDCK, ATCC CCL 34); buffalo rat liver cells (e.g., BRL 3A, ATCC CRL 1442); human lung cells (e.g., W138, ATCC CCL 75); human liver cells (e.g., Hep G2, HB 8065); and mouse mammary tumor cells (e.g., MMT 060562, ATCC CCL51). Illustrative cancer cell types for expressing the fusion proteins described herein include mouse fibroblast cell line, NIH3T3, mouse Lewis lung carcinoma cell line, LLC, mouse mastocytoma cell line, P815, mouse lymphoma cell line, EL4 and its ovalbumin transfectant, E.G7, mouse melanoma cell line, B16F10, mouse fibrosarcoma cell line, MC57, human small cell lung carcinoma cell lines, SCLC #2 and SCLC #7, human lung adenocarcinoma cell line, e.g., AD100, and human prostate cancer cell line, e.g., PC-3.

A number of viral-based expression systems also can be used with mammalian cells to produce gp96-Ig and T cell costimulatory fusion proteins. Vectors using DNA virus backbones have been derived from simian virus 40 (SV40) (Hamer et al., *Cell* 1979, 17:725), adenovirus (Van Doren et al., *Mol Cell Biol* 1984, 4:1653), adeno-associated virus (McLaughlin et al., *J Virol* 1988, 62:1963), and bovine papillomas virus (Zinn et al., *Proc Natl Acad Sci USA* 1982, 79:4897). When an adenovirus is used as an expression vector, the donor DNA sequence may be ligated to an adenovirus transcription/translation control complex, e.g., the late promoter and tripartite leader sequence. This fusion gene may then be inserted in the adenovirus genome by in vitro or in vivo recombination. Insertion in a non-essential region of the viral genome (e.g., region E1 or E3) can result in a recombinant virus that is viable and capable of expressing heterologous products in infected hosts. (See, e.g., Logan and Shenk, *Proc Natl Acad Sci USA* 1984, 81:3655-3659).

In some embodiments, an adenovirus expression vector comprising an effective amount of a composition that comprises a nucleotide sequence encoding a secretable vaccine protein (e.g., without limitation gp96-Ig) is used.

In some embodiments, the adenovirus expression vector comprises an effective amount of a composition that comprises a first nucleotide sequence encoding a secretable vaccine protein (e.g., without limitation gp96-Ig) and and a second nucleotide sequence encoding a T cell costimulatory fusion protein (e.g., without limitation OX40L-Ig, or a portion thereof that binds to OX40).

In some embodiments, the adenovirus expression vector comprises an effective amount of a composition that comprises a first nucleotide sequence encoding a secretable vaccine protein (e.g., without limitation gp96-Ig) and and a second nucleotide sequence encoding a T cell costimulatory fusion protein (e.g., without limitation OX40L-Ig, or a portion thereof that binds to OX40) and an effective amount of a biological cell comprising an adenovirus expression vector that comprises a first nucleotide sequence encoding a secretable vaccine protein (e.g., without limitation gp96-Ig), and a second nucleotide sequence encoding a T cell costimulatory fusion protein (e.g., without limitation OX40L-Ig, or a portion thereof that binds to OX40).

In some embodiments, the present invention provides a method for treating a tumor in a subject in need thereof, comprising administering to a subject in need thereof a combination therapy of (1) intratumorally delivery of an effective amount of a composition comprising an adenovirus expression vector that comprises a first nucleotide sequence encoding a secretable vaccine protein (e.g., without limitation gp96-Ig), and a second nucleotide sequence encoding a T cell costimulatory fusion protein (e.g., without limitation OX40L-Ig, or a portion thereof that binds to OX40) and (2) an effective amount of a biological cell comprising an adenovirus expression vector that comprises a first nucleotide sequence encoding a secretable vaccine protein (e.g., without limitation gp96-Ig), and a second nucleotide sequence encoding a T cell costimulatory fusion protein (e.g., without limitation OX40L-Ig, or a portion thereof that binds to OX40), wherein the T cell costimulatory fusion protein enhances activation of antigen-specific T cells when administered to the subject.

Bovine papillomavirus (BPV) can infect many higher vertebrates, inducing man, and its DNA replicates as an episome. A number of shuttle vectors have been developed for recombinant gene expression which exist as stable, multicopy (20-300 copies/cell) extrachromosomal elements in mammalian cells. Typically, these vectors contain a segment of BPV DNA (the entire genome or a 69% transforming fragment), a promoter with a broad host range, a polyadenylation signal, splice signals, a selectable marker, and "poisonless" plasmid sequences that allow the vector to be propagated in *E. coli*. Following construction and amplification in bacteria, the expression gene constructs are transfected into cultured mammalian cells by, for example, calcium phosphate coprecipitation. For those host cells that do not manifest a transformed phenotype, selection of transformants is achieved by use of a dominant selectable marker, such as histidinol and G418 resistance.

Alternatively, the vaccinia 7.5K promoter can be used. (See, e.g., Mackett et al., *Proc Natl Acad Sci USA* 1982, 79:7415-7419; Mackett et al., *J Virol* 1984, 49:857-864; and Panicali et al., *Proc Natl Acad Sci USA* 1982, 79:4927-4931.) In cases where a human host cell is used, vectors based on the Epstein-Barr virus (EBV) origin (OriP) and EBV nuclear antigen 1 (EBNA-1; a trans-acting replication factor) can be used. Such vectors can be used with a broad range of human host cells, e.g., EBO-pCD (Spickofsky et al., *DNA Prot Eng Tech* 1990, 2:14-18); pDR2 and λDR2 (available from Clontech Laboratories).

Gp96-Ig and T cell costimulatory fusion proteins also can be made with retrovirus-based expression systems. Retroviruses, such as Moloney murine leukemia virus, can be used since most of the viral gene sequence can be removed and replaced with exogenous coding sequence while the missing viral functions can be supplied in trans. In contrast to transfection, retroviruses can efficiently infect and transfer genes to a wide range of cell types including, for example, primary hematopoietic cells. Moreover, the host range for infection by a retroviral vector can be manipulated by the choice of envelope used for vector packaging.

For example, a retroviral vector can comprise a 5' long terminal repeat (LTR), a 3' LTR, a packaging signal, a bacterial origin of replication, and a selectable marker. The gp96-Ig fusion protein coding sequence, for example, can be inserted into a position between the 5' LTR and 3' LTR, such that transcription from the 5' LTR promoter transcribes the cloned DNA. The 5' LTR contains a promoter (e.g., an LTR promoter), an R region, a U5 region, and a primer binding site, in that order. Nucleotide sequences of these LTR elements are well known in the art. A heterologous promoter as well as multiple drug selection markers also can be included in the expression vector to facilitate selection of infected cells. See, McLauchlin et al., *Prog Nucleic Acid Res Mol Biol* 1990, 38:91-135; Morgenstern et al., *Nucleic Acid Res* 1990, 18:3587-3596; Choulika et al., *J Virol* 1996, 70:1792-1798; Boesen et al., *Biotherapy* 1994, 6:291-302; Salmons and Gunzberg, *Human Gene Ther* 1993, 4:129-141; and Grossman and Wilson, *Curr Opin Genet Devel* 1993, 3:110-114.

Any of the cloning and expression vectors described herein may be synthesized and assembled from known DNA sequences using techniques that are known in the art. The regulatory regions and enhancer elements can be of a variety of origins, both natural and synthetic. Some vectors and host cells may be obtained commercially. Non-limiting examples of useful vectors are described in Appendix 5 of *Current Protocols in Molecular Biology*. 1988, ed. Ausubel et al., Greene Publish. Assoc. & Wiley Interscience, which is incorporated herein by reference; and the catalogs of commercial suppliers such as Clontech Laboratories, Stratagene Inc., and Invitrogen, Inc.

Methods of Treating

An expression vector as provided herein can be incorporated into a composition for administration to a subject (e.g., a research animal or a mammal, such as a human, having a clinical condition such as cancer or an infection). For example, an expression vector can be administered to a subject for the treatment of cancer. Thus, this document provides methods for treating clinical conditions such as cancer with the expression vectors provided herein. The methods can include administering to a subject an expression vector, a cell containing the expression vector, or a virus or virus-like particle containing the expression vector, under conditions wherein the progression or a symptom of the clinical condition in the subject is reduced in a therapeutic manner.

As described herein, the expression vector(s) can be administered intratumorally to a subject. Optionally, the subject may further be administered a biological cell comprising the expression vectors).

In various embodiments, the present invention pertains to cancers and/or tumors; for example, the treatment or prevention of cancers anchor tumors. Cancers or tumors refer to an uncontrolled growth of cells and/or abnormal increased cell survival and/or inhibition of apoptosis which interferes with the normal functioning of the bodily organs and systems. Included are benign and malignant cancers, polyps, hyperplasia, as well as dormant tumors or micrometastases. Also, included are cells having abnormal proliferation that is not impeded by the immune system (e.g., virus infected cells). The cancer may be a primary cancer or a metastatic cancer. The primary cancer may be an area of cancer cells at an originating site that becomes clinically detectable, and may be a primary tumor. In contrast, the metastatic cancer may be the spread of a disease from one organ or part to another non-adjacent organ or part. The metastatic cancer may be caused by a cancer cell that acquires the ability to penetrate and infiltrate surrounding normal tissues in a local area, forming a new tumor, which may be a local metastasis. The cancer may also be caused by a cancer cell that acquires the ability to penetrate the walls of lymphatic and/or blood vessels, after which the cancer cell is able to circulate through the bloodstream (thereby being a circulating tumor cell) to other sites and tissues in the body. The cancer may be due to a process such as lymphatic or hematogeneous spread. The cancer may also be caused by a tumor cell that comes to rest at another site, re-penetrates through the vessel or walls, continues to multiply, and eventually forms another clinically detectable tumor. The cancer may be this new tumor, which may be a metastatic (or secondary) tumor.

The cancer may be caused by tumor cells that have metastasized, which may be a secondary or metastatic tumor. The cells of the tumor may be like those in the original tumor. As an example, if a breast cancer or colon cancer metastasizes to the liver, the secondary tumor, while present in the liver, is made up of abnormal breast or colon cells, not of abnormal liver cells. The tumor in the liver may thus be a metastatic breast cancer or a metastatic colon cancer, not liver cancer.

The cancer may have an origin from any tissue. The cancer may originate from melanoma, colon, breast, or prostate, and thus may be made up of cells that were originally skin, colon, breast, or prostate, respectively. The cancer may also be a hematological malignancy, which may be lymphoma. The cancer may invade a tissue such as liver, lung, bladder, or intestinal.

Illustrative cancers that may be treated include, but are not limited to, carcinomas, e.g., various subtypes, including, for example, adenocarcinoma, basal cell carcinoma, squamous cell carcinoma, and transitional cell carcinoma), sarcomas (including, for example, bone and soft tissue), leukemias (including, for example, acute myeloid, acute lymphoblastic, chronic myeloid, chronic lymphocytic, and hairy cell), lymphomas and myelomas (including, for example, Hodgkin and non-Hodgkin lymphomas, light chain, non-secretory, MGUS, and plasmacytomas), and central nervous system cancers (including, for example, brain (e.g., gliomas (e.g., astrocytoma, oligodendroglioma, and ependymoma), meningioma, pituitary adenoma, and neuromas, and spinal cord tumors (e.g., meningiomas and neurofibroma).

Representative cancers anchor tumors of the present invention include, but are not limited to, a basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer, esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer, prostate cancer; retinoblastoma; rhabdomyosarcoma; rectal cancer; cancer of the respiratory system; salivary gland carcinoma; sarcoma; skin cancer; squamous cell cancer; stomach cancer, testicular cancer; thyroid cancer; uterine or endometrial cancer; cancer of the urinary system; vulval cancer, lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (such as that associated with brain tumors), and Meigs' syndrome.

This document therefore also provides compositions containing a vector or a tumor cell or virus particle containing a vector encoding a secreted gp96-Ig fusion polypeptide and a T cell costimulatory fusion polypeptide as described herein, in combination with a physiologically and pharmaceutically acceptable carrier. The physiologically and pharmaceutically acceptable carrier can include any of the well-known components useful for immunization. The carrier can facilitate or enhance an immune response to an antigen administered in a vaccine. The cell formulations can contain buffers to maintain a preferred pH range, salts or other components that present an antigen to an individual in a composition that stimulates an immune response to the antigen. The physiologically acceptable carrier also can contain one or more adjuvants that enhance the immune response to an antigen. Pharmaceutically acceptable earners include, for example, pharmaceutically acceptable solvents, suspending agents, or any other pharmacologically inert vehicles for delivering compounds to a subject. Pharmaceutically acceptable carriers can be liquid or solid, and can be selected with the planned manner of administration in mind so as to provide for the desired bulk, consistency, and other pertinent transport and chemical properties, when combined with more or more therapeutic compounds and any other components of a given pharmaceutical composition. Typical pharmaceutically acceptable carriers include, without limitation: water, saline solution, binding agents (e.g., polyvinylpyrrolidone or hydroxypropyl methylcellulose); fillers (e.g., lactose or dextrose and other sugars, gelatin, or calcium sulfate), lubricants (e.g., starch, polyethylene glycol, or sodium acetate), disintegrates (e.g., starch or sodium starch glycolate), and wetting agents (e.g., sodium lauryl sulfate). Compositions can be formulated for subcutaneous, intramuscular, or intradermal administration, or in any manner acceptable for immunization.

An adjuvant refers to a substance which, when added to an immunogenic agent such as a tumor cell expressing secreted vaccine protein (e.g., gp96-Ig) and, optionally, T cell costimulatory fusion polypeptides, nonspecifically enhances or potentiates an immune response to the agent in the recipient host upon exposure to the mixture. Adjuvants can include, for example, oil-in-water emulsions, water-in oil emulsions, alum (aluminum salts), liposomes and microparticles, such as, polysytrene, starch, polyphosphazene and polylactide/polyglycosides.

Adjuvants can also include, for example, squalene mixtures (SAF-I), muramyl peptide, saponin derivatives, mycobacterium cell wall preparations, monophosphoryl lipid A, mycolic acid derivatives, nonionic block copolymer surfactants, Quil A, cholera toxin B subunit, polyphosphazene and derivatives, and immunostimulating complexes (ISCOMs) such as those described by Takahashi et al., *Nature* 1990, 344:873-875. For veterinary use and for production of antibodes in animals, mitogenic components of Freund's adjuvant (both complete and incomplete) can be used. In humans, Incomplete Freund's Adjuvant (IFA) is a useful adjuvant. Various appropriate adjuvants are well known in the art (see, for example, Warren and Chedid, *CRC Critical Reviews in Immunology* 1988, 8:83; and Allison and Byars, in Vaccines: New Approaches to Immunological Problems, 1992, Ellis, ed., Butterworth-Heinemann, Boston). Additional adjuvants include, for example, bacille Calmett-Guerin (BCG), DETOX (containing cell wall skeleton of *Mycobacterium phlei* (CWS) end monophosphoryl lipid A from *Salmonella minnesota* (MPL)), and the like (see, for example, Hoover et al., *J Clin Oncol* 1993, 11:390; and Woodlock et al., *J Immunother* 1999, 22:251-259).

In some embodiments, a vector can be administered to a subject, directly or indirectly (e.g., within a biological cell), one or more times (e.g., once, twice, two to four times, three to five times, five to eight times, six to ten times, eight to 12 times, or more than 12 times). A vector or biological cell as provided herein can be administered one or more times per day, one or more times per week, every other week, one or more times per month, once every two to three months, once every three to six months, or once every six to 12 months. A vector can be administered over any suitable period of time, such as a period from about 1 day to about 12 months. In some embodiments, for example, the period of administration can be from about 1 day to 90 days; from about 1 day to 60 days; from about 1 day to 30 days; from about 1 day to 20 days; from about 1 day to 10 days; from about 1 day to 7 days. In some embodiments, the period of administration can be from about 1 week to 50 weeks; from about 1 week to 50 weeks; from about 1 week to 40 weeks; from about 1 week to 30 weeks; from about 1 week to 24 weeks; from about 1 week to 20 weeks; from about 1 week to 16 weeks; from about 1 week to 12 weeks; from about 1 week to 8 weeks; from about 1 week to 4 weeks; from about 1 week to 3 weeks; from about 1 week to 2 weeks; from about 2 weeks to 3 weeks; from about 2 weeks to 4 weeks; from about 2 weeks to 6 weeks; from about 2 weeks to 8 weeks; from about 3 weeks to 8 weeks; from about 3 weeks to 12 weeks; or from about 4 weeks to 20 weeks.

In some embodiments, after an initial dose (sometimes referred to as a "priming" dose) of a vector has been administered and a maxima) antigen-specific immune response has been achieved, one or more boosting doses of a vector as provided herein can be administered. For example, a boosting dose can be administered about 10 to 30 days, about 15 to 35 days, about 20 to 40 days, about 25 to 45 days, or about 30 to 50 days after a priming dose.

In some embodiments, the methods provided herein can be used for controlling solid tumor growth (e.g., breast, prostate, melanoma, renal, colon, or cervical tumor growth) and/or metastasis. The methods can include administering an effective amount of an expression vector as described herein to a subject in need thereof. In some embodiments, the subject is a mammal (e.g., a human).

The vectors and methods provided herein can be useful for stimulating an immune response against a tumor. Such immune response is useful in treating or alleviating a sign or symptom associated with the tumor. As used herein, by "treating" is meant reducing, preventing, and/or reversing the symptoms in the individual to which a vector as described herein has been administered, as compared to the symptoms of an individual not being treated. A practitioner will appreciate that the methods described herein are to be used in concomitance with continuous clinical evaluations by a skilled practitioner (physician or veterinarian) to determine subsequent therapy. Such evaluations will aid and inform in evaluating whether to increase, reduce, or continue a particular treatment dose, mode of administration, etc.

The methods provided herein can thus be used to treat a tumor, including, for example, a cancer. The methods can be used, for example, to inhibit the growth of a tumor by preventing further tumor growth, by slowing tumor growth, or by causing tumor regression. Thus, the methods can be used, for example, to treat a cancer such as a lung cancer. It will be understood that the subject to which a compound is administered need not suffer from a specific traumatic slate. Indeed, the vectors described herein may be administered prophylactically, prior to development of symptoms (e.g., a patient in remission from cancer). The terms "therapeutic" and "therapeutically," and permutations of these terms, are used to encompass therapeutic, palliative, and prophylactic uses. Thus, as used herein, by "treating or alleviating the symptoms" is meant reducing, preventing, and/or reversing the symptoms of the individual to which a therapeutically effective amount of a composition has been administered, as compared to the symptoms of an individual receiving no such administration.

As used herein, the terms "effective amount" and "therapeutically effective amount" refer to an amount sufficient to provide the desired therapeutic (e.g., anti-cancer, anti-tumor, or anti-infection) effect in a subject (e.g., a human diagnosed as having cancer or an infection). Anti-tumor and anti-cancer effects include, without limitation, modulation of tumor growth (e.g., tumor growth delay), tumor size, or metastasis, the reduction of toxicity and side effects associated with a particular anti-cancer agent the amelioration or minimization of the clinical impairment or symptoms of cancer, extending the survival of the subject beyond that which would otherwise be expected in the absence of such treatment, and the prevention of tumor growth in an animal lacking tumor formation prior to administration, i.e., prophylactic administration. In some embodiments, administration of an effective amount of a vector or a composition, cell, or virus particle containing the vector can increase the activation or proliferation of tumor antigen specific T cells in a subject. For example, the activation or proliferation of tumor antigen specific T cells in the subject can be is increased by at least 10 percent (e.g., at least 25 percent, at least 50 percent, or at least 75 percent) as compared to the level of activation or proliferation of tumor antigen specific T cells in the subject prior to the administration.

One of skill will appreciate that an effective amount of a vector may be lowered or increased by fine tuning and/or by administering more than one dose (e.g., by concomitant administration of two different genetically modified tumor cells containing the vector), or by administering a vector with another agent (e.g., an antagonist of PD-1) to enhance the therapeutic effect (e.g., synergistically). This document therefore provides a method for tailoring the administration/treatment to the particular exigencies specific to a given mammal. Therapeutically effective amounts can be determined by, for example, starting at relatively low amounts and using step-wise increments with concurrent evaluation of beneficial effects. The methods provided herein thus can be used alone or in combination with other well-known tumor therapies, to treat a patient having a tumor. One skilled in the art will readily understand advantageous uses of the vectors and methods provided herein, for example, in prolonging the life expectancy of a cancer patient and/or improving the quality of life of a cancer patient (e.g., a lung cancer patient).

Combination Therapies and Conjugation

In some embodiments, the invention provides for methods that further comprise administering an additional agent to a subject. In some embodiments, the invention pertains to co-administration and/or co-formulation. In some embodiments, administration of vaccine protein (e.g., gp96-Ig) acts synergistically when co-administered with another agent and is administered at doses that are lower than the doses commonly employed when such agents are used as monotherapy.

In some embodiments, administration of vaccine protein (e.g., gp96-Ig) and one or more costimulatory molecules act synergistically when co-administered with another agent and is administered at doses that are lower than the doses commonly employed when such agents are used as monotherapy.

In some embodiments, inclusive of, without limitation, cancer applications, the present invention pertains to chemotherapeutic agents as additional agents. Examples of chemotherapeutic agents include, but are not limited to, alkylating agents such as thiotepa and CYTOXAN cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; cally statin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as minoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL paclitaxel (Bristol-Myers Squibb Oncology, Princeton, N.J.), ABRAXANE Cremophor-free, albumin-engineered nanoparticle formulation of paclitaxel (American Pharmaceutical Partners, Schaumberg, 111.), and TAXOTERE doxetaxel (Rhone-Poulenc Rorer, Antony, France); chlorambucil; GEMZAR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE, vinorelbine; novantrone; teniposide; edatrexate; daunomycin; aminopterin; xeloda; ibandronate; irinotecan (Camptosar, CPT-11) (including the treatment regimen of irinotecan with 5-FU end leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (TYKERB); inhibitors of PKC-α, Raf, H-Ras, EGFR (e.g., erlotinib (Tarceva)) and VEGF-A that reduce cell proliferation and pharmaceutically acceptable salts, adds or derivatives of any of the above. In addition, the methods of treatment can further include the use of radiation. In addition, the methods of treatment can further include the use of photodynamic therapy.

Other additional agents are described elsewhere herein, inducing the blocking antibodies targeted to an immune "checkpoint" molecules.

Subjects and/or Animals

The methods described herein are intended for use with any subject that may experience the benefits of these methods. Thus, "subjects," "patients," and "individuals" (used interchangeably) include humans as well as non-human subjects, particularly domesticated animals.

In some embodiments, the subject and/or animal is a mammal, e.g., a human, mouse, rat, guinea pig, dog, cat, horse, cow, pig, rabbit, sheep, or non-human primate, such as a monkey, chimpanzee, or baboon. In other embodiments, the subject and/or animal is a non-mammal, such, for example, a zebrafish. In some embodiments, the subject and/or animal may comprise fluorescently-tagged cells (with e.g., GFP). In some embodiments, the subject and/or animal is a transgenic animal comprising a fluorescent cell.

In some embodiments, the subject and/or animal is a human. In some embodiments, the human is a pediatric human. In other embodiments, the human is an adult human. In other embodiments, the human is a geriatric human. In other embodiments, the human may be referred to as a patient.

In certain embodiments, the human has an age in a range of from about 0 months to about 6 months old, from about 6 to about 12 months old, from about 6 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

In other embodiments, the subject is a non-human animal, and therefore the invention pertains to veterinary use. In a specific embodiment, the non-human animal is a household pet. In another specific embodiment, the non-human animal is a livestock animal. In certain embodiments, the subject is a human cancer patient that cannot receive chemotherapy, e.g., the patient is unresponsive to chemotherapy or too ill to have a suitable therapeutic window for chemotherapy (e.g., experiencing too many dose- or regimen-limiting side effects). In certain embodiments, the subject is a human cancer patient having advanced and/or metastatic disease.

As used herein, an "allogeneic cell" refers to a cell that is not derived from the individual to which the cell is to be administered, that is, has a different genetic constitution than the individual. An allogeneic cell is generally obtained from the same species as the individual to which the cell is to be administered. For example, the allogeneic cell can be a human cell, as disclosed herein, for administering to a human patient such as a cancer patient. As used herein, an "allogeneic tumor cell" refers to a tumor cell that is not derived from the individual to which the allogeneic cell is to be administered. Generally, the allogeneic tumor cell expresses one or more tumor antigens that can stimulate an immune response against a tumor in an individual to which the cell is to be administered. As used herein, an "allogeneic cancer cell," for example, a lung cancer cell, refers to a cancer cell that is not derived from the individual to which the allogeneic cell is to be administered.

As used herein, a "genetically modified cell" refers to a cell that has been genetically modified to express an exogenous nucleic acid, for example, by transfection or transduction.

Technical and scientific terms used herein have the meaning commonly understood by one of skill in the art to which the present invention pertains, unless otherwise defined.

As used herein, the singular forms "a," "an" and "the" specifically also encompass the plural forms of the terms to which they refer, unless the content clearly dictates otherwise. As used herein, unless specifically indicated otherwise, the word "or" is used in the "inclusive" sense of "and/or"

and not the "exclusive" sense of either/or." In the specification and the appended claims, the singular forms include plural referents unless the context clearly dictates otherwise.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%. As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

The invention will be further described in the following examples, which do not limit the scope of the invention described in the claims.

EXAMPLES

Example 1: Combined Intratumoral Electroporation and Allogeneic Vaccination of Gp96-Ig/Fc-OX40L Stimulates CD8+ T Cell Cross Priming to Tumor-Specific Neoantigens and Enhances Anti-Tumor Response FIG. 1 shows the experimental design of the present Example.

Figure 2C:
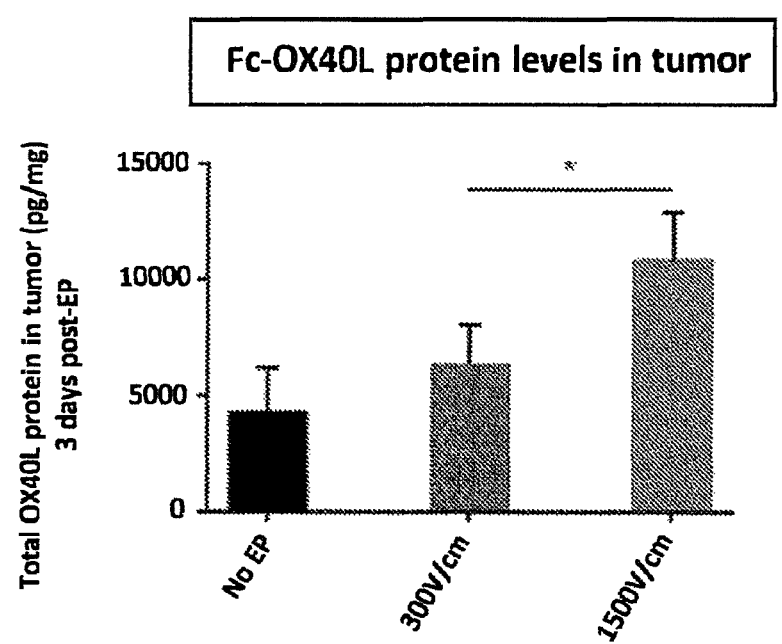

FIG. 2A shows 50 µg of a bovine papilloma virus plasmid vector co-expressing Gp96.Ig and Fc-OX40L (~12 kb) was injected into subcutaneous B16.F10 tumors (n=6 per group) and electroporated under two separate parameters. Three days following electroporation the level of FIG. 2B; tumor cell associated Gp96.Ig mRNA and FIG. 2C: tumor lysate associated OX40L protein was quantified by qPCR and ELISA, respectively.

Figure 3A:
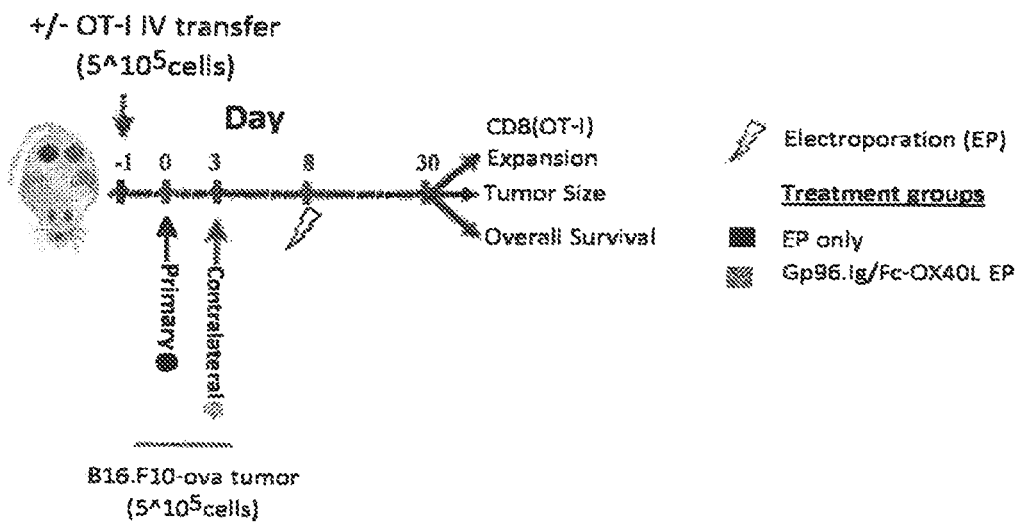
FIG. 3A-F shows intratumoral EP of Gp96-Ig/Fc-OX40L DNA alone leads to CD8 T cell cross priming and delayed tumor growth.
Figure 3B:
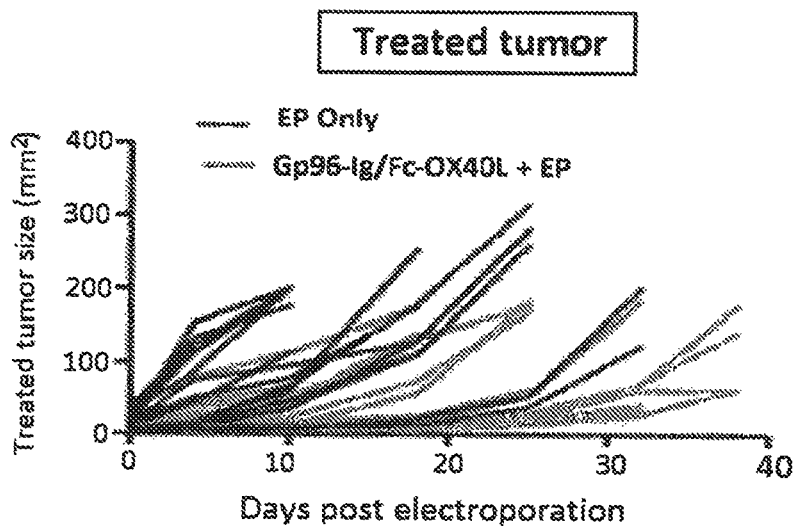
Figure 3C:
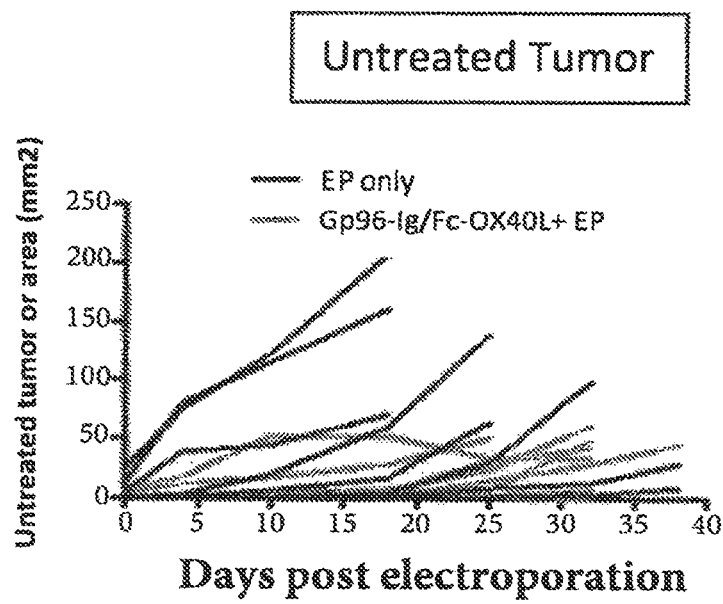
Figure 3D:
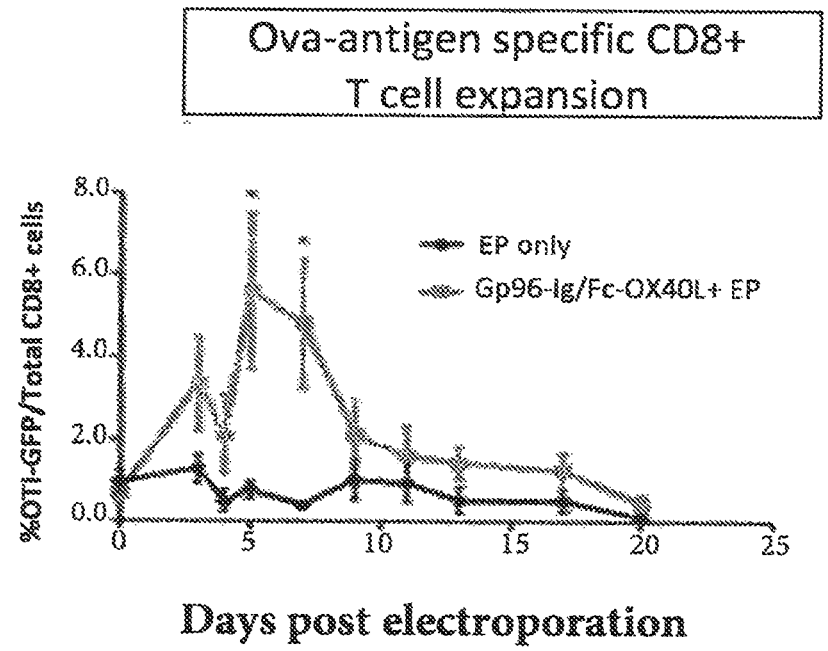
Figure 3E:
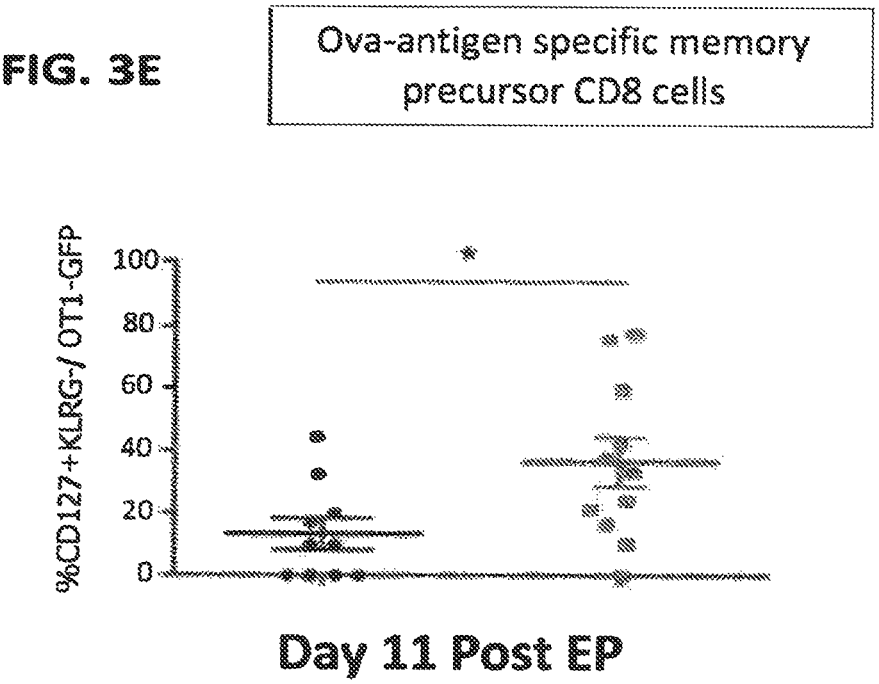
Figure 3F:
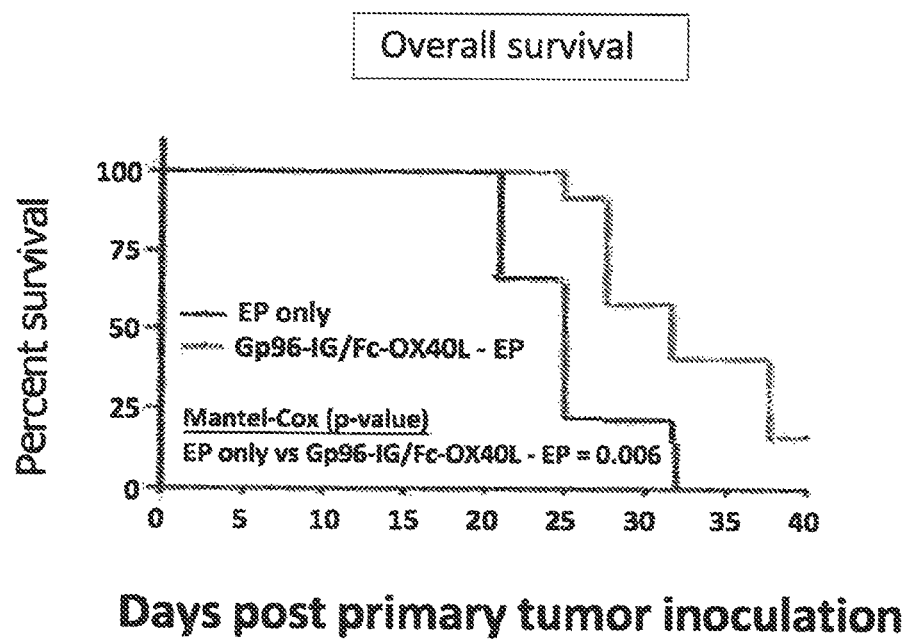

FIG. 3A: C57BL/6 albino mice were adoptively transferred with OT1-GFP cells and inoculated with two B16.F10-ova tumors on opposing rear flanks. Only the primary tumor was electroporated with either saline (EP only) or Gp96.Ig/Fc-OX40L DNA. (FIG. 3B and FIG. 3C) Growth of the primary/treated and contralateral/untreated tumor was monitored over 40 days. FIG. 3D: The percentage of CD8+ OT1-GFP cells in peripheral blood was monitored over time by flow cytometry. FIG. 3E: Phenotypic analysis of ova-antigen specific CD8+ T cells on day 11 following EP by flow cytometry reveals increased numbers of CD127+/KLRG-memory precursor cells in mice EP'd with Gp96.Ig/Fc-OX40L. FIG. 3F: Overall survival of B16.F10 melanoma bearing mice EP'd with saline or Gp96.Ig/Fc-OX40L. * indicates p<0.05. Statistical significance was determined by student t-test and Mantel-Cox test.

Figure 4A:
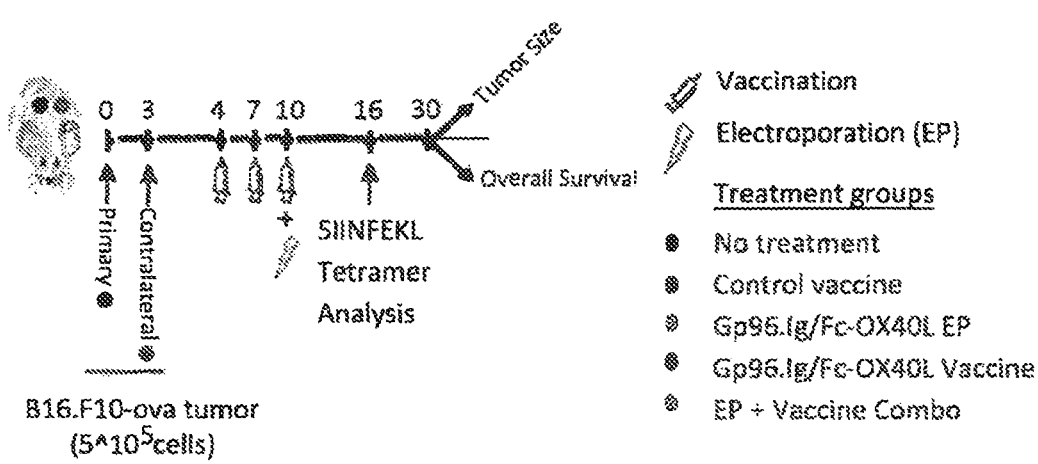
FIG. 4A-F shows combination of intratumoral EP and allogeneic vaccination of Gp96-Ig/Fc-OX40L leads to increased expansion of CD8 T cell cross priming and improved anti-tumor response.
Figure 4B:
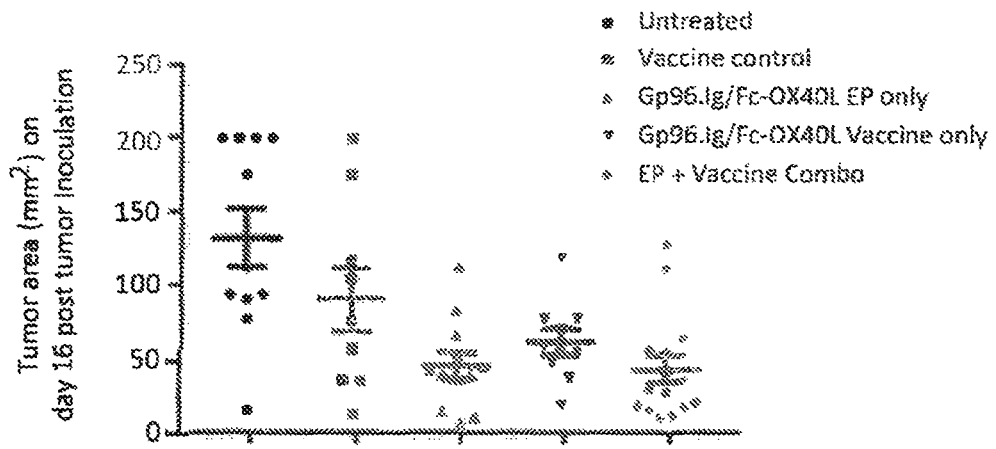
Figure 4C:
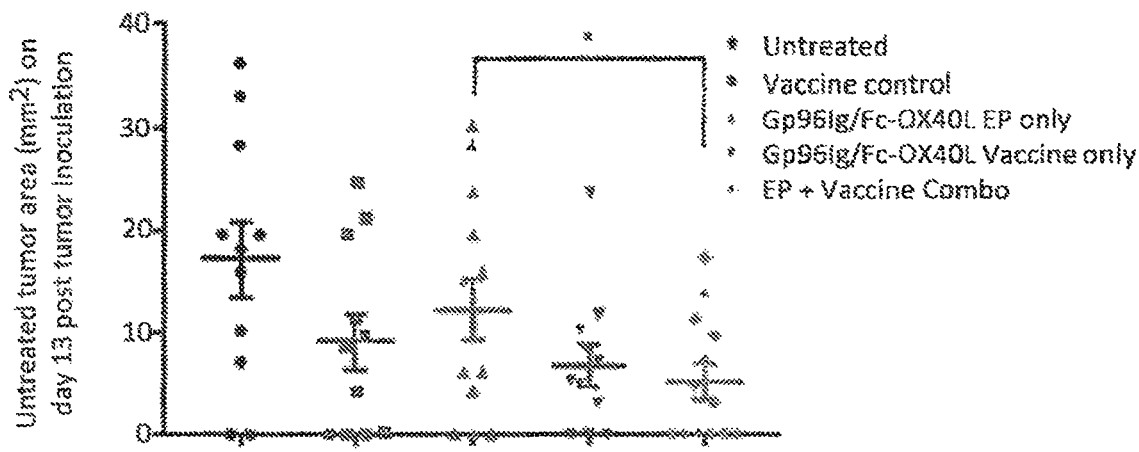
Figure 4D:
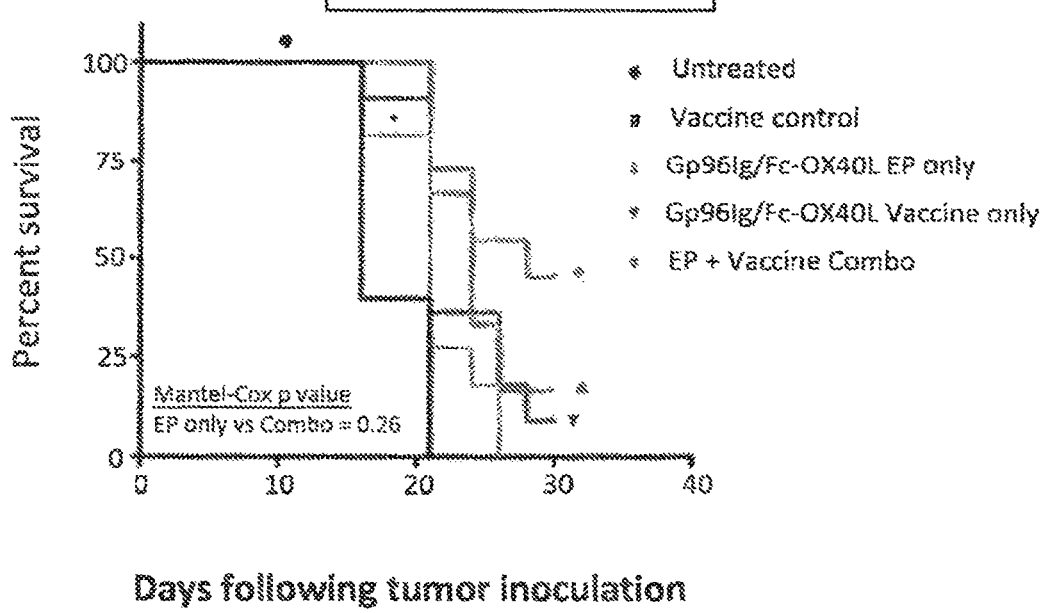
Figure 4E:
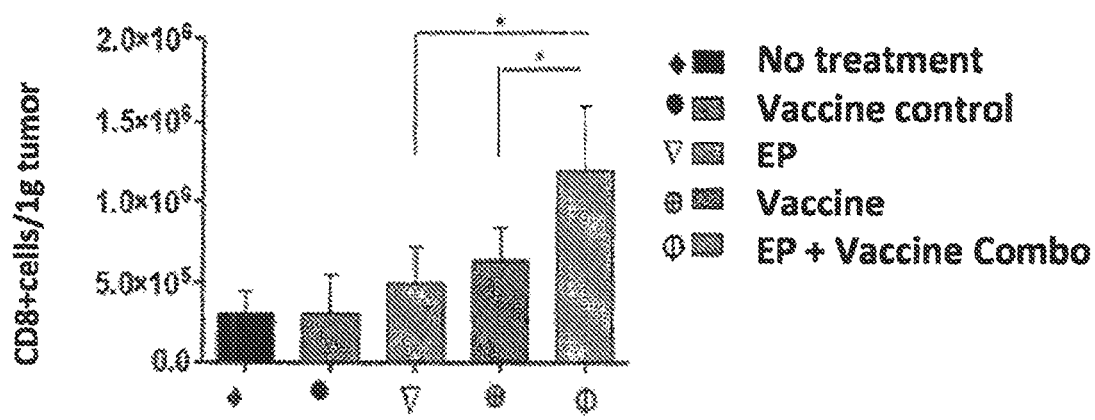
Figure 4F:
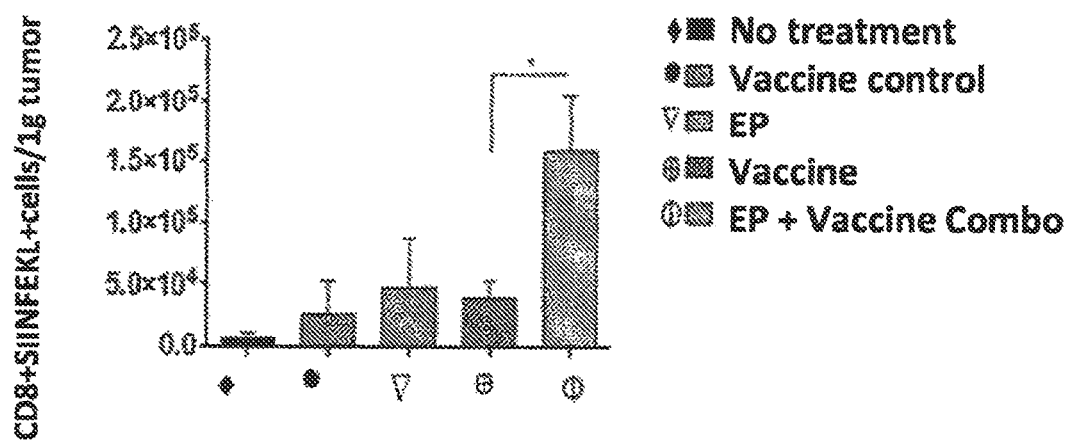

FIG. 4A: C57BL/6 mice bearing primary and contralateral B16.F10-ova tumors on opposing rear flanks were EP'd only in their primary tumor once with Gp96.Ig/Fc-OX40L DNA alone or in combination with IP administration of a triple dose of mitomycin-treated B16.F10-ova allogeneic vaccine cells secreting Gp96.Ig and Fc-OX40L. (FIG. 4B, FIG. 4C and FIG. 4D) Growth of the primary/treated and contralateral/untreated tumors and survival was monitored over 30 days. (FIG. 4E and FIG. 4F) A subgroup of mice from each group (n=6) was sacrificed on day 6 following EP, tumors were excised, weighed and enzymatically dissociated to isolate tumor cells and tumor infiltrating lymphocytes (TIL). Isolated cells were stained for SIINFEKL tetramer+ CD8+ T cells (representing Ova antigen-specific CD8+ T cells) and quantified by flow cytometry. Cells were negatively gated to exclude cells positive for Nk1.1, Gr-1, CD11b and CD11c and subsequently pre-gated on CD3+. * indicates p<0.05. Statistical significance was determined by either student t-test, ANOVA or Mantel-Cox test where appropriate.

This combination approach led to an increased expansion of antigen-specific CD8 T cells in tumors and in the peripheral blood compared to the individual monotherapies, which increased anti-tumor response rates. These findings suggest that a combination approach of allogeneic vaccination and in situ tumor EP of Gp96-Ig/Fc-OX40L may have significant benefit in eliciting a potent immune response in less-immunogenic tumors.

In vivo EP of DNA-based gp96.Ig/Fc-OX40L into B16 melanoma tumors resulted in CD8 T cell cross priming, increased antigen-specific precursor memory T cells and delayed tumor progression of treated and distal, untreated tumors.

Combining in vivo electroporation of gp96.Ig/Fc-OX40L DNA with an allogeneic vaccine secreting the same therapeutic agents enhanced the efficacy of treating B16 melanoma tumors due to improved CD8 T cell cross priming This study provided, inter alia, proof-of-concept for pairing gp96.Ig-based vaccines with intratumoral gp96 therapies Other Embodiments It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The content of any individual section may be equally applicable to all sections.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any way.

What is claimed is:

1. A method for treating a tumor in a subject in need thereof, comprising intratumorally delivering an effective amount of a composition comprising an expression vector that comprises a first nucleotide sequence encoding a secretable gp96-Immunoglobulin fusion protein which lacks the gp96 KDEL (SEQ ID NO:3) sequence, and a second nucleotide sequence encoding a T cell costimulatory fusion protein, by electroporation wherein the T cell costimulatory fusion protein is OX40L-Ig, or a portion thereof that binds to OX40, wherein the intratumoral delivery is in vivo by injection, and further administering to the subject an effective amount of a biological cell comprising an expression vector that comprises a first nucleotide sequence encoding a secretable gp96-Ig fusion protein which lacks the gp96 KDEL (SEQ ID NO:3) sequence, and a second nucleotide sequence encoding a T cell costimulatory fusion protein, wherein the T cell costimulatory fusion protein is OX40L-Ig, or a portion thereof that binds to OX40, and the T cell costimulatory fusion protein enhances activation of antigen-specific T cells when administered to the subject.

2. The method of claim 1, wherein the method elicits a potent immune response in a less-immunogenic tumor characterized by reduced inflammation.

3. The method of claim 1, wherein the method enhances CD4+/CD8+ T cell cross-priming to tumor neo-antigens.

4. The method of claim 1, wherein the vector is a mammalian expression vector.

5. The method of claim 1, wherein the gp96-Ig fusion protein comprises an Ig tag comprising the Fc region of human IgG1, IgG2, IgG3, IgG4, IgM, IgA, or IgE.

6. The method of claim 1, wherein the T cell costimulatory fusion protein comprises an Ig tag comprising the Fc region of human IgG1, IgG2, IgG3, IgG4, IgM, IgA, or IgE.

7. The method of claim 1, wherein the expression vector comprises DNA or RNA.

8. The method of claim 1, wherein the expression vector is incorporated into a virus or virus-like particle.

9. The method of claim 1, wherein delivery increases the activation or proliferation of tumor antigen specific T cells in the patient.

10. The method of claim 9, wherein the activation or proliferation of tumor antigen specific T cells in the patient is increased by at least 25 percent as compared to the level of activation or proliferation of tumor antigen specific T cells in the patient prior to the administration.

11. The method of claim 1, comprising administering in combination with an agent that inhibits immunosuppressive molecules produced by tumor cells.

12. The method of claim 11, wherein the agent that inhibits immunosuppressive molecules is an antibody against PD-1.

* * * * *

SEQUENCE LISTING

<160> NUMBER OF SEQ ID NOS: 49

<210> SEQ ID NO 1
<211> LENGTH: 2412
<212> TYPE: DNA
<213> ORGANISM: Homo sapiens

<400> SEQUENCE: 1

| | | | | | | |
|---|---|---|---|---|---|---|
| atgagggccc | tgtgggtgct | gggcctctgc | tgcgtcctgc | tgaccttcgg | gtcggtcaga | 60 |
| gctgacgatg | aagttgatgt | ggatggtaca | gtagaagagg | atctgggtaa | aagtagagaa | 120 |
| ggatcaagga | cggatgatga | agtagtacag | agagaggaag | aagctattca | gttggatgga | 180 |
| ttaaatgcat | cacaaataag | agaacttaga | gagaagtcgg | aaaagtttgc | cttccaagcc | 240 |
| gaagttaaca | gaatgatgaa | acttatcatc | aattcattgt | ataaaaataa | agagattttc | 300 |
| ctgagagaac | tgatttcaaa | tgcttctgat | gctttagata | agataaggct | aatatcactg | 360 |
| actgatgaaa | atgctctttc | tggaaatgag | gaactaacag | tcaaaattaa | gtgtgataag | 420 |
| gagaagaacc | tgctgcatgt | cacagacacc | ggtgtaggaa | tgaccagaga | agagttggtt | 480 |
| aaaaaccttg | gtaccatagc | caaatctggg | acaagcgagt | ttttaaacaa | aatgactgaa | 540 |
| gcacaggaag | atggccagtc | aacttctgaa | ttgattggcc | agtttggtgt | cggtttctat | 600 |
| tccgccttcc | ttgtagcaga | taaggttatt | gtcacttcaa | acacaacaa | cgatacccag | 660 |
| cacatctggg | agtctgactc | caatgaattt | tctgtaattg | ctgacccaag | aggaaacact | 720 |
| ctaggacggg | gaacgacaat | tacccttgtc | ttaaaagaag | aagcatctga | ttaccttgaa | 780 |
| ttggatacaa | ttaaaaatct | cgtcaaaaaa | tattcacagt | tcataaactt | tcctatttat | 840 |
| gtatggagca | gcaagactga | aactgttgag | gagcccatgg | aggaagaaga | agcagccaaa | 900 |
| gaagagaaag | aagaatctga | tgatgaagct | gcagtagagg | aagaagaaga | agaaaagaaa | 960 |
| ccaaagacta | aaaagttga | aaaaactgtc | tgggactggg | aacttatgaa | tgatatcaaa | 1020 |
| ccaatatggc | agagaccatc | aaaagaagta | gaagaagatg | aatacaaagc | tttctacaaa | 1080 |
| tcattttcaa | aggaaagtga | tgaccccatg | gcttatattc | actttactgc | tgaaggggaa | 1140 |
| gttaccttca | atcaattttt | atttgtaccc | acatctgctc | cacgtggtct | gtttgacgaa | 1200 |
| tatggatcta | aaaagagcga | ttacattaag | ctctatgtgc | gccgtgtatt | catcacagac | 1260 |
| gacttccatg | atatgatgcc | taaataccctc | aattttgtca | agggtgtggt | ggactcagat | 1320 |
| gatctcccct | tgaatgtttc | ccgcgagact | cttcagcaac | ataaactgct | taaggtgatt | 1380 |
| aggaagaagc | ttgttcgtaa | aacgctggac | atgatcaaga | agattgctga | tgataaatac | 1440 |
| aatgatactt | tttggaaaga | atttggtacc | aacatcaagc | ttggtgtgat | tgaagaccac | 1500 |
| tcgaatcgaa | cacgtcttgc | taaacttctt | aggttccagt | cttctcatca | tccaactgac | 1560 |
| attactagcc | tagaccagta | tgtggaaaga | atgaaggaaa | aacaagacaa | aatctacttc | 1620 |
| atggctgggt | ccagcagaaa | agaggctgaa | tcttctccat | tgttgagcg | acttctgaaa | 1680 |
| aagggctatg | aagttattta | cctcacagaa | cctgtggatg | aatactgtat | tcaggccctt | 1740 |
| cccgaatttg | atgggaagag | gttccagaat | gttgccaagg | aaggagtgaa | gttcgatgaa | 1800 |
| agtgagaaaa | ctaaggagag | tcgtgaagca | gttgagaaag | aatttgagcc | tctgctgaat | 1860 |
| tggatgaaag | ataaagccct | taaggacaag | attgaaaagg | ctgtggtgtc | tcagcgcctg | 1920 |
| acagaatctc | cgtgtgcttt | ggtggccagc | cagtacggat | ggtctggcaa | catggagaga | 1980 |
| atcatgaaag | cacaagcgta | ccaaacgggc | aaggacatct | ctacaaatta | ctatgcgagt | 2040 |
| cagaagaaaa | catttgaaat | taatccaga | cacccgctga | tcagagacat | gcttcgacga | 2100 |

```
attaaggaag atgaagatga taaaacagtt ttggatcttg ctgtggtttt gtttgaaaca   2160
gcaacgcttc ggtcagggta tcttttacca gacactaaag catatggaga tagaatagaa   2220
agaatgcttc gcctcagttt gaacattgac cctgatgcaa aggtggaaga gagcccgaa    2280 gaagaacctg aagagacagc agaagacaca acagaagaca cagagcaaga cgaagatgaa   2340
gaaatggatg tgggaacaga tgaagaagaa gaaacagcaa aggaatctac agctgaaaaa   2400
gatgaattgt aa                                                       2412
```

<210> SEQ ID NO 2
<211> LENGTH: 803
<212> TYPE: PRT
<213> ORGANISM: Homo sapiens

<400> SEQUENCE: 2

```
Met Arg Ala Leu Trp Val Leu Gly Leu Cys Cys Val Leu Leu Thr Phe
 1               5                  10                  15

Gly Ser Val Arg Ala Asp Asp Glu Val Asp Val Asp Gly Thr Val Glu
            20                  25                  30

Glu Asp Leu Gly Lys Ser Arg Glu Gly Ser Arg Thr Asp Asp Glu Val
        35                  40                  45

Val Gln Arg Glu Glu Glu Ala Ile Gln Leu Asp Gly Leu Asn Ala Ser
    50                  55                  60

Gln Ile Arg Glu Leu Arg Glu Lys Ser Glu Lys Phe Ala Phe Gln Ala
65                  70                  75                  80

Glu Val Asn Arg Met Met Lys Leu Ile Ile Asn Ser Leu Tyr Lys Asn
                85                  90                  95

Lys Glu Ile Phe Leu Arg Glu Leu Ile Ser Asn Ala Ser Asp Ala Leu
            100                 105                 110

Asp Lys Ile Arg Leu Ile Ser Leu Thr Asp Glu Asn Ala Leu Ser Gly
        115                 120                 125

Asn Glu Glu Leu Thr Val Lys Ile Lys Cys Asp Lys Glu Lys Asn Leu
    130                 135                 140

Leu His Val Thr Asp Thr Gly Val Gly Met Thr Arg Glu Glu Leu Val
145                 150                 155                 160

Lys Asn Leu Gly Thr Ile Ala Lys Ser Gly Thr Ser Glu Phe Leu Asn
                165                 170                 175

Lys Met Thr Glu Ala Gln Glu Asp Gly Gln Ser Thr Ser Glu Leu Ile
            180                 185                 190

Gly Gln Phe Gly Val Gly Phe Tyr Ser Ala Phe Leu Val Ala Asp Lys
        195                 200                 205

Val Ile Val Thr Ser Lys His Asn Asn Asp Thr Gln His Ile Trp Glu
    210                 215                 220

Ser Asp Ser Asn Glu Phe Ser Val Ile Ala Asp Pro Arg Gly Asn Thr
225                 230                 235                 240

Leu Gly Arg Gly Thr Thr Ile Thr Leu Val Leu Lys Glu Glu Ala Ser
                245                 250                 255

Asp Tyr Leu Glu Leu Asp Thr Ile Lys Asn Leu Val Lys Lys Tyr Ser
            260                 265                 270

Gln Phe Ile Asn Phe Pro Ile Tyr Val Trp Ser Ser Lys Thr Glu Thr
        275                 280                 285

Val Glu Glu Pro Met Glu Glu Glu Ala Ala Lys Glu Glu Lys Glu
    290                 295                 300

Glu Ser Asp Asp Glu Ala Ala Val Glu Glu Glu Glu Glu Glu Lys Lys
```

```
305                 310                 315                 320
Pro Lys Thr Lys Lys Val Glu Lys Thr Val Trp Asp Trp Glu Leu Met
                325                 330                 335
Asn Asp Ile Lys Pro Ile Trp Gln Arg Pro Ser Lys Glu Val Glu Glu
            340                 345                 350
Asp Glu Tyr Lys Ala Phe Tyr Lys Ser Phe Ser Lys Glu Ser Asp Asp
        355                 360                 365
Pro Met Ala Tyr Ile His Phe Thr Ala Glu Gly Glu Val Thr Phe Lys
    370                 375                 380
Ser Ile Leu Phe Val Pro Thr Ser Ala Pro Arg Gly Leu Phe Asp Glu
385                 390                 395                 400
Tyr Gly Ser Lys Ser Asp Tyr Ile Lys Leu Tyr Val Arg Arg Val
                405                 410                 415
Phe Ile Thr Asp Asp Phe His Asp Met Met Pro Lys Tyr Leu Asn Phe
            420                 425                 430
Val Lys Gly Val Val Asp Ser Asp Asp Leu Pro Leu Asn Val Ser Arg
        435                 440                 445
Glu Thr Leu Gln Gln His Lys Leu Leu Lys Val Ile Arg Lys Lys Leu
    450                 455                 460
Val Arg Lys Thr Leu Asp Met Ile Lys Lys Ile Ala Asp Asp Lys Tyr
465                 470                 475                 480
Asn Asp Thr Phe Trp Lys Glu Phe Gly Thr Asn Ile Lys Leu Gly Val
                485                 490                 495
Ile Glu Asp His Ser Asn Arg Thr Arg Leu Ala Lys Leu Leu Arg Phe
            500                 505                 510
Gln Ser Ser His His Pro Thr Asp Ile Thr Ser Leu Asp Gln Tyr Val
        515                 520                 525
Glu Arg Met Lys Glu Lys Gln Asp Lys Ile Tyr Phe Met Ala Gly Ser
    530                 535                 540
Ser Arg Lys Glu Ala Glu Ser Ser Pro Phe Val Glu Arg Leu Leu Lys
545                 550                 555                 560
Lys Gly Tyr Glu Val Ile Tyr Leu Thr Glu Pro Val Asp Glu Tyr Cys
                565                 570                 575
Ile Gln Ala Leu Pro Glu Phe Asp Gly Lys Arg Phe Gln Asn Val Ala
            580                 585                 590
Lys Glu Gly Val Lys Phe Asp Glu Ser Glu Lys Thr Lys Glu Ser Arg
        595                 600                 605
Glu Ala Val Glu Lys Glu Phe Glu Pro Leu Leu Asn Trp Met Lys Asp
    610                 615                 620
Lys Ala Leu Lys Asp Lys Ile Glu Lys Ala Val Val Ser Gln Arg Leu
625                 630                 635                 640
Thr Glu Ser Pro Cys Ala Leu Val Ala Ser Gln Tyr Gly Trp Ser Gly
                645                 650                 655
Asn Met Glu Arg Ile Met Lys Ala Gln Ala Tyr Gln Thr Gly Lys Asp
            660                 665                 670
Ile Ser Thr Asn Tyr Tyr Ala Ser Gln Lys Lys Thr Phe Glu Ile Asn
        675                 680                 685
Pro Arg His Pro Leu Ile Arg Asp Met Leu Arg Arg Ile Lys Glu Asp
    690                 695                 700
Glu Asp Asp Lys Thr Val Leu Asp Leu Ala Val Val Leu Phe Glu Thr
705                 710                 715                 720
Ala Thr Leu Arg Ser Gly Tyr Leu Leu Pro Asp Thr Lys Ala Tyr Gly
                725                 730                 735
```

```
Asp Arg Ile Glu Arg Met Leu Arg Leu Ser Leu Asn Ile Asp Pro Asp
                740                 745                 750
Ala Lys Val Glu Glu Pro Glu Glu Pro Glu Glu Thr Ala Glu
        755                 760                 765
Asp Thr Thr Glu Asp Thr Glu Gln Asp Glu Asp Glu Met Asp Val
        770                 775                 780
Gly Thr Asp Glu Glu Glu Thr Ala Lys Glu Ser Thr Ala Glu Lys
785                 790                 795                 800
Asp Glu Leu
```

```
<210> SEQ ID NO 3
<211> LENGTH: 4
<212> TYPE: PRT
<213> ORGANISM: Homo sapiens

<400> SEQUENCE: 3

Lys Asp Glu Leu
1

<210> SEQ ID NO 4
<211> LENGTH: 1455
<212> TYPE: DNA
<213> ORGANISM: Artificial Sequence
<220> FEATURE:
<223> OTHER INFORMATION: Synthetic sequence

<400> SEQUENCE: 4
```

| | | | | | |
|---|---|---|---|---|---|
| atgagactgg | gaagccctgg | cctgctgttt | ctgctgttca | gcagcctgag | agccgacacc | 60 |
| caggaaaaag | aagtgcgggc | catggtggga | agcgacgtgg | aactgagctg | cgcctgtcct | 120 |
| gagggcagca | gattcgacct | gaacgacgtg | tacgtgtact | ggcagaccag | cgagagcaag | 180 |
| accgtcgtga | cctaccacat | cccccagaac | agctccctgg | aaaacgtgga | cagccggtac | 240 |
| agaaaccggg | ccctgatgtc | tcctgccggc | atgctgagag | cgacttcag | cctgcggctg | 300 |
| ttcaacgtga | ccccccagga | cgagcagaaa | ttccactgcc | tggtgctgag | ccagagcctg | 360 |
| ggcttccagg | aagtgctgag | cgtggaagtg | accctgcacg | tggccgccaa | tttcagcgtg | 420 |
| ccagtggtgt | ctgccccca | cagcccttct | caggatgagc | tgaccttcac | ctgtaccagc | 480 |
| atcaacggct | accccagacc | caatgtgtac | tggatcaaca | agaccgacaa | cagcctgctg | 540 |
| gaccaggccc | tgcagaacga | taccgtgttc | ctgaacatgc | ggggcctgta | cgacgtggtg | 600 |
| tccgtgctga | gaatcgccag | aaccccagc | gtgaacatcg | ctgctgcat | cgagaacgtg | 660 |
| ctgctgcagc | agaacctgac | cgtgggcagc | cagaccggca | acgacatcgg | cgagagagac | 720 |
| aagatcaccg | agaaccccgt | gtccaccggc | gagaagaatg | ccgccacctc | taagtacggc | 780 |
| cctccctgcc | cttcttgccc | agcccctgaa | tttctgggcg | accctccgt | gtttctgttc | 840 |
| cccccaaagc | ccaaggacac | cctgatgatc | agccggaccc | ccgaagtgac | ctgcgtggtg | 900 |
| gtggatgtgt | cccaggaaga | tcccgaggtg | cagttcaatt | ggtacgtgga | cggggtggaa | 960 |
| gtgcacaacg | ccaagaccaa | gcccagagag | gaacagttca | acagcaccta | ccgggtggtg | 1020 |
| tctgtgctga | ccgtgctgca | ccaggattgg | ctgagcggca | aagagtacaa | gtgcaaggtg | 1080 |
| tccagcaagg | gcctgcccag | cagcatcgaa | aagaccatca | gcaacgccac | cggccagccc | 1140 |
| agggaacccc | aggtgtacac | actgcccct | agccaggaag | agatgaccaa | gaaccaggtg | 1200 |
| tccctgacct | gtctcgtgaa | gggcttctac | ccctccgata | tcgccgtgga | atgggagagc | 1260 |
| aacggccagc | cagagaacaa | ctacaagacc | accccccag | tgctggacag | cgacggctca | 1320 |

```
ttcttcctgt actcccggct gacagtggac aagagcagct ggcaggaagg caacgtgttc    1380
agctgcagcg tgatgcacga agccctgcac aaccactaca cccagaagtc cctgtctctg    1440
tccctgggca aatga                                                      1455
```

<210> SEQ ID NO 5
<211> LENGTH: 484
<212> TYPE: PRT
<213> ORGANISM: Artificial Sequence
<220> FEATURE:
<223> OTHER INFORMATION: Synthetic sequence

<400> SEQUENCE: 5

```
Met Arg Leu Gly Ser Pro Gly Leu Leu Phe Leu Leu Phe Ser Ser Leu
1               5                   10                  15

Arg Ala Asp Thr Gln Glu Lys Glu Val Arg Ala Met Val Gly Ser Asp
            20                  25                  30

Val Glu Leu Ser Cys Ala Cys Pro Glu Gly Ser Arg Phe Asp Leu Asn
        35                  40                  45

Asp Val Tyr Val Tyr Trp Gln Thr Ser Glu Ser Lys Thr Val Val Thr
    50                  55                  60

Tyr His Ile Pro Gln Asn Ser Ser Leu Glu Asn Val Asp Ser Arg Tyr
65                  70                  75                  80

Arg Asn Arg Ala Leu Met Ser Pro Ala Gly Met Leu Arg Gly Asp Phe
                85                  90                  95

Ser Leu Arg Leu Phe Asn Val Thr Pro Gln Asp Glu Gln Lys Phe His
            100                 105                 110

Cys Leu Val Leu Ser Gln Ser Leu Gly Phe Gln Glu Val Leu Ser Val
        115                 120                 125

Glu Val Thr Leu His Val Ala Ala Asn Phe Ser Val Pro Val Val Ser
    130                 135                 140

Ala Pro His Ser Pro Ser Gln Asp Glu Leu Thr Phe Thr Cys Thr Ser
145                 150                 155                 160

Ile Asn Gly Tyr Pro Arg Pro Asn Val Tyr Trp Ile Asn Lys Thr Asp
                165                 170                 175

Asn Ser Leu Leu Asp Gln Ala Leu Gln Asn Asp Thr Val Phe Leu Asn
            180                 185                 190

Met Arg Gly Leu Tyr Asp Val Val Ser Val Leu Arg Ile Ala Arg Thr
        195                 200                 205

Pro Ser Val Asn Ile Gly Cys Cys Ile Glu Asn Val Leu Leu Gln Gln
    210                 215                 220

Asn Leu Thr Val Gly Ser Gln Thr Gly Asn Asp Ile Gly Glu Arg Asp
225                 230                 235                 240

Lys Ile Thr Glu Asn Pro Val Ser Thr Gly Glu Lys Asn Ala Ala Thr
                245                 250                 255

Ser Lys Tyr Gly Pro Pro Cys Pro Ser Cys Pro Ala Pro Glu Phe Leu
            260                 265                 270

Gly Gly Pro Ser Val Phe Leu Phe Pro Pro Lys Pro Lys Asp Thr Leu
        275                 280                 285

Met Ile Ser Arg Thr Pro Glu Val Thr Cys Val Val Val Asp Val Ser
    290                 295                 300

Gln Glu Asp Pro Glu Val Gln Phe Asn Trp Tyr Val Asp Gly Val Glu
305                 310                 315                 320

Val His Asn Ala Lys Thr Lys Pro Arg Glu Glu Gln Phe Asn Ser Thr
                325                 330                 335
```

```
Tyr Arg Val Val Ser Val Leu Thr Val Leu His Gln Asp Trp Leu Ser
                340                 345                 350

Gly Lys Glu Tyr Lys Cys Lys Val Ser Ser Lys Gly Leu Pro Ser Ser
            355                 360                 365

Ile Glu Lys Thr Ile Ser Asn Ala Thr Gly Gln Pro Arg Glu Pro Gln
        370                 375                 380

Val Tyr Thr Leu Pro Pro Ser Gln Glu Glu Met Thr Lys Asn Gln Val
385                 390                 395                 400

Ser Leu Thr Cys Leu Val Lys Gly Phe Tyr Pro Ser Asp Ile Ala Val
                405                 410                 415

Glu Trp Glu Ser Asn Gly Gln Pro Glu Asn Asn Tyr Lys Thr Thr Pro
            420                 425                 430

Pro Val Leu Asp Ser Asp Gly Ser Phe Phe Leu Tyr Ser Arg Leu Thr
        435                 440                 445

Val Asp Lys Ser Ser Trp Gln Glu Gly Asn Val Phe Ser Cys Ser Val
    450                 455                 460

Met His Glu Ala Leu His Asn His Tyr Thr Gln Lys Ser Leu Ser Leu
465                 470                 475                 480

Ser Leu Gly Lys

<210> SEQ ID NO 6
<211> LENGTH: 1305
<212> TYPE: DNA
<213> ORGANISM: Artificial Sequence
<220> FEATURE:
<223> OTHER INFORMATION: Synthetic sequence

<400> SEQUENCE: 6
atgtctaagt acggccctcc ctgccctagc tgccctgccc tgaatttcct gggcggaccc      60
agcgtgttcc tgttcccccc aaagcccaag acaccctga tgatcagccg gacccccgaa     120
gtgacctgcg tggtggtgga tgtgtcccag gaagatcccg aggtgcagtt caattggtac     180
gtggacggcg tggaagtgca caacgccaag accaagccca gagaggaaca gttcaacagc     240
acctaccggg tggtgtccgt gctgaccgtg ctgcaccagg attggctgag cggcaaagag     300
tacaagtgca aggtgtccag caagggcctg cccagcagca tcgagaaaac catcagcaac     360
gccaccggcc agcccaggga acccagggtg tacacactgc ccctagcca ggaagagatg     420 accaagaacc aggtgtccct gacctgtctc gtgaagggct ctacccctc cgatatcgcc     480 gtggaatggg agagcaacgg ccagcctgag aacaactaca agaccacccc ccagtgctg     540 gacagcgacg gctcattctt cctgtacagc agactgaccg tggacaagag cagctggcag     600
gaaggcaacg tgttcagctg cagcgtgatg cacgaggccc tgcacaacca ctacacccag     660
aagtccctgt ctctgagcct gggcaaggcc tgtccatggg ctgtgtctgg cgctagagcc     720
tctcctggat ctgccgccag ccccagactg agagagggac ctgagctgag ccccgatgat     780
cctgccggac tgctggatct gagacagggc atgttcgccc agctggtggc ccagaacgtg     840
ctgctgatcg atggccccct gagctggtac agcgatcctg actggctgg cgtgtcactg     900 acaggcggcc tgagctacaa agaggacacc aaagaactgg tggtggccaa ggccggcgtg     960
tactacgtgt tctttcagct ggaactgcgg agagtggtgg ccggcgaagg atccggctct    1020
gtgtctctgg ctctgcatct gcagcccctg agatctgctg ctggcgctgc tgctctggcc    1080
ctgacagtgg aacctgcctc ctgcctctagc gaggccagaa acagcgcatt cgggtttcaa    1140
ggcagactgc tgcacctgtc tgccggccag agactgggag tgcatctgca cacagaggcc    1200
```

```
                                    -continued agagccaggc acgcctggca gctgactcag ggcgctacag tgctgggcct gttcagagtg    1260 accccccgaga ttccagccgg cctgcctagc cccagatccg aatga                   1305

<210> SEQ ID NO 7
<211> LENGTH: 434
<212> TYPE: PRT
<213> ORGANISM: Artificial Sequence
<220> FEATURE:
<223> OTHER INFORMATION: Synthetic sequence

<400> SEQUENCE: 7

Met Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Ser Gly Lys Glu Tyr Lys Cys Lys Val Ser Ser Lys Gly Leu Pro Ser
            100                 105                 110

Ser Ile Glu Lys Thr Ile Ser Asn Ala Thr Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Ser Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys Ala Cys Pro Trp Ala Val Ser Gly Ala Arg Ala
225                 230                 235                 240

Ser Pro Gly Ser Ala Ala Ser Pro Arg Leu Arg Glu Gly Pro Glu Leu
                245                 250                 255

Ser Pro Asp Asp Pro Ala Gly Leu Leu Asp Leu Arg Gln Gly Met Phe
            260                 265                 270

Ala Gln Leu Val Ala Gln Asn Val Leu Leu Ile Asp Gly Pro Leu Ser
        275                 280                 285

Trp Tyr Ser Asp Pro Gly Leu Ala Gly Val Ser Leu Thr Gly Gly Leu
    290                 295                 300

Ser Tyr Lys Glu Asp Thr Lys Glu Leu Val Val Ala Lys Ala Gly Val
305                 310                 315                 320

Tyr Tyr Val Phe Phe Gln Leu Glu Leu Arg Arg Val Val Ala Gly Glu
                325                 330                 335

Gly Ser Gly Ser Val Ser Leu Ala Leu His Leu Gln Pro Leu Arg Ser
```

```
            340                 345                 350
Ala Ala Gly Ala Ala Ala Leu Ala Leu Thr Val Asp Leu Pro Pro Ala
            355                 360                 365

Ser Ser Glu Ala Arg Asn Ser Ala Phe Gly Phe Gln Gly Arg Leu Leu
        370                 375                 380

His Leu Ser Ala Gly Gln Arg Leu Gly Val His Leu His Thr Glu Ala
385                 390                 395                 400

Arg Ala Arg His Ala Trp Gln Leu Thr Gln Gly Ala Thr Val Leu Gly
                405                 410                 415

Leu Phe Arg Val Thr Pro Glu Ile Pro Ala Gly Leu Pro Ser Pro Arg
            420                 425                 430

Ser Glu

<210> SEQ ID NO 8
<211> LENGTH: 1284
<212> TYPE: DNA
<213> ORGANISM: Artificial Sequence
<220> FEATURE:
<223> OTHER INFORMATION: Synthetic sequence

<400> SEQUENCE: 8
atgtctaagt acggccctcc ctgccctagc tgccctgccc ctgaatttct gggcggaccc     60
agcgtgttcc tgttcccccc aaagcccaag acacccctga tcagccg gaccccgaa       120 gtgacctgcg tggtggtgga tgtgtcccag gaagatcccg aggtgcagtt caattggtac    180
gtggacggcg tggaagtgca caacgccaag accaagccca gagaggaaca gttcaacagc    240
acctaccggg tggtgtccgt gctgaccgtg ctgcaccagg attggctgag cggcaaagag    300
tacaagtgca aggtgtccag caagggcctg cccagcagca tcgagaaaac catcagcaac    360
gccaccggcc agcccaggga acccaggtg tacacactgc cccctagcca ggaagagatg    420
accaagaacc aggtgtccct gacctgtctc gtgaagggct ctaccccctc cgatatcgcc    480
gtggaatggg agagcaacgg ccagcctgag aacaactaca agaccacccc cccagtgctg    540
gacagcgacg gctcattctt cctgtacagc agactgaccg tggacaagag cagctggcag    600
gaaggcaacg tgttcagctg cagcgtgatg cacgaggccc tgcacaacca ctacacccag    660
aagtccctgt ctctgagcct gggcaagatc gagggccgga tggatagagc ccagggcgaa    720
gcctgcgtgc agttccaggc tctgaagggc aggaattcg ccccagcca ccagcaggtg     780 tacgcccctc tgagagccga cggcgataag cctagagccc acctgacagt cgtgcggcag    840
acccctaccc agcacttcaa gaatcagttc cccgccctgc actgggagca cgaactgggc    900
ctggccttca ccaagaacag aatgaactac accaacaagt ttctgctgat ccccgagagc    960
ggcgactact catctacag ccaagtgacc ttccggggca tgaccagcga gtgcagcgag   1020
atcagacagg ccggcagacc taacaagccc gacagcatca ccgtcgtgat caccaaagtg    1080
accgacagct acccccgagcc cacccagctg ctgatgggca ccaagagcgt gtgcgaagtg    1140
ggcagcaact ggttccagcc catctacctg ggcgccatgt ttagtctgca agagggcgac    1200
aagctgatgg tcaacgtgtc cgacatcagc ctggtggatt acaccaaaga ggacaagacc    1260
ttcttcggcg cctttctgct ctga                                          1284

<210> SEQ ID NO 9
<211> LENGTH: 427
<212> TYPE: PRT
<213> ORGANISM: Artificial Sequence
<220> FEATURE:
```

<223> OTHER INFORMATION: Synthetic sequence

<400> SEQUENCE: 9

Met Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Ser Gly Lys Glu Tyr Lys Cys Lys Val Ser Ser Lys Gly Leu Pro Ser
            100                 105                 110

Ser Ile Glu Lys Thr Ile Ser Asn Ala Thr Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Ser Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Lys Ile Glu Gly Arg Met Asp Arg Ala Gln Gly Glu
225                 230                 235                 240

Ala Cys Val Gln Phe Gln Ala Leu Lys Gly Gln Glu Phe Ala Pro Ser
                245                 250                 255

His Gln Gln Val Tyr Ala Pro Leu Arg Ala Asp Gly Asp Lys Pro Arg
            260                 265                 270

Ala His Leu Thr Val Val Arg Gln Thr Pro Thr Gln His Phe Lys Asn
        275                 280                 285

Gln Phe Pro Ala Leu His Trp Glu His Glu Leu Gly Leu Ala Phe Thr
    290                 295                 300

Lys Asn Arg Met Asn Tyr Thr Asn Lys Phe Leu Leu Ile Pro Glu Ser
305                 310                 315                 320

Gly Asp Tyr Phe Ile Tyr Ser Gln Val Thr Phe Arg Gly Met Thr Ser
                325                 330                 335

Glu Cys Ser Glu Ile Arg Gln Ala Gly Arg Pro Asn Lys Pro Asp Ser
            340                 345                 350

Ile Thr Val Val Ile Thr Lys Val Thr Asp Ser Tyr Pro Glu Pro Thr
        355                 360                 365

Gln Leu Leu Met Gly Thr Lys Ser Val Cys Glu Val Gly Ser Asn Trp
    370                 375                 380

Phe Gln Pro Ile Tyr Leu Gly Ala Met Phe Ser Leu Gln Glu Gly Asp
385                 390                 395                 400

Lys Leu Met Val Asn Val Ser Asp Ile Ser Leu Val Asp Tyr Thr Lys
            405                 410                 415

Glu Asp Lys Thr Phe Phe Gly Ala Phe Leu Leu
            420                 425

<210> SEQ ID NO 10
<211> LENGTH: 1107
<212> TYPE: DNA
<213> ORGANISM: Artificial Sequence
<220> FEATURE:
<223> OTHER INFORMATION: Synthetic sequence

<400> SEQUENCE: 10
atgtctaagt acggccctcc ctgccctagc tgccctgccc ctgaatttct gggcggaccc      60
agcgtgttcc tgttcccccc aaagcccaag acacccctga tcagccg acccccgaa        120 gtgacctgcg tggtggtgga tgtgtcccag gaagatcccg aggtgcagtt caattggtac     180
gtggacggcg tggaagtgca caacgccaag accaagccca gagaggaaca gttcaacagc    240
acctaccggg tggtgtccgt gctgaccgtg ctgcaccagg attggctgag cggcaaagag    300
tacaagtgca aggtgtccag caagggcctg cccagcagca tcgagaaaac catcagcaac    360
gccaccggcc agcccaggga accccaggtg tacacactgc cccctagcca ggaagagatg    420
accaagaacc aggtgtccct gacctgtctc gtgaagggct tctaccccctc cgatatcgcc    480 gtggaatggg agagcaacgg ccagcctgag aacaactaca agaccacccc ccagtgctg    540 gacagcgacg gctcattctt cctgtacagc agactgaccg tggacaagag cagctggcag    600
gaaggcaacg tgttcagctg cagcgtgatg cacgaggccc tgcacaacca ctacacccag    660
aagtccctgt ctctgagcct gggcaagatc gagggccgga tggatcaggt gtcacacaga    720 taccccccgga tccagagcat caaagtgcag tttaccgagt acaagaaaga aagggctttt   780
atcctgacca gccagaaaga ggacgagatc atgaaggtgc agaacaacag cgtgatcatc    840
aactgcgacg ggttctacct gatcagcctg aagggctact tcagtcagga agtgaacatc    900
agcctgcact accagaagga cgaggaaccc ctgttccagc tgaagaaagt gcggagcgtg    960
aacagcctga tggtggcctc tctgacctac aaggacaagg tgtacctgaa cgtgaccacc    1020
gacaacacca gcctggacga cttccacgtg aacggcggcg agctgatcct gattcaccag    1080
aaccccggcg agttctgcgt gctctga                                       1107

<210> SEQ ID NO 11
<211> LENGTH: 368
<212> TYPE: PRT
<213> ORGANISM: Artificial Sequence
<220> FEATURE:
<223> OTHER INFORMATION: Synthetic sequence

<400> SEQUENCE: 11

Met Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

```
            Thr Tyr Arg Val Val Ser Val Leu Thr Val Leu His Gln Asp Trp Leu
                            85                  90                  95

Ser Gly Lys Glu Tyr Lys Cys Lys Val Ser Ser Lys Gly Leu Pro Ser
                        100                 105                 110

Ser Ile Glu Lys Thr Ile Ser Asn Ala Thr Gly Gln Pro Arg Glu Pro
                        115                 120                 125

Gln Val Tyr Thr Leu Pro Pro Ser Gln Glu Glu Met Thr Lys Asn Gln
                        130                 135                 140

Val Ser Leu Thr Cys Leu Val Lys Gly Phe Tyr Pro Ser Asp Ile Ala
            145                 150                 155                 160

Val Glu Trp Glu Ser Asn Gly Gln Pro Glu Asn Asn Tyr Lys Thr Thr
                            165                 170                 175

Pro Pro Val Leu Asp Ser Asp Gly Ser Phe Phe Leu Tyr Ser Arg Leu
                        180                 185                 190

Thr Val Asp Lys Ser Ser Trp Gln Glu Gly Asn Val Phe Ser Cys Ser
                        195                 200                 205

Val Met His Glu Ala Leu His Asn His Tyr Thr Gln Lys Ser Leu Ser
            210                 215                 220

Leu Ser Leu Gly Lys Ile Glu Gly Arg Met Asp Gln Val Ser His Arg
            225                 230                 235                 240

Tyr Pro Arg Ile Gln Ser Ile Lys Val Gln Phe Thr Glu Tyr Lys Lys
                            245                 250                 255

Glu Lys Gly Phe Ile Leu Thr Ser Gln Lys Glu Asp Glu Ile Met Lys
                        260                 265                 270

Val Gln Asn Asn Ser Val Ile Ile Asn Cys Asp Gly Phe Tyr Leu Ile
                        275                 280                 285

Ser Leu Lys Gly Tyr Phe Ser Gln Glu Val Asn Ile Ser Leu His Tyr
                        290                 295                 300

Gln Lys Asp Glu Glu Pro Leu Phe Gln Leu Lys Lys Val Arg Ser Val
            305                 310                 315                 320

Asn Ser Leu Met Val Ala Ser Leu Thr Tyr Lys Asp Lys Val Tyr Leu
                            325                 330                 335

Asn Val Thr Thr Asp Asn Thr Ser Leu Asp Asp Phe His Val Asn Gly
                        340                 345                 350

Gly Glu Leu Ile Leu Ile His Gln Asn Pro Gly Glu Phe Cys Val Leu
                        355                 360                 365

<210> SEQ ID NO 12
<211> LENGTH: 1588
<212> TYPE: DNA
<213> ORGANISM: Homo sapiens

<400> SEQUENCE: 12
tcccaagtag ctgggactac aggagcccac caccaccccc ggctaatttt ttgtattttt      60
agtagagacg gggtttcacc gtgttagcca gatggtcttg atcacctgac ctcgtgatc     120 cacccgcctt ggcctcccaa agtgctggga ttacaggcat gagccaccgc gcccggcctc     180
cattcaagtc tttattgaat atctgctatg ttctacacac tgttctaggt gctggggatg     240
caacagggga caaataggc aaaatccctg tccttttggg gttgacattc tagtgactct      300
tcatgtagtc tagaagaagc tcagtgaata gtgtctgtgg ttgttaccag ggacacaatg     360
acaggaacat tcttgggtag agtgagaggc ctggggaggg aagggtctct aggatggagc     420
agatgctggg cagtcttagg gagccccctcc tggcatgcac ccctcatcc ctcaggccac      480 ccccgtccct tgcaggagca ccctggggag ctgtccagag cgctgtgccg ctgtctgtgg     540
```

```
ctggaggcag agtaggtggt gtgctgggaa tgcgagtggg agaactggga tggaccgagg      600
ggaggcgggt gaggaggggg gcaaccaccc aacacccacc agctgctttc agtgttctgg      660
gtccaggtgc tcctggctgg ccttgtggtc cccctcctgc ttggggccac cctgacctac      720
acataccgcc actgctggcc tcacaagccc ctggttactg cagatgaagc tgggatggag      780
gctctgaccc caccaccggc acccatctg tcacccttgg acagcgccca cccttcta       840 gcacctcctg acagcagtga aagatctgc accgtccagt tggtgggtaa cagctggacc      900
cctggctacc ccgagaccca ggaggcgctc tgcccgcagg tgacatggtc ctgggaccag      960
ttgcccagca gagctcttgg ccccgctgct gcgcccacac tctcgccaga gtccccagcc     1020
ggctcgccag ccatgatgct gcagccgggc ccgcagctct acgacgtgat ggacgcggtc     1080
ccagcgcggc gctggaagga gttcgtgcgc acgctgggc tgcgcgaggc agagatcgaa     1140
gccgtggagg tggagatcgg ccgcttccga gaccagcagt acgagatgct caagcgctgg     1200
cgccagcagc agcccgcggg cctcggagcc gtttacgcgg ccctggagcg catggggctg     1260
gacggctgcg tggaagactt gcgcagccgc ctgcagcgcg gcccgtgaca cggcgcccac     1320
ttgccaccta ggcgctctgg tggcccttgc agaagcccta agtacggtta cttatgcgtg     1380
tagacatttt atgtcactta ttaagccgct ggcacggccc tgcgtagcag caccagccgg     1440
ccccacccct gctcgcccct atcgctccag ccaaggcgaa aagcacgaa cgaatgtcga     1500 gaggggtga agacatttct caacttctcg gccggagttt ggctgagatc gcggtattaa     1560
atctgtgaaa gaaacaaaa caaaacaa                                         1588

<210> SEQ ID NO 13
<211> LENGTH: 426
<212> TYPE: PRT
<213> ORGANISM: Homo sapiens

<400> SEQUENCE: 13

Met Glu Gln Arg Pro Arg Gly Cys Ala Ala Val Ala Ala Ala Leu Leu
1               5                   10                  15

Leu Val Leu Leu Gly Ala Arg Ala Gln Gly Gly Thr Arg Ser Pro Arg
            20                  25                  30

Cys Asp Cys Ala Gly Asp Phe His Lys Lys Ile Gly Leu Phe Cys Cys
        35                  40                  45

Arg Gly Cys Pro Ala Gly His Tyr Leu Lys Ala Pro Cys Thr Glu Pro
    50                  55                  60

Cys Gly Asn Ser Thr Cys Leu Val Cys Pro Gln Asp Thr Phe Leu Ala
65                  70                  75                  80

Trp Glu Asn His His Asn Ser Glu Cys Ala Arg Cys Gln Ala Cys Asp
                85                  90                  95

Glu Gln Ala Ser Gln Val Ala Leu Glu Asn Cys Ser Ala Val Ala Asp
            100                 105                 110

Thr Arg Cys Gly Cys Lys Pro Gly Trp Phe Val Glu Cys Gln Val Ser
        115                 120                 125

Gln Cys Val Ser Ser Pro Phe Tyr Cys Gln Pro Cys Leu Asp Cys
    130                 135                 140

Gly Ala Leu His Arg His Thr Arg Leu Leu Cys Ser Arg Arg Asp Thr
145                 150                 155                 160

Asp Cys Gly Thr Cys Leu Pro Gly Phe Tyr Glu His Gly Asp Gly Cys
                165                 170                 175

Val Ser Cys Pro Thr Pro Pro Pro Ser Leu Ala Gly Ala Pro Trp Gly
```

```
                180               185               190
Ala Val Gln Ser Ala Val Pro Leu Ser Val Ala Gly Gly Arg Val Gly
            195                 200                 205
Val Phe Trp Val Gln Val Leu Leu Ala Gly Leu Val Val Pro Leu Leu
            210                 215                 220
Leu Gly Ala Thr Leu Thr Tyr Thr Tyr Arg His Cys Trp Pro His Lys
225                 230                 235                 240
Pro Leu Val Thr Ala Asp Glu Ala Gly Met Glu Ala Leu Thr Pro Pro
                245                 250                 255
Pro Ala Thr His Leu Ser Pro Leu Asp Ser Ala His Thr Leu Leu Ala
                260                 265                 270
Pro Pro Asp Ser Ser Glu Lys Ile Cys Thr Val Gln Leu Val Gly Asn
            275                 280                 285
Ser Trp Thr Pro Gly Tyr Pro Glu Thr Gln Glu Ala Leu Cys Pro Gln
            290                 295                 300
Val Thr Trp Ser Trp Asp Gln Leu Pro Ser Arg Ala Leu Gly Pro Ala
305                 310                 315                 320
Ala Ala Pro Thr Leu Ser Pro Glu Ser Pro Ala Gly Ser Pro Ala Met
                325                 330                 335
Met Leu Gln Pro Gly Pro Gln Leu Tyr Asp Val Met Asp Ala Val Pro
                340                 345                 350
Ala Arg Arg Trp Lys Glu Phe Val Arg Thr Leu Gly Leu Arg Glu Ala
            355                 360                 365
Glu Ile Glu Ala Val Glu Val Glu Ile Gly Arg Phe Arg Asp Gln Gln
            370                 375                 380
Tyr Glu Met Leu Lys Arg Trp Arg Gln Gln Pro Ala Gly Leu Gly
385                 390                 395                 400
Ala Val Tyr Ala Ala Leu Glu Arg Met Gly Leu Asp Gly Cys Val Glu
                405                 410                 415
Asp Leu Arg Ser Arg Leu Gln Arg Gly Pro
            420                 425

<210> SEQ ID NO 14
<211> LENGTH: 20
<212> TYPE: DNA
<213> ORGANISM: Artificial sequence
<220> FEATURE:
<223> OTHER INFORMATION: Synthetic sequence

<400> SEQUENCE: 14
ctgccacggc acagtcattg                                           20

<210> SEQ ID NO 15
<211> LENGTH: 20
<212> TYPE: DNA
<213> ORGANISM: Artificial sequence
<220> FEATURE:
<223> OTHER INFORMATION: Synthetic sequence

<400> SEQUENCE: 15
gccagttcct ccagatatcc                                           20

<210> SEQ ID NO 16
<211> LENGTH: 20
<212> TYPE: DNA
<213> ORGANISM: Artificial sequence
<220> FEATURE:
<223> OTHER INFORMATION: Synthetic sequence
```

<400> SEQUENCE: 16
ccacgctctt ctgtctactg                                       20

<210> SEQ ID NO 17
<211> LENGTH: 21
<212> TYPE: DNA
<213> ORGANISM: Artificial sequence
<220> FEATURE:
<223> OTHER INFORMATION: Synthetic sequence

<400> SEQUENCE: 17
gccatagaac tgatgagagg g                                     21

<210> SEQ ID NO 18
<211> LENGTH: 21
<212> TYPE: DNA
<213> ORGANISM: Artificial sequence
<220> FEATURE:
<223> OTHER INFORMATION: Synthetic sequence

<400> SEQUENCE: 18
ctactgctga ccttgtctct g                                     21

<210> SEQ ID NO 19
<211> LENGTH: 20
<212> TYPE: DNA
<213> ORGANISM: Artificial sequence
<220> FEATURE:
<223> OTHER INFORMATION: Synthetic sequence

<400> SEQUENCE: 19
agtaaggcca tgtagggtcg                                       20

<210> SEQ ID NO 20
<211> LENGTH: 24
<212> TYPE: DNA
<213> ORGANISM: Artificial sequence
<220> FEATURE:
<223> OTHER INFORMATION: Synthetic sequence

<400> SEQUENCE: 20
ctgcggcatg ttctggattt gact                                  24

<210> SEQ ID NO 21
<211> LENGTH: 24
<212> TYPE: DNA
<213> ORGANISM: Artificial sequence
<220> FEATURE:
<223> OTHER INFORMATION: Synthetic sequence

<400> SEQUENCE: 21
agtccaccac agttgctgac tcat                                  24

<210> SEQ ID NO 22
<211> LENGTH: 21
<212> TYPE: DNA
<213> ORGANISM: Artificial sequence
<220> FEATURE:
<223> OTHER INFORMATION: Synthetic sequence

<400> SEQUENCE: 22
gacacagtag agtgtcgcat g                                     21

<210> SEQ ID NO 23
<211> LENGTH: 20

<212> TYPE: DNA
<213> ORGANISM: Artificial sequence
<220> FEATURE:
<223> OTHER INFORMATION: Synthetic sequence

<400> SEQUENCE: 23
aagcatgctc tgtggagctg                                           20

<210> SEQ ID NO 24
<211> LENGTH: 20
<212> TYPE: DNA
<213> ORGANISM: Artificial sequence
<220> FEATURE:
<223> OTHER INFORMATION: Synthetic sequence

<400> SEQUENCE: 24
aaggccaacc gtgaaaagat                                           20

<210> SEQ ID NO 25
<211> LENGTH: 21
<212> TYPE: DNA
<213> ORGANISM: Artificial sequence
<220> FEATURE:
<223> OTHER INFORMATION: Synthetic sequence

<400> SEQUENCE: 25
gtggtacgac cagaggcata c                                         21

<210> SEQ ID NO 26
<211> LENGTH: 5
<212> TYPE: PRT
<213> ORGANISM: Artificial Sequence
<220> FEATURE:
<223> OTHER INFORMATION: Synthetic sequence

<400> SEQUENCE: 26

Gly Gly Gly Gly Ser
1               5

<210> SEQ ID NO 27
<211> LENGTH: 5
<212> TYPE: PRT
<213> ORGANISM: Artificial sequence
<220> FEATURE:
<223> OTHER INFORMATION: Synthetic sequence

<400> SEQUENCE: 27

Gly Gly Gly Gly Ser
1               5

<210> SEQ ID NO 28
<211> LENGTH: 8
<212> TYPE: PRT
<213> ORGANISM: Artificial sequence
<220> FEATURE:
<223> OTHER INFORMATION: Synthetic sequence

<400> SEQUENCE: 28

Gly Gly Gly Gly Gly Gly Gly Gly
1               5

<210> SEQ ID NO 29
<211> LENGTH: 6
<212> TYPE: PRT
<213> ORGANISM: Artificial sequence
<220> FEATURE:
<223> OTHER INFORMATION: Synthetic sequence

<400> SEQUENCE: 29

Gly Gly Gly Gly Gly Gly
1               5

<210> SEQ ID NO 30
<211> LENGTH: 5
<212> TYPE: PRT
<213> ORGANISM: Artificial sequence
<220> FEATURE:
<223> OTHER INFORMATION: Synthetic sequence

<400> SEQUENCE: 30

Glu Ala Ala Ala Lys
1               5

<210> SEQ ID NO 31
<211> LENGTH: 7
<212> TYPE: PRT
<213> ORGANISM: Artificial sequence
<220> FEATURE:
<223> OTHER INFORMATION: Synthetic sequence

<400> SEQUENCE: 31

Ala Glu Ala Ala Ala Lys Ala
1               5

<210> SEQ ID NO 32
<211> LENGTH: 12
<212> TYPE: PRT
<213> ORGANISM: Artificial sequence
<220> FEATURE:
<223> OTHER INFORMATION: Synthetic sequence

<400> SEQUENCE: 32

Ala Glu Ala Ala Ala Lys Glu Ala Ala Ala Lys Ala
1               5                   10

<210> SEQ ID NO 33
<211> LENGTH: 46
<212> TYPE: PRT
<213> ORGANISM: Artificial sequence
<220> FEATURE:
<223> OTHER INFORMATION: Synthetic sequence

<400> SEQUENCE: 33

Ala Glu Ala Ala Ala Lys Glu Ala Ala Ala Lys Glu Ala Ala Ala Lys
1               5                   10                  15

Glu Ala Ala Ala Lys Ala Leu Glu Ala Glu Ala Ala Ala Lys Glu Ala
            20                  25                  30

Ala Ala Lys Glu Ala Ala Ala Lys Glu Ala Ala Ala Lys Ala
        35                  40                  45

<210> SEQ ID NO 34
<211> LENGTH: 5
<212> TYPE: PRT
<213> ORGANISM: Artificial sequence
<220> FEATURE:
<223> OTHER INFORMATION: Synthetic sequence

<400> SEQUENCE: 34

Pro Ala Pro Ala Pro
1               5

<210> SEQ ID NO 35

```
<211> LENGTH: 18
<212> TYPE: PRT
<213> ORGANISM: Artificial sequence
<220> FEATURE:
<223> OTHER INFORMATION: Synthetic sequence

<400> SEQUENCE: 35

Lys Glu Ser Gly Ser Val Ser Ser Glu Gln Leu Ala Gln Phe Arg Ser
1               5                   10                  15

Leu Asp

<210> SEQ ID NO 36
<211> LENGTH: 14
<212> TYPE: PRT
<213> ORGANISM: Artificial sequence
<220> FEATURE:
<223> OTHER INFORMATION: Synthetic sequence

<400> SEQUENCE: 36

Glu Gly Lys Ser Ser Gly Ser Gly Ser Glu Ser Lys Ser Thr
1               5                   10

<210> SEQ ID NO 37
<211> LENGTH: 12
<212> TYPE: PRT
<213> ORGANISM: Artificial sequence
<220> FEATURE:
<223> OTHER INFORMATION: Synthetic sequence

<400> SEQUENCE: 37

Gly Ser Ala Gly Ser Ala Ala Gly Ser Gly Glu Phe
1               5                   10

<210> SEQ ID NO 38
<211> LENGTH: 852
<212> TYPE: DNA
<213> ORGANISM: Homo sapiens

<400> SEQUENCE: 38
atggagcctc ctggagactg ggggcctcct ccctggagat ccaccccccaa aaccgacgtc      60
ttgaggctgg tgctgtatct caccttcctg ggagccccct gctacgcccc agctctgccg     120
tcctgcaagg aggacgagta cccagtgggc tccgagtgct gccccaagtg cagtccaggt     180
tatcgtgtga aggaggcctg cggggagctg acgggcacag tgtgtgaacc ctgccctcca     240
ggcacctaca ttgcccacct caatggccta agcaagtgtc tgcagtgcca aatgtgtgac     300
ccagccatgg gcctgcgcgc gagccggaac tgctccagga cagagaacgc cgtgtgtggc     360
tgcagcccag ccacttctg catcgtccag gacgggacc actgcgccgc gtgccgcgct     420
tacgccacct ccagcccggg ccagagggtg cagaagggag gcaccgagag tcaggacacc     480
ctgtgtcaga actgcccccc ggggaccttc tctcccaatg gaccctgga ggaatgtcag     540
caccagacca gtgcagctg gctggtgacg aaggccggag ctgggaccag cagctcccac     600
tgggtatggt ggtttctctc agggagcctc gtcatcgtca ttgtttgctc cacagttggc     660
ctaatcatat gtgtgaaaag aagaaagcca aggggtgatg tagtcaaggt gatcgtctcc     720
gtccagcgga aaagacagga ggcagaaggt gaggccacag tcattgaggc cctgcaggcc     780
cctccggacg tcaccacggt ggccgtggag gagacaatac cctcattcac ggggaggagc     840
ccaaaccatt aa                                                         852

<210> SEQ ID NO 39
```

<211> LENGTH: 283
<212> TYPE: PRT
<213> ORGANISM: Homo sapiens

<400> SEQUENCE: 39

```
Met Glu Pro Pro Gly Asp Trp Gly Pro Pro Trp Arg Ser Thr Pro
1               5                   10                  15

Lys Thr Asp Val Leu Arg Leu Val Leu Tyr Leu Thr Phe Leu Gly Ala
            20                  25                  30

Pro Cys Tyr Ala Pro Ala Leu Pro Ser Cys Lys Glu Asp Glu Tyr Pro
            35                  40                  45

Val Gly Ser Glu Cys Cys Pro Lys Cys Ser Pro Gly Tyr Arg Val Lys
50                      55                      60

Glu Ala Cys Gly Glu Leu Thr Gly Thr Val Cys Glu Pro Cys Pro Pro
65                  70                  75                  80

Gly Thr Tyr Ile Ala His Leu Asn Gly Leu Ser Lys Cys Leu Gln Cys
                85                  90                  95

Gln Met Cys Asp Pro Ala Met Gly Leu Arg Ala Ser Arg Asn Cys Ser
            100                 105                 110

Arg Thr Glu Asn Ala Val Cys Gly Cys Ser Pro Gly His Phe Cys Ile
            115                 120                 125

Val Gln Asp Gly Asp His Cys Ala Ala Cys Arg Ala Tyr Ala Thr Ser
130                 135                 140

Ser Pro Gly Gln Arg Val Gln Lys Gly Gly Thr Glu Ser Gln Asp Thr
145                 150                 155                 160

Leu Cys Gln Asn Cys Pro Pro Gly Thr Phe Ser Pro Asn Gly Thr Leu
                165                 170                 175

Glu Glu Cys Gln His Gln Thr Lys Cys Ser Trp Leu Val Thr Lys Ala
            180                 185                 190

Gly Ala Gly Thr Ser Ser Ser His Trp Val Trp Trp Phe Leu Ser Gly
            195                 200                 205

Ser Leu Val Ile Val Ile Val Cys Ser Thr Val Gly Leu Ile Ile Cys
            210                 215                 220

Val Lys Arg Arg Lys Pro Arg Gly Asp Val Val Lys Val Ile Val Ser
225                 230                 235                 240

Val Gln Arg Lys Arg Gln Glu Ala Glu Gly Glu Ala Thr Val Ile Glu
                245                 250                 255

Ala Leu Gln Ala Pro Pro Asp Val Thr Thr Val Ala Val Glu Glu Thr
            260                 265                 270

Ile Pro Ser Phe Thr Gly Arg Ser Pro Asn His
            275                 280
```

<210> SEQ ID NO 40
<211> LENGTH: 4900
<212> TYPE: DNA
<213> ORGANISM: Homo sapiens

<400> SEQUENCE: 40

```
taaagtcatc aaaacaacgt tatatcctgt gtgaaatgct gcagtcagga tgccttgtgg      60
tttgagtgcc ttgatcatgt gccctaaggg gatggtggcg gtggtggtgg ccgtggatga     120
cggagactct caggccttgg caggtgcgtc tttcagttcc cctcacactt cgggttcctc     180
ggggaggagg ggctggaacc ctagcccatc gtcaggacaa agatgctcag gctgctcttg     240
gctctcaact tattcccttc aattcaagta acaggaaaca agattttggt gaagcagtcg     300
cccatgcttg tagcgtacga caatgcggtc aaccttagct gcaagtattc ctacaatctc    360
```

```
ttctcaaggg agttccggc atcccttcac aaaggactgg atagtgctgt ggaagtctgt      420
gttgtatatg ggaattactc ccagcagctt caggtttact caaaaacggg gttcaactgt      480
gatgggaaat tgggcaatga atcagtgaca ttctacctcc agaatttgta tgttaaccaa      540
acagatattt acttctgcaa aattgaagtt atgtatcctc ctccttacct agacaatgag      600
aagagcaatg gaaccattat ccatgtgaaa gggaaacacc tttgtccaag tcccctattt      660
cccgaccctt ctaagccctt ttgggtgctg gtggtggttg gtggagtcct ggcttgctat      720
agcttgctag taacagtggc ctttattatt ttctgggtga ggagtaagag gagcaggctc      780
ctgcacagtg actacatgaa catgactccc cgccgccccg ggcccacccg caagcattac      840
cagccctatg ccccaccacg cgacttcgca gcctatcgct cctgacacgg acgcctatcc      900
agaagccagc cggctggcag cccccatctg ctcaatatca ctgctctgga taggaaatga      960
ccgccatctc cagccggcca cctcaggccc ctgttgggcc accaatgcca atttttctcg     1020
agtgactaga ccaaatatca agatcatttt gagactctga aatgaagtaa aagagatttc     1080
ctgtgacagg ccaagtctta cagtgccatg gcccacattc caacttacca tgtacttagt     1140
gacttgactg agaagttagg gtagaaaaca aaaagggagt ggattctggg agcctcttcc     1200
ctttctcact cacctgcaca tctcagtcaa gcaaagtgtg gtatccacag acatttagt      1260
tgcagaagaa aggctaggaa atcattcctt ttggttaaat gggtgtttaa tcttttggtt     1320
agtgggttaa acggggtaag ttagagtagg gggagggata ggaagacata tttaaaaacc     1380
attaaaacac tgtctcccac tcatgaaatg agccacgtag ttcctattta atgctgtttt     1440
cctttagttt agaaatacat agacattgtc ttttatgaat tctgatcata tttagtcatt     1500
ttgaccaaat gagggatttg gtcaaatgag ggattccctc aaagcaatat caggtaaacc     1560
aagttgcttt cctcactccc tgtcatgaga cttcagtgtt aatgttcaca atatactttc     1620
gaaagaataa aatagttctc ctacatgaag aaagaatatg tcaggaaata aggtcacttt     1680
atgtcaaaat tatttgagta ctatgggacc tggcgcagtg gctcatgctt gtaatcccag     1740
cactttggga ggccgaggtg ggcagatcac ttgagatcag gaccagcctg gtcaagatgg     1800
tgaaactccg tctgtactaa aaatacaaaa tttagcttgg cctggtggca ggcacctgta     1860
atcccagctg cccaagaggc tgaggcatga gaatcgcttg aacctggcag gcggaggttg     1920
cagtgagccg agatagtgcc acagctctcc agcctgggcg acagagtgag actccatctc     1980
aaacaacaac aacaacaaca acaacaacaa caaaccacaa aattatttga gtactgtgaa     2040
ggattatttg tctaacagtt cattccaatc agaccaggta ggagctttcc tgtttcatat     2100
gtttcagggt tgcacagttg gtctctttaa tgtcggtgtg gagatccaaa gtgggttgtg     2160
gaaagagcgt ccataggaga agtgagaata ctgtgaaaaa gggatgttag cattcattag     2220
agtatgagga tgagtcccaa gaaggttctt tggaaggagg acgaatagaa tggagtaatg     2280
aaattcttgc catgtgctga ggagatagcc agcattaggt gacaatcttc cagaagtggt     2340
caggcagaag gtgccctggt gagagctcct ttacagggac tttatgtggt ttagggctca     2400
gagctccaaa actctgggct cagctgctcc tgtaccttgg aggtccattc acatgggaaa     2460
gtattttgga atgtgtcttt tgaagagagc atcagagttc ttaagggact gggtaaggcc     2520
tgaccctgaa atgaccatgg atattttcct acctacagtt tgagtcaact agaatatgcc     2580
tggggacctt gaagaatggc ccttcagtgg ccctcaccat tgttcatgc ttcagttaat      2640
tcaggtgttg aaggagctta ggttttagag gcacgtagac ttggttcaag tctcgttagt     2700
```

-continued

```
agttgaatag cctcaggcaa gtcactgccc acctaagatg atggttcttc aactataaaa    2760
tggagataat ggttacaaat gtctcttcct atagtataat ctccataagg gcatggccca    2820
agtctgtctt tgactctgcc tatccctgac atttagtagc atgcccgaca tacaatgtta    2880
gctattggta ttattgccat atagataaat tatgtataaa aattaaactg gcaatagcc     2940 taagaagggg ggaatattgt aacacaaatt taaacccact acgcagggat gaggtgctat    3000
aatatgagga cctttaact tccatcattt tcctgtttct tgaaatagtt tatcttgtaa     3060
tgaaatataa ggcacctccc acttttatgt atagaaagag gtcttttaat ttttttttaa    3120
tgtgagaagg aagggaggag taggaatctt gagattccag atcgaaaata ctgtactttg    3180 gttgatttt aagtgggctt ccattccatg gatttaatca gtcccaagaa gatcaaactc     3240
agcagtactt gggtgctgaa gaactgttgg atttaccctg gcacgtgtgc cacttgccag    3300
cttcttgggc acacagagtt cttcaatcca agttatcaga ttgtatttga aaatgacaga    3360
gctggagagt tttttgaaat ggcagtggca aataaataaa tacttttttt taaatggaaa    3420
gacttgatct atggtaataa atgattttgt tttctgactg gaaaaatagg cctactaaag    3480
atgaatcaca cttgagatgt ttcttactca ctctgcacag aaacaaagaa gaaatgttat    3540
acagggaagt ccgttttcac tattagtatg aaccaagaaa tggttcaaaa acagtggtag    3600
gagcaatgct ttcatagttt cagatatggt agttatgaag aaaacaatgt catttgctgc    3660
tattattgta agagtcttat aattaatggt actcctataa ttttgattg tgagctcacc     3720 tattgggtt aagcatgcca atttaaagag accaagtgta tgtacattat gttctacata    3780
ttcagtgata aaattactaa actactatat gtctgcttta aatttgtact ttaatattgt    3840
cttttggtat taagaaagat atgctttcag aatagatatg cttcgctttg gcaaggaatt    3900
tggatagaac ttgctattta aaagaggtgt ggggtaaatc cttgtataaa tctccagttt    3960
agcctttttt gaaaaagcta gactttcaaa tactaatttc acttcaagca gggtacgttt    4020
ctggtttgtt tgcttgactt cagtcacaat ttcttatcag accaatggct gacctctttg    4080
agatgtcagg ctaggcttac ctatgtgttc tgtgtcatgt gaatgctgag aagtttgaca    4140
gagatccaac ttcagccttg accccatcag tccctcgggt taactaactg agccaccggt    4200
cctcatggct attttaatga gggtattgat ggttaaatgc atgtctgatc ccttatccca    4260
gccatttgca ctgccagctg gaactatac cagacctgga tactgatccc aaagtgttaa     4320
attcaactac atgctggaga ttagagatgg tgccaataaa ggacccagaa ccaggatctt    4380
gattgctata gacttattaa taatccaggt caaagagagt gacacacact ctctcaagac    4440
ctggggtgag ggagtctgtg ttatctgcaa ggccatttga ggctcagaaa gtctctcttt    4500
cctatagata tatgcatact ttctgacata taggaatgta tcaggaatac tcaaccatca    4560
caggcatgtt cctacctcag ggcctttaca tgtcctgttt actctgtcta gaatgtcctt    4620
ctgtagatga cctggcttgc ctcgtcaccc ttcaggtcct tgctcaagtg tcatcttctc    4680
ccctagttaa actaccccac accctgtctg ctttccttgc ttattttct ccatagcatt     4740 ttaccatctc ttacattaga cattttctt atttatttgt agtttataag cttcatgagg     4800
caagtaactt tgctttgttt cttgctgtat ctccagtgcc cagagcagtg cctggtatat    4860
aataaatatt tattgactga gtgaaaaaaa aaaaaaaaa                           4900
```

<210> SEQ ID NO 41
<211> LENGTH: 220
<212> TYPE: PRT
<213> ORGANISM: Homo sapiens

<400> SEQUENCE: 41

```
Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220
```

<210> SEQ ID NO 42
<211> LENGTH: 1906
<212> TYPE: DNA
<213> ORGANISM: Homo sapiens

<400> SEQUENCE: 42

```
ccaagtcaca tgattcagga ttcaggggga gaatccttct tggaacagag atgggcccag      60
aactgaatca gatgaagaga gataaggtgt gatgtgggga agactatata agaatggac      120
ccagggctgc agcaagcact caacggaatg gcccctcctg agacacagc catgcatgtg      180
ccggcgggct ccgtggccag ccacctgggg accacgagcc gcagctattt ctatttgacc      240
acagccactc tggctctgtg ccttgtcttc acggtggcca ctattatggt gttggtcgtt      300
cagaggacgg actccattcc caactcacct gacaacgtcc ccctcaaagg aggaaattgc      360
tcagaagacc tcttatgtat cctgaaaaga gctccattca gaagtcatg ggcctacctc      420
caagtggcaa agcatctaaa caaaaccaag ttgtcttgga caaagatgg cattctccat      480
ggagtcagat atcaggatgg gaatctggtg atccaattcc ctggtttgta cttcatcatt      540
tgccaactgc agtttcttgt acaatgccca ataattctg tcgatctgaa gttggagctt      600
ctcatcaaca gcatatcaa aaaacaggcc ctggtgacag tgtgtgagtc tggaatgcaa      660
acgaaacacg tataccagaa tctctctcaa ttccttgctgg attacctgca ggtcaacacc      720
accatatcag tcaatgtgga tacattccag tacagata caagcacctt tcctcttgag      780
```

-continued

```
aatgtgttgt ccatcttctt atacagtaat tcagactgaa cagtttctct tggccttcag      840
gaagaaagcg cctctctacc atacagtatt tcatccctcc aaacacttgg gcaaaaagaa      900
aactttagac caagacaaac tacacagggt attaaatagt atacttctcc ttctgtctct      960
tggaaagata cagctccagg gttaaaaaga gagttttttag tgaagtatct ttcagatagc     1020
aggcagggaa gcaatgtagt gtggtgggca gagccccaca cagaatcaga agggatgaat     1080
ggatgtccca gcccaaccac taattcactg tatggtcttg atctatttct tctgttttga     1140
gagcctccag ttaaaatggg gcttcagtac cagagcagct agcaactctg ccctaatggg     1200
aaatgaaggg gagctgggtg tgagtgttta cactgtgccc ttcacgggat acttcttta     1260 tctgcagatg gcctaatgct tagttgtcca agtcgcgatc aaggactctc tcacacagga     1320
aacttcccta tactggcaga tacacttgtg actgaaccat gcccagttta tgcctgtctg     1380
actgtcactc tggcactagg aggctgatct tgtactccat atgaccccac ccctaggaac     1440
ccccagggaa aaccaggctc ggacagcccc ctgttcctga gatggaaagc acaaatttaa     1500
tacaccacca caatggaaaa caagttcaaa gactttact tacagatcct ggacagaaag     1560
ggcataatga gtctgaaggg cagtcctcct tctccaggtt acatgaggca ggaataagaa     1620
gtcagacaga gacagcaaga cagttaacaa cgtaggtaaa gaaatagggt gtggtcactc     1680
tcaattcact ggcaaatgcc tgaatggtct gtctgaagga agcaacgag aagtggggaa      1740 tccagtctgc taggcaggaa agatgcctct aagttcttgt ctctggccag aggtgtggta     1800
tagaaccaga aacccatatc aagggtgact aagcccggct tccggtatga gaaattaaac     1860
ttgtatacaa aatggttgcc aaggcaacat aaaattataa gaattc                    1906
```

<210> SEQ ID NO 43
<211> LENGTH: 234
<212> TYPE: PRT
<213> ORGANISM: Homo sapiens

<400> SEQUENCE: 43

```
Met Asp Pro Gly Leu Gln Gln Ala Leu Asn Gly Met Ala Pro Pro Gly
1               5                   10                  15

Asp Thr Ala Met His Val Pro Ala Gly Ser Val Ala Ser His Leu Gly
            20                  25                  30

Thr Thr Ser Arg Ser Tyr Phe Tyr Leu Thr Thr Ala Thr Leu Ala Leu
        35                  40                  45

Cys Leu Val Phe Thr Val Ala Thr Ile Met Val Leu Val Val Gln Arg
    50                  55                  60

Thr Asp Ser Ile Pro Asn Ser Pro Asp Asn Val Pro Leu Lys Gly Gly
65                  70                  75                  80

Asn Cys Ser Glu Asp Leu Leu Cys Ile Leu Lys Arg Ala Pro Phe Lys
                85                  90                  95

Lys Ser Trp Ala Tyr Leu Gln Val Ala Lys His Leu Asn Lys Thr Lys
            100                 105                 110

Leu Ser Trp Asn Lys Asp Gly Ile Leu His Gly Val Arg Tyr Gln Asp
        115                 120                 125

Gly Asn Leu Val Ile Gln Phe Pro Gly Leu Tyr Phe Ile Ile Cys Gln
    130                 135                 140

Leu Gln Phe Leu Val Gln Cys Pro Asn Asn Ser Val Asp Leu Lys Leu
145                 150                 155                 160

Glu Leu Leu Ile Asn Lys His Ile Lys Lys Gln Ala Leu Val Thr Val
                165                 170                 175
```

Cys Glu Ser Gly Met Gln Thr Lys His Val Tyr Gln Asn Leu Ser Gln
            180                 185                 190

Phe Leu Leu Asp Tyr Leu Gln Val Asn Thr Thr Ile Ser Val Asn Val
        195                 200                 205

Asp Thr Phe Gln Tyr Ile Asp Thr Ser Thr Phe Pro Leu Glu Asn Val
    210                 215                 220

Leu Ser Ile Phe Leu Tyr Ser Asn Ser Asp
225                 230

<210> SEQ ID NO 44
<211> LENGTH: 1629
<212> TYPE: DNA
<213> ORGANISM: Homo sapiens

<400> SEQUENCE: 44

| | | | | | |
|---|---|---|---|---|---|
| tttcctgggc | ggggccaagg | ctggggcagg | ggagtcagca | gaggcctcgc | tcgggcgccc | 60 |
| agtggtcctg | ccgcctggtc | tcacctcgct | atggttcgtc | tgcctctgca | gtgcgtcctc | 120 |
| tggggctgct | tgctgaccgc | tgtccatcca | gaacccaccca | ctgcatgcag | agaaaaacag | 180 |
| tacctaataa | acagtcagtg | ctgttctttg | tgccagccag | gacagaaact | ggtgagtgac | 240 |
| tgcacagagt | tcactgaaac | ggaatgcctt | ccttgcggtg | aaagcgaatt | cctagacacc | 300 |
| tggaacagag | agacacactg | ccaccagcac | aaatactgcg | accccaacct | agggcttcgg | 360 |
| gtccagcaga | agggcacctc | agaaacagac | accatctgca | cctgtgaaga | aggctggcac | 420 |
| tgtacgagtg | aggcctgtga | gagctgtgtc | ctgcaccgct | catgctcgcc | cggctttggg | 480 |
| gtcaagcaga | ttgctacagg | ggtttctgat | accatctgcg | agccctgccc | agtcggcttc | 540 |
| ttctccaatg | tgtcatctgc | tttcgaaaaa | tgtcacccct | tggacaagctg | tgagaccaaa | 600 |
| gacctggttt | gcaacagag | aggcacaaac | aagactgatg | ttgtctgtgg | tccccaggat | 660 |
| cggctgagag | ccctggtggt | gatccccatc | atcttcggga | tcctgtttgc | catcctcttg | 720 |
| gtgctggtct | ttatcaaaaa | ggtggccaag | aagccaacca | ataaggcccc | ccaccccaag | 780 |
| caggaacccc | aggagatcaa | ttttcccgac | gatcttcctg | gctccaacac | tgctgctcca | 840 |
| gtgcaggaga | ctttacatgg | atgccaaccg | tcacccagg | aggatggcaa | agagagtcgc | 900 |
| atctcagtgc | aggagagaca | gtgaggctgc | acccacccag | gagtgtggcc | acgtgggcaa | 960 |
| acaggcagtt | ggccagagag | cctggtgctg | ctgctgctgt | ggcgtgaggg | tgaggggctg | 1020 |
| gcactgactg | ggcatagctc | cccgcttctg | cctgcacccc | tgcagtttga | dacaggagac | 1080 |
| ctggcactgg | atgcagaaac | agttcacctt | gaagaacctc | tcacttcacc | ctggagccca | 1140 |
| tccagtctcc | caacttgtat | taaagacaga | ggcagaagtt | tggtggtggt | ggtgttgggg | 1200 |
| tatggtttag | taatatccac | cagaccttcc | gatccagcag | tttggtgccc | agagaggcat | 1260 |
| catggtggct | tccctgcgcc | caggaagcca | tatacacaga | tgcccattgc | agcattgttt | 1320 |
| gtgatagtga | acaactggaa | gctgcttaac | tgtccatcag | caggagactg | gctaaataaa | 1380 |
| attagaatat | atttatacaa | cagaatctca | aaaacactgt | tgagtaagga | aaaaaaggca | 1440 |
| tgctgctgaa | tgatgggtat | ggaacttttt | aaaaaagtac | atgctttat | gtatgtatat | 1500 |
| tgcctatgga | tatatgtata | aatacaatat | gcatcatata | ttgatataac | aagggttctg | 1560 |
| gaagggtaca | cagaaaaccc | acagctcgaa | gagtggtgac | gtctggggtg | gggaagaagg | 1620 |
| gtctgggg | | | | | | 1629 |

<210> SEQ ID NO 45
<211> LENGTH: 277

<212> TYPE: PRT
<213> ORGANISM: Homo sapiens

<400> SEQUENCE: 45

```
Met Val Arg Leu Pro Leu Gln Cys Val Leu Trp Gly Cys Leu Leu Thr
1               5                   10                  15

Ala Val His Pro Glu Pro Thr Ala Cys Arg Glu Lys Gln Tyr Leu
            20                  25                  30

Ile Asn Ser Gln Cys Cys Ser Leu Cys Gln Pro Gly Gln Lys Leu Val
            35                  40                  45

Ser Asp Cys Thr Glu Phe Thr Glu Thr Glu Cys Leu Pro Cys Gly Glu
        50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
        195                 200                 205

Leu Leu Val Leu Val Phe Ile Lys Lys Val Ala Lys Lys Pro Thr Asn
210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
            260                 265                 270

Val Gln Glu Arg Gln
        275
```

<210> SEQ ID NO 46
<211> LENGTH: 913
<212> TYPE: DNA
<213> ORGANISM: Homo sapiens

<400> SEQUENCE: 46

```
ccagagaggg gcaggctggt cccctgacag gttgaagcaa gtagacgccc aggagccccg    60 ggaggggggct gcagtttcct tccttccttc tcggcagcgc tccgcgcccc catcgcccct   120
cctgcgctag cggaggtgat cgccgcgcg atgccgagg agggttcggg ctgctcggtg     180
cggcgcaggc cctatgggtg cgtcctgcgg gctgctttgg tcccattggt cgcgggcttg    240
gtgatctgcc tcgtggtgtg catccagcgc ttcgcacagg ctcagcagca gctgccgctc    300
gagtcacttg ggtgggacgt agctgagctg cagctgaatc acacaggacc tcagcaggac    360
```

-continued

```
cccaggctat actggcaggg ggcccagca ctgggccgct ccttcctgca tggaccagag    420
ctggacaagg ggcagctacg tatccatcgt gatggcatct acatggtaca catccaggtg    480
acgctggcca tctgctcctc cacgacggcc tccaggcacc accccaccac cctggccgtg    540
ggaatctgct ctcccgcctc ccgtagcatc agcctgctgc gtctcagctt ccaccaaggt    600
tgtaccattg cctcccagcg cctgacgccc ctggcccgag ggacacact ctgcaccaac     660 ctcactggga cacttttgcc ttcccgaaac actgatgaga ccttctttgg agtgcagtgg    720
gtgcgcccct gaccactgct gctgattagg gttttttaaa ttttatttta ttttatttaa   780
gttcaagaga aaaagtgtac acacaggggc cacccggggt tggggtggga gtgtggtggg   840
gggtagtggt ggcaggacaa gagaaggcat tgagcttttt ctttcatttt cctattaaaa   900
aatacaaaaa tca                                                       913
```

<210> SEQ ID NO 47
<211> LENGTH: 193
<212> TYPE: PRT
<213> ORGANISM: Homo sapiens

<400> SEQUENCE: 47

```
Met Pro Glu Glu Gly Ser Gly Cys Ser Val Arg Arg Arg Pro Tyr Gly
1               5                   10                  15

Cys Val Leu Arg Ala Ala Leu Val Pro Leu Val Ala Gly Leu Val Ile
            20                  25                  30

Cys Leu Val Val Cys Ile Gln Arg Phe Ala Gln Ala Gln Gln Gln Leu
        35                  40                  45

Pro Leu Glu Ser Leu Gly Trp Asp Val Ala Glu Gln Leu Asn His
    50                  55                  60

Thr Gly Pro Gln Gln Asp Pro Arg Leu Tyr Trp Gln Gly Gly Pro Ala
65                  70                  75                  80

Leu Gly Arg Ser Phe Leu His Gly Pro Glu Leu Asp Lys Gly Gln Leu
                85                  90                  95

Arg Ile His Arg Asp Gly Ile Tyr Met Val His Ile Gln Val Thr Leu
            100                 105                 110

Ala Ile Cys Ser Ser Thr Thr Ala Ser Arg His His Pro Thr Thr Leu
        115                 120                 125

Ala Val Gly Ile Cys Ser Pro Ala Ser Arg Ser Ile Ser Leu Leu Arg
    130                 135                 140

Leu Ser Phe His Gln Gly Cys Thr Ile Ala Ser Gln Arg Leu Thr Pro
145                 150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
            180                 185                 190

Pro
```

<210> SEQ ID NO 48
<211> LENGTH: 723
<212> TYPE: DNA
<213> ORGANISM: Homo sapiens

<400> SEQUENCE: 48

```
atggaggaga gtgtcgtacg gccctcagtg tttgtggtgg atggacagac cgacatccca    60
ttcacgaggc tggacgaag ccaccggaga cagtcgtgca gtgtgcccg ggtgggtctg      120 ggtctcttgc tgttgctgat gggggccggg ctggccgtcc aaggctggtt cctcctgcag   180
```

```
ctgcactggc gtctaggaga gatggtcacc cgcctgcctg acggacctgc aggctcctgg      240
gagcagctga tacaagagcg aaggtctcac gaggtcaacc cagcagcgca tctcacaggg      300
gccaactcca gcttgaccgg cagcgggggg ccgctgttat gggagactca gctgggcctg      360
gccttcctga ggggcctcag ctaccacgat ggggcccttg tggtcaccaa agctggctac      420
tactacatct actccaaggt gcagctgggc ggtgtgggct gcccgctggg cctggccagc      480
accatcaccc acggcctcta caagcgcaca ccccgctacc ccgaggagct ggagctgttg      540
gtcagccagc agtcaccctg cggacgggcc accagcagct cccgggtctg gtgggacagc      600
agcttcctgg gtggtgtggt acacctggag gctggggagg aggtggtcgt ccgtgtgctg      660
gatgaacgcc tggttcgact gcgtgatggt acccggtctt acttcggggc tttcatggtg      720
tga                                                                   723

<210> SEQ ID NO 49
<211> LENGTH: 240
<212> TYPE: PRT
<213> ORGANISM: Homo sapiens

<400> SEQUENCE: 49

Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
            20                  25                  30

Cys Ser Val Ala Arg Val Gly Leu Gly Leu Leu Leu Leu Leu Met Gly
        35                  40                  45

Ala Gly Leu Ala Val Gln Gly Trp Phe Leu Leu Gln Leu His Trp Arg
    50                  55                  60

Leu Gly Glu Met Val Thr Arg Leu Pro Asp Gly Pro Ala Gly Ser Trp
65                  70                  75                  80

Glu Gln Leu Ile Gln Glu Arg Arg Ser His Glu Val Asn Pro Ala Ala
                85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
        115                 120                 125

His Asp Gly Ala Leu Val Val Thr Lys Ala Gly Tyr Tyr Tyr Ile Tyr
    130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Arg Val Trp Trp Asp Ser Ser Phe Leu Gly Gly Val Val His
        195                 200                 205

Leu Glu Ala Gly Glu Glu Val Val Arg Val Leu Asp Glu Arg Leu
    210                 215                 220

Val Arg Leu Arg Asp Gly Thr Arg Ser Tyr Phe Gly Ala Phe Met Val
225                 230                 235                 240
```